US009433652B2

(12) United States Patent
Honda et al.

(10) Patent No.: US 9,433,652 B2
(45) **Date of Patent: *Sep. 6, 2016**

(54) COMPOSITION FOR INDUCING PROLIFERATION OR ACCUMULATION OF REGULATORY T CELLS

(71) Applicant: The University of Tokyo, Tokyo (JP)

(72) Inventors: Kenya Honda, Tokyo (JP); Koji Atarashi, Tokyo (JP); Kikuji Itoh, Tokyo (JP); Takeshi Tanoue, Tokyo (JP)

(73) Assignee: The University of Tokyo, Tokyo (JP)

( * ) Notice: Subject to any disclaimer, the term of this patent is extended or adjusted under 35 U.S.C. 154(b) by 74 days.

This patent is subject to a terminal disclaimer.

(21) Appl. No.: 14/492,850

(22) Filed: Sep. 22, 2014

(65) Prior Publication Data

US 2015/0143557 A1 May 21, 2015
US 2015/0320805 A9 Nov. 12, 2015

Related U.S. Application Data

(63) Continuation of application No. 13/701,467, filed as application No. PCT/JP2011/063302 on Jun. 3, 2011, now abandoned.

(30) Foreign Application Priority Data

Jun. 4, 2010 (JP) ................................ 2010-129134
Dec. 3, 2010 (WO) .................. PCT/JP2010/071746

(51) Int. Cl.

| | |
|---|---|
| ***A61K 35/74*** | (2015.01) |
| ***A61K 35/742*** | (2015.01) |
| ***A61K 45/06*** | (2006.01) |
| ***G01N 33/50*** | (2006.01) |
| ***A61K 45/00*** | (2006.01) |
| ***A01K 67/027*** | (2006.01) |
| ***C12Q 1/68*** | (2006.01) |
| ***A61K 9/00*** | (2006.01) |
| *A61K 35/00* | (2006.01) |

(52) U.S. Cl.
CPC ......... *A61K 35/742* (2013.01); *A01K 67/0275* (2013.01); *A61K 9/0053* (2013.01); *A61K 35/74* (2013.01); *A61K 45/00* (2013.01); *A61K 45/06* (2013.01); *C12Q 1/689* (2013.01); *G01N 33/505* (2013.01); *A01K 2267/0325* (2013.01); *A61K 35/00* (2013.01); *G01N 2333/33* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 4,576,936 | A | 3/1986 | MacDonald |
| 5,599,795 | A | 2/1997 | McCann et al. |
| 5,700,787 | A | 12/1997 | Tzianabos et al. |
| 6,348,452 | B1 | 2/2002 | Brown et al. |
| 6,551,632 | B2 | 4/2003 | Borody |
| 6,645,530 | B1 | 11/2003 | Borody |
| 7,629,330 | B2 | 12/2009 | Wang et al. |
| 7,749,494 | B2 | 7/2010 | Renaud et al. |
| 2003/0113306 | A1 | 6/2003 | Collins et al. |
| 2004/0028689 | A1 | 2/2004 | Borody |
| 2004/0170617 | A1 | 9/2004 | Finegold |
| 2004/0219160 | A1 | 11/2004 | Tzianabos et al. |
| 2006/0067924 | A1 | 3/2006 | Lee et al. |
| 2006/0240482 | A1 | 10/2006 | Kwok et al. |
| 2007/0258953 | A1 | 11/2007 | Duncan et al. |
| 2008/0003207 | A1 | 1/2008 | Cui |
| 2008/0305089 | A1 | 12/2008 | Bufe et al. |
| 2008/0311080 | A1 | 12/2008 | Collins et al. |
| 2009/0124573 | A1 | 5/2009 | Mazmanian et al. |
| 2009/0317427 | A1 | 12/2009 | Kasper et al. |
| 2010/0119488 | A1 | 5/2010 | Huber-Haag et al. |
| 2010/0275282 | A1 | 10/2010 | Round et al. |
| 2011/0009360 | A1 | 1/2011 | Kasper et al. |
| 2012/0027734 | A1 | 2/2012 | Van Immerseel et al. |
| 2012/0276149 | A1 | 11/2012 | Littman et al. |
| 2013/0149339 | A1 | 6/2013 | Honda et al. |
| 2014/0341921 | A1 | 11/2014 | Honda et al. |
| 2015/0224152 | A1 | 8/2015 | Littman et al. |
| 2016/0143960 | A1 | 5/2016 | Honda et al. |
| 2016/0151430 | A1 | 6/2016 | Honda et al. |

FOREIGN PATENT DOCUMENTS

| | | | |
|---|---|---|---|
| CA | 2850000 | A1 | 4/2013 |
| DE | 102006062250 | A1 | 6/2008 |
| EP | 1749538 | A1 | 2/2007 |

(Continued)

OTHER PUBLICATIONS

Third Party Observations filed in European Patent Application No. 11728077.6 on Jan. 29, 2016.

(Continued)

*Primary Examiner* — Brian J Gangle
(74) *Attorney, Agent, or Firm* — Wolf, Greenfield & Sacks, P.C.

(57) ABSTRACT

It was found that bacteria belonging to the genus *Clostridium* induce accumulation of regulatory T cells (Treg cells) in the colon. Moreover, the present inventors found that regulatory T cells (Treg cells) induced by from these bacteria suppressed proliferation of effector T-cells. From these findings, the present inventors found that the use of bacteria belonging to the genus *Clostridium* or a physiologically active substance derived therefrom made it possible to induce proliferation or accumulation of regulatory T cells (Treg cells), and further to suppress immune functions.

13 Claims, 37 Drawing Sheets

(56) References Cited

FOREIGN PATENT DOCUMENTS

| | | | |
|---|---|---|---|
| EP | 1955706 | A1 | 8/2008 |
| JP | 2009-084215 | A | 4/2009 |
| WO | WO 2009/050486 | A2 | 4/2009 |
| WO | WO 2009/149149 | A1 | 12/2009 |
| WO | WO 2011/005756 | A1 | 1/2011 |
| WO | WO 2011/022542 | A2 | 2/2011 |
| WO | WO 2011/022660 | A1 | 2/2011 |
| WO | WO 2011/151941 | A1 | 12/2011 |
| WO | WO 2011/152566 | A2 | 12/2011 |
| WO | WO 2013/080561 | A1 | 6/2013 |
| WO | WO 2015/156419 | A1 | 10/2015 |

OTHER PUBLICATIONS

[No Author Listed] Ruminococcus. Microbe Wild. Aug. 2010. Last accessed at https://microbewiki.kenyon.edu/index.php/Ruminococcus on Apr. 19, 2016.
Abraham et al., Molecular mechanisms of IL-2 gene regulation following costimulation through LFA-1. J Immunol. Nov. 1, 2001;167(9):5193-201.
Abrams, Open-Label, Uncontrolled Trial of Bowel Sterilization and Repopulation With Normal Bowel Flora for Treatment of Inflammatory Bowel Disease. Current Therapeutic Research. Dec. 1997;58(12):1001-1012.
Andoh et al., Faecal microbiota profile of Crohn's disease determined by terminal restriction fragment length polymorphism analysis. Aliment Pharmacol Ther. Jan. 2009;29(1):75-82. doi: 10.1111/j.1365-2036.2008.03860.x. Epub Sep. 26, 2008.
Atarashi et al., ATP drives lamina propria T(H)17 cell differentiation. Nature. Oct. 9, 2008;455(7214):808-12. doi: 10.1038/nature07240. Epub Aug. 20, 2008.
Atarashi et al., Microbiota in autoimmunity and tolerance. Curr Opin Immunol. Dec. 2011;23(6):761-8. doi: 10.1016/j.coi.2011.11.002. Epub Nov. 22, 2011. Review.
Atarashi et al., Treg induction by a rationally selected mixture of Clostridia strains from the human microbiota. Nature. Aug. 8, 2013;500(7461):232-6. doi: 10.1038/nature12331. Epub Jul. 10, 2013.
Barnes et al., Regulatory T cells reinforce intestinal homeostasis. Immunity. Sep. 18, 2009;31(3):401-11. doi: 10.1016/j.immuni.2009.08.011.
Bassaganya-Riera et al., Punicic acid modulates mucosal immune responses and prevents gut inflammation through PPAR gamma and delta-dependent mechanisms. FASEB J. 2010; 24 (Meeting Abstract Supplement). Abstract.
Bassaganya-Riera et al., Soluble fibers and resistant starch ameliorate disease activity in an experimental model of inflammatory bowel disease. FASEB J. 2010; 24 (Meeting Abstract Supplement). Abstract.
Borody et al., Treatment of ulcerative colitis using fecal bacteriotherapy. J Clin Gastroenterol. Jul. 2003;37(1):42-7.
Bouskra et al., Lymphoid tissue genesis induced by commensals through NOD1 regulates intestinal homeostasis. Nature. Nov. 27, 2008;456(7221):507-10. doi: 10.1038/nature07450. Epub Nov. 5, 2008.
Browne et al., Culturing of 'unculturable' human microbiota reveals novel taxa and extensive sporulation. Nature. May 4, 2016. doi: 10.1038/nature17645.
Cebra, Influences of microbiota on intestinal immune system development. Am J Clin Nutr. May 1999;69(5):1046S-1051S.
Curotto De Lafaille et al., Natural and adaptive foxp3+ regulatory T cells: more of the same or a division of labor? Immunity. May 2009;30(5):626-35. doi: 10.1016/j.immuni.2009.05.002.
Di Giacinto et al., Probiotics ameliorate recurrent Th1-mediated murine colitis by inducing IL-10 and IL-10-dependent TGF-beta-bearing regulatory cells. J Immunol. Mar. 15, 2005;174(6):3237-46.
Eeckhaut et al., The anaerobic butyrate-producing strain Butyricicoccus pullicaecorum decreases colonic inflammation and ulceration in a TNBS-induced colitis rat model. In:5th Probiotics, Prebiotics and New Foods Congress. Rome, Italy (2009).
Foditsch et al., Isolation and characterization of Faecalibacterium prausnitzii from calves and piglets. PLoS One. Dec. 31, 2014;9(12):e116465. doi: 10.1371/journal.pone.0116465. eCollection 2014.
Foligne et al., A key role of dendritic cells in probiotic functionality. PLoS One. Mar. 21, 2007;2(3):e313.
Foligne et al., Correlation between in vitro and in vivo immunomodulatory properties of lactic acid bacteria. World J Gastroenterol. Jan. 14, 2007;13(2):236-43.
Frank et al., Molecular-phylogenetic characterization of microbial community imbalances in human inflammatory bowel diseases. Proc Natl Acad Sci U S A. Aug. 21, 2007;104(34):13780-5. Epub Aug. 15, 2007.
Garrett et al., Communicable ulcerative colitis induced by T-bet deficiency in the innate immune system. Cell. Oct. 5, 2007;131(1):33-45.
Geuking et al., Intestinal bacterial colonization induces mutualistic regulatory T cell responses. Immunity. May 27, 2011;34(5):794-806. doi: 10.1016/j.immuni.2011.03.021. Epub May 19, 2011.
Grehan et al., Durable alteration of the colonic microbiota by the administration of donor fecal flora. J Clin Gastroenterol. Sep. 2010;44(8):551-61. doi: 10.1097/MCG.0b013e3181e5d06b.
Hart et al., Modulation of human dendritic cell phenotype and function by probiotic bacteria. Gut. Nov. 2004;53(11):1602-9.
Hata et al., Blood group B degrading activity of Ruminococcus gnavus alpha-galactosidase. Artif Cells Blood Substit Immobil Biotechnol. May 2004;32(2):263-74.
Itoh et al., Colonization resistance against Pseudomonas aeruginosa in gnotobiotic mice. Lab Anim. Jul. 1986;20(3):197-201.
Itoh et al., Intestinal bacteria antagonistic to Clostridium difficile in mice. Lab Anim. Jan. 1987;21(1):20-5.
Ivanov et al., Induction of intestinal Th17 cells by segmented filamentous bacteria. Cell. Oct. 30, 2009;139(3):485-98. doi: 10.1016/j.cell.2009.09.033.
Ivanov et al., Specific microbiota direct the differentiation of IL-17-producing T-helper cells in the mucosa of the small intestine. Cell Host Microbe. Oct. 16, 2008;4(4):337-49. doi: 10.1016/j.chom.2008.09.009.
Jarry et al., Mucosal IL-10 and TGF-beta play crucial roles in preventing LPS-driven, IFN-gamma-mediated epithelial damage in human colon explants. J Clin Invest. Mar. 2008;118(3):1132-42.
Khoruts et al., Changes in the composition of the human fecal microbiome after bacteriotherapy for recurrent Clostridium difficile-associated diarrhea. J Clin Gastroenterol. May-Jun. 2010;44(5):354-60. doi: 10.1097/MCG.0b013e3181c87e02.
Kwon et al., Generation of regulatory dendritic cells and CD4+Foxp3+ T cells by probiotics administration suppresses immune disorders. Proc Natl Acad Sci U S A. Feb. 2, 2010;107(5):2159-64. doi: 10.1073/pnas.0904055107. Epub Jan. 13, 2010.
Latvala et al., Potentially probiotic bacteria induce efficient maturation but differential cytokine production in human monocyte-derived dendritic cells. World J Gastroenterol. Sep. 28, 2008;14(36):5570-83; discussion 5581-2.
Lawley et al., Targeted restoration of the intestinal microbiota with a simple, defined bacteriotherapy resolves relapsing Clostridium difficile disease in mice. PLoS Pathog. 2012;8(10):e1002995. doi: 10.1371/journal.ppat.1002995. Epub Oct. 25, 2012.
Livingston et al., Gut commensal Lactobacillus reuteri 100-23 stimulates an immunoregulatory response. Immunol Cell Biol. Jan. 2010;88(1):99-102. doi: 10.1038/icb.2009.71. Epub Sep. 29, 2009.
Louis et al., Diversity, metabolism and microbial ecology of butyrate-producing bacteria from the human large intestine. FEMS Microbiol Lett. May 2009;294(1):1-8. doi: 10.1111/j.1574-6968.2009.01514.x. Epub Feb. 13, 2009.
Lu et al., Molecular orchestration of differentiation and function of regulatory T cells. Genes Dev. Jun. 1, 2009;23(11):1270-82. doi:10.1101/gad.1791009.
MacPherson et al., Interactions between commensal intestinal bacteria and the immune system. Nat Rev Immunol. Jun. 2004;4(6):478-85.

(56) References Cited

OTHER PUBLICATIONS

Mangin et al., Molecular inventory of faecal microflora in patients with Crohn's disease. FEMS Microbiol Ecol. Oct. 1, 2004;50(1):25-36. doi: 10.1016/j.femsec.2004.05.005.
Maslowski et al., Regulation of inflammatory responses by gut microbiota and chemoattractant receptor GPR43. Nature. Oct. 29, 2009;461(7268):1282-6. doi: 10.1038/nature08530.
Maynard et al., Regulatory T cells expressing interleukin 10 develop from Foxp3+ and Foxp3− precursor cells in the absence of interleukin 10. Nat Immunol. Sep. 2007;8(9):931-41. Epub Aug. 12, 2007.
Mazmanian et al., A microbial symbiosis factor prevents intestinal inflammatory disease. Nature. May 29, 2008;453(7195):620-5. doi:10.1038/nature07008.
Mazmanian, Gut immune balance is as easy as S-F-B. Immunity. Oct. 16, 2009;31(4):536-8. doi: 10.1016/j.immuni.2009.09.005.
Miquel et al., Faecalibacterium prausnitzii and human intestinal health. Curr Opin Microbiol. Jun. 2013;16(3):255-61. doi:10.1016/j.mib.2013.06.003. Epub Jul. 3, 2013. Review.
Miyake et al., Dysbiosis in the Gut Microbiota of Patients with Multiple Sclerosis, with a Striking Depletion of Species Belonging to Clostridia XIVa and IV Clusters. PLoS One. Sep. 14, 2015;10(9):e0137429. doi: 10.1371/journal.pone.0137429. eCollection 2015.
Narushima et al., Characterization of the 17 strains of regulatory T cell-inducing human-derived Clostridia. Gut Microbes. May-Jun. 2014;5(3):333-9. doi: 10.4161/gmic.28572. Epub Mar. 18, 2014.
O'Mahony et al., Commensal-induced regulatory T cells mediate protection against pathogen-stimulated NF-kappaB activation. PLoS Pathog. Aug. 1, 2008;4(8):e1000112. doi: 10.1371/journal.ppat.1000112.
Paredes-Sabja et al., Clostridium difficile spore biology:sporulation, germination, and spore structural proteins. Trends Microbiol. Jul. 2014;22(7):406-16. doi: 10.1016/j.tim.2014.04.003. Epub May 7, 2014.
Qin et al., A human gut microbial gene catalogue established by metagenomic sequencing. Nature. Mar. 4, 2010;464(7285):59-65. doi: 10.1038/nature08821.
Qiu et al., C. Faecalibacterium prausnitzii upregulates regulatory T cells and anti-inflammatory cytokines in treating TNBS-induced colitis. J Crohns Colitis. Dec. 1, 2013;7(11):e558-68. doi: 10.1016/j.crohns.2013.04.002. Epub May 2, 2013.
Rehman et al., Transcriptional activity of the dominant gut mucosal microbiota in chronic inflammatory bowel disease patients. J Med Microbiol. Sep. 2010;59(Pt 9):1114-22. doi:10.1099/jmm.0.021170-0. Epub Jun. 3, 2010.
Rosero et al., Reclassification of Eubacterium rectale (Prévot et al., 1967) in a new genus *Agathobacter* gen. nov., as *Agathobacter rectalis* comb. nov., within the family Lachnospiraceae, and description of *Agathobacter ruminis* sp. nov., from the rumen. Int J Syst Evol Microbiol. Nov. 30, 2015. doi: 10.1099/ijsem.0.000788.
Rossi et al., Faecalibacterium prausnitzii A2-165 has a high capacity to induce IL-10 in human and murine dendritic cells and modulates T cell responses. Sci Rep. Jan. 4, 2016;6:18507. doi:10.1038/srep18507.
Round et al., Inducible Foxp3+ regulatory T-cell development by a commensal bacterium of the intestinal microbiota. Proc Natl Acad Sci U S A. Jul. 6, 2010;107(27):12204-9. doi: 10.1073/pnas.0909122107. Epub Jun. 21, 2010.
Round et al., The gut microbiota shapes intestinal immune responses during health and disease. Nat Rev Immunol. May 2009;9(5):313-23. doi:10.1038/nri2515. Review. Erratum in: Nat Rev Immunol. Aug. 2009;9(8):600.
Rubtsov et al., Regulatory T cell-derived interleukin-10 limits inflammation at environmental interfaces. Immunity. Apr. 2008;28(4):546-58. doi: 10.1016/j.immuni.2008.02.017.
Sakaguchi et al., Regulatory T cells and immune tolerance. Cell. May 30, 2008;133(5):775-87. doi: 10.1016/j.cell.2008.05.009.
Salzman et al., Enteric defensins are essential regulators of intestinal microbial ecology. Nat Immunol. Jan. 2010;11(1):76-83. doi:10.1038/ni.1825. Epub Oct. 22, 2009.
Sanos et al., RORgammat and commensal microflora are required for the differentiation of mucosal interleukin 22-producing NKp46+ cells. Nat Immunol. Jan. 2009;10(1):83-91. doi: 10.1038/ni.1684. Epub Nov. 23, 2008.
Schloss et al., The dynamics of a family's gut microbiota reveal variations on a theme. Microbiome. Jul. 21, 2014;2:25. doi:10.1186/2049-2618-2-25. eCollection 2014.
Schouten et al., Oligosaccharide-induced whey-specific CD25(+) regulatory T-cells are involved in the suppression of cow milk allergy in mice. J Nutr. Apr. 2010;140(4):835-41. doi: 10.3945/jn.109.116061. Epub Feb. 17, 2010.
Segain et al., Butyrate inhibits inflammatory responses through NFkappaB inhibition: implications for Crohn's disease. Gut. Sep. 2000;47(3):397-403.
So et al., Lactobacillus casei potentiates induction of oral tolerance in experimental arthritis. Mol Immunol. Nov. 2008;46(1):172-80. doi: 10.1016/j.molimm.2008.07.038. Epub Sep. 19, 2008.
So et al., Lactobacillus casei suppresses experimental arthritis by down-regulating T helper 1 effector functions. Mol Immunol. May 2008;45(9):2690-9. doi:10.1016/j.molimm.2007.12.010. Epub Feb. 19, 2008.
Sokol et al., Low counts of Faecalibacterium prausnitzii in colitis microbiota. Inflamm Bowel Dis. Aug. 2009;15(8):1183-9. doi:10.1002/ibd.20903.
Song et al., *Clostridium bartlettii* sp. nov., isolated from human faeces. Anaerobe. Jun. 2004;10(3):179-84.
Tao et al., Deacetylase inhibition promotes the generation and function of regulatory T cells. Nat Med. Nov. 2007;13(11):1299-307. Epub Oct. 7, 2007.
Thibault et al., Butyrate utilization by the colonic mucosa in inflammatory bowel diseases: a transport deficiency. Inflamm Bowel Dis. Apr. 2010;16(4):684-95. doi:10.1002/ibd.21108.
Umesaki et al., Differential roles of segmented filamentous bacteria and clostridia in development of the intestinal immune system. Infect Immun. Jul. 1999;67(7):3504-11.
Valcheva et al., Prebiotics Prevent Loss of Intestinal Biodiversity and Reduce Colitis in Hla-B27 Transgenic Rats. Canadian Digestive Diseases Week. Feb. 2009 Poster Session 2—Immunology and Inflammatory Bowel Disease. Abstract 168.
Van Immerseel et al., Butyric acid-producing anaerobic bacteria as a novel probiotic treatment approach for inflammatory bowel disease. J Med Microbiol. Feb. 2010;59(Pt 2):141-3. doi: 10.1099/jmm.0.017541-0. Epub Nov. 26, 2009.
Van't Land et al., Regulatory T-cells have a prominent role in the immune modulated vaccine response by specific oligosaccharides. Vaccine. Aug. 9, 2010;28(35):5711-7. doi: 10.1016/j.vaccine.2010.06.046. Epub Jun. 26, 2010.
Wang et al., Analysis of the germination of individual Clostridium perfringens spores and its heterogeneity. J Appl Microbiol. Nov. 2011;111(5):1212-23. doi:10.1111/j.1365-2672.2011.05135.x. Epub Sep. 14, 2011.
Zhang et al., Therapeutic effects of Clostridium butyricum on experimental colitis induced by oxazolone in rats. World J Gastroenterol. Apr. 21, 2009;15(15):1821-8.
International Search Report dated Dec. 14, 2011for PCT/JP2011/063302.
Atarashi et al., "Microbiotal influence on T cell subset development" *Seminars in Immunology*. Apr. 4, 2011;23(2):146-153.
Atarashi et al., "Induction of Colonic Regulatory T Cells by Indigenous *Clostridium* Species." *Science*. Jan. 21, 2011; 331(6015): 337-341.
Gaboriau-Routhiau et al., "The key role of segmented filamentous bacteria in the coordinated maturation of gut helper T cell responses." *Immunity*. Oct. 16, 2009;31(4):677-89.
Itoh et al., "Characterization of clostridia isolated from faeces of limited flora mice and their effect on caecal size when associated with germ-free mice." *Lab Anim*. Apr. 1985;19(2):111-8.
Kamanaka et al., "Expression of interleukin-10 in intestinal lymphocytes detected by an interleukin-10 reporter knockin tiger mouse." *Immunity*. Dec. 2006;25(6):941-52.

(56) References Cited

OTHER PUBLICATIONS

Karimi et al., "Lactobacillus reuteri-induced regulatory T cells protect against an allergic airway response in mice." *Am J Respir Crit Care Med*. Feb. 1, 2009;179(3):186-93.

Liu et al., "Reclassification of *Clostridium coccoides, Ruminococcus hansenii, Ruminococcus hydrogenotrophicus, Ruminococcus luti, Ruminococcus productus* and *Ruminococcus schinkii* as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces." *Int J Syst Evol Microbiol*. Aug. 2008;58(Pt 8):1896-902.

Mandalari et al., "In vitro evaluation of the prebiotic properties of almond skins (*Amygdalus communis* L.)." *FEMS Microbiol Lett*. Mar. 2010;304(2):116-22.

Shen et al., "Molecular profiling of the Clostridium leptum subgroup in human fecal microflora by PCR-denaturing gradient gel electrophoresis and clone library analysis." *Appl Environ Microbiol*. Aug. 2006;72(8):5232-8.

Sokol et al., "Faecalibacterium prausnitzii is an anti-inflammatory commensal bacterium identified by gut microbiota analysis of Crohn disease patients." *Proc Natl Acad Sci U S A*. Oct. 28, 2008;105(43):16731-6.

Tanoue et al., "Immune responses to gut microbiota-commensals and pathogens" *Gut Microbes*. Jul.-Aug. 2010; 1(4): 224-233.

International Search Report and Written Opinion for International Application No. PCT/JP2012/007687 dated Feb. 12, 2013.

Li et al., "Effect of oral feeding with clostridium leptum on regulatory T-cell responses and allergic airway inflammation in mice" *Ann. Allergy Asthma Immunol*. 109 (2012) 201-207.

Chandrasekaran, "Clostridium difficile Toxin B blocks effector T cells proliferation by inhibiting PLD signaling" *J. Immunology*, Apr. 2010, vol. 184, No. 1.

Sydora et al. "CD4+CD25+ Regulatory T Cells Have Divergent Effects on Intestinal Inflammation in IL-10 Gene-Deficient Mice" *Dig Dis Sci*. Jun. 2008;53(6):1544-52.

COMPOSITION FOR INDUCING PROLIFERATION OR ACCUMULATION OF REGULATORY T CELLS

RELATED APPLICATIONS

This application is a continuation of U.S. application Ser. No. 13/701,467, filed Feb. 11, 2013, which is a national stage filing under 35 U.S.C. 371 of International Application PCT/JP2011/063302 filed Jun. 3, 2011, which claims the benefit of and priority to JP2010-129134 filed Jun. 4, 2012 and PCT/JP2010/0171746 filed Dec. 3, 2010. The entire teachings of the referenced applications are incorporated by reference herein.

TECHNICAL FIELD

The present invention relates to a composition which has an effect of inducing proliferation or accumulation of regulatory T cells, and which comprises, as an active ingredient, bacteria belonging to the genus *Clostridium*, a physiologically active substance derived from the bacteria, bacterial spores, or the like. The present invention also relates to a method for inducing proliferation or accumulation of regulatory T cells, as well as a method for inhibiting such proliferation or accumulation. Moreover, the present invention relates to a vaccine composition containing at least one strain of bacteria belonging to the genus *Clostridium* or a spore of bacteria, as well as a method for treating or preventing at least one disease or condition selected from infectious diseases and autoimmune diseases by administering the vaccine composition to an individual in need thereof. The present invention also relates to a method for screening for a compound that promotes proliferation or accumulation of regulatory T cells, as well as a non-human mammal which is used in this method, and in which a reporter gene is expressed under control of IL-10 gene expression.

BACKGROUND ART

Hundreds of species of commensal microorganisms are harbored in gastrointestinal tracts of mammals, and intimately interact with the host immune systems. Results of researches using germ-free (GF) animals have shown that the commensal microorganisms exert great influences on the development of mucosal immune systems such as histogenesis of Peyer's patches (PPs) and isolated lymphoid follicles (ILFs), secretion of antimicrobial peptides from epithelium, and accumulation of unique lymphocytes in mucosal tissues, the unique lymphocytes including immunoglobulin A-producing plasma cells, intraepithelial lymphocytes, IL-17-producing CD4-positive T cells (Th 17), and IL-22-producing NK-like cells (Non-Patent Documents 1 to 7). Consequently, the presence of intestinal bacteria enhances protective functions of the mucous membranes, providing the hosts with robust immune responses against pathogenic microbes invading the bodies. On the other hand, the mucosal immune systems maintain unresponsiveness to dietary antigens and harmless microbes (Non-Patent Document 3). For this reason, abnormality in the regulation of cross-talk between commensal bacteria and an immune system (intestinal dysbiosis) may lead to overly robust immune response to environmental antigens, so that inflammatory bowel disease (IBD) is caused (Non-Patent Documents 8 to 10)

Results of Recent studies have shown that individual commensal bacteria control differentiation of their specific immune cells in the mucosal immune system. For example, *Bacteroides fragilis*, which is a commensal bacterium in humans, specifically induces a systemic Th1 cell response and a mucosal IL-10-producing T cell response in mice, and plays a role in protecting the host from colitis, which would otherwise be caused by a pathogen (Non-Patent Document 3). Segmented filamentous bacteria, which are intestinal commensal bacteria in mice, are shown to induce mucosal Th17 cell response and thereby to enhance resistance against infection of gastrointestinal tracts of the host with a pathogen (Non-Patent Documents 11 to 13). In addition, short-chain fatty acids derived from several commensal bacteria are known to suppress intestinal inflammation (Non-Patent Document 14). Moreover, it is presumed that the presence of some species of intestinal microbiota exerts a great influence on the differentiation of regulatory T cells (hereafter referred to as "Treg cells") which maintain homeostasis of the immune system.

Meanwhile, regulatory T cells which have been identified as a subset suppressing immunity are $CD4^+$ T cells in which a transcription factor Foxp3 is expressed, and are known to play an important role in maintaining immunological homeostasis (Non-Patent Documents 8, 9, 15, and 16). Moreover, it has been known that the Foxp3-expressing cells are present in a large number especially in the colon, and only Treg cells present locally in the colon constantly expresses IL-10, which is an immunosuppressive cytokine, at a high level (Non-Patent Document 17). It is also known that animals having $CD4^+$ $Foxp3^+$ cells from which IL-10 is specifically removed develop inflammatory bowel disease (Non-Patent Document 18).

Accordingly, if the mechanism of the induction of Treg cells which produce IL-10 in the colon at a high level is elucidated, immunosuppression can be enhanced, which in turn can be applied to treatment of autoimmune diseases such as inflammatory bowel disease, as well as to organ transplantation.

However, mechanisms of how a large number of Treg cells come to be present in the colon and how the Treg cells produce IL-10 in the colon at a high level are still unclear. Moreover, it is also still unclear what species of bacteria constituting the intestinal commensal bacterial flora exerts the influence on the induction of regulatory T cells.

CITATION LIST

Non Patent Literature

[NPL 1] J. J. Cebra, "Am J Clin Nutr", May, 1999, 69, 1046S

[NPL2] A. J. Macpherson, N. L. Harris, "Nat Rev Immunol", June 2004, 4, 478

[NPL 3] J. L. Round, S. K. Mazmanian, "Nat Rev Immunol", May 2009, 9, 313

[NPL 4] D. Bouskra et al., "Nature", Nov. 27, 2008, 456, 507

[NPL 5] K. Atarashi et al., "Nature", Oct. 9, 2008, 455, 808

[NPL 6] Ivanov, II et al., "Cell Host Microbe", Oct. 16, 2008, 4, 337

[NPL 7] S. L. Sanos et al., "Nat Immunol", January 2009, 10, 83

[NPL 8] M. A. Curotto de Lafaille, J. J. Lafaille, "Immunity", May 2009, 30, 626

[NPL 9] M. J. Barnes, F. Powrie, "Immunity", Sep. 18, 2009, 31, 401

[NPL 10] W. S. Garrett et al., "Cell", Oct. 5, 2007, 131, 33

[NPL 11] Ivanov, II et al., "Cell", Oct. 30, 2009, 139, 485.

[NPL 12] V. Gaboriau-Routhiau et al., "Immunity", Oct. 16, 2009, 31, 677

[NPL 13] N. H. Salzman et al., "Nat Immunol", 11, 76.

[NPL 14] K. M. Maslowski et al., "Nature", Oct. 29, 2009, 461, 1282

[NPL15] L. F. Lu, A. Rudensky, "Genes Dev", Jun. 1, 2009, 23, 1270

[NPL 16] S. Sakaguchi, T. Yamaguchi, T. Nomura, M. Ono, "Cell", May 30, 2008, 133, 775

[NPL 17] C. L. Maynard et al., "Nat Immunol", September 2007, 8, 931

[NPL 18] Y. P. Rubtsov et al., "Immunity", April 2008, 28, 546

SUMMARY OF INVENTION

Technical Problem

The present invention has been made in view of the above-described problems of the conventional techniques. Accordingly, an object of the present invention is to identify intestinal commensal bacteria which induce the proliferation or accumulation of regulatory T cells. Another object of the present invention is to provide compositions or the like which comprise the identified intestinal commensal bacteria or a physiologically active substance derived therefrom, and which thus have induce the proliferation or accumulation of regulatory T cells (Treg cells).

Solution to Problem

The present inventors have made earnest studies to solve the above-described problems. As a result, the present inventors have found that a chloroform-treated fraction and a spore-forming fraction of a fecal sample obtained from a mammal induces accumulation of regulatory T cells (Treg cells) in the colon. Moreover, the present inventors have found that bacteria belonging to the genus *Clostridium* induce proliferation or accumulation of regulatory T cells in the colon. The present inventors have also found that the regulatory T cells induced by these bacteria suppress proliferation of effector T cells. Furthermore, the present inventors have also found that colonization of bacteria belonging to the genus *Clostridium* and resultant proliferation or accumulation of Treg cells regulate local and systemic immune responses.

From these findings, the present inventors have found that the use of bacteria belonging to the genus *Clostridium*, spores thereof, or a physiologically active substance derived therefrom makes it possible to induce the proliferation or accumulation of regulatory T cells (Treg cells), and further to suppress immune functions.

More specifically, the present invention has the following aspects:

(1) A composition that induces proliferation or accumulation of regulatory T cells, the composition comprising, as an active ingredient, at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

(2) The composition according to claim 1, wherein the regulatory T cells are transcription factor Foxp3-positive regulatory T cells or IL-10-producing regulatory T cells.

(3) The composition according to any one of (1) and (2), wherein the composition has an immunosuppressive effect.

(4) The composition according to any one of (1) to (3), wherein the composition is a pharmaceutical composition.

(5) A method for inducing proliferation or accumulation of regulatory T cells in an individual (e.g., an individual in need thereof, such as an individual in need of induction of proliferation or accumulation of regulatory T cells), the method comprising a step of administering, to the individual, at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

(6) A method for inducing proliferation or accumulation of regulatory T cells in an individual (e.g., an individual in need thereof, such as an individual in need of induction of proliferation or accumulation of regulatory T cells), the method comprising a step of administering an antibiotic against Gram-negative bacteria to the individual. And the antibiotic can be administered alone or in combination with at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

(7) A method for inducing proliferation or accumulation of regulatory T cells in an individual, the method comprising a step of administering, to the individual, at least one substance selected from the group consisting of almond skin, inulin, oligofructose, raffinose, lactulose, pectin, hemicellulose, amylopectin, acetyl-Co A, biotin, beet molasses, yeast extracts, and resistant starch.

(8) The method according to any one of (5) to (7), wherein a therapeutic composition is further administered to the individual.

Note that, the "therapeutic composition" here is meant to be something other than (a)-(c) described in (5) and (6), the antibiotic against Gram-negative bacteria described in (6), or the substances described in (7).

(9) The method according to (8), wherein the therapeutic composition is at least one composition selected from the group consisting of corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, and combinations thereof.

(10) The method according to anyone of (5) to (9), wherein one measurement selected from the group consisting of promotion of IL-10 expression, promotion of CTLA4 expression, promotion of IDO expression, and suppression of IL-4 expression is used as an index of the induction of proliferation or accumulation of regulatory T cells in the individual.

(11) A method for inhibiting proliferation or accumulation of regulatory T cells in an individual (e.g., an individual thereof), the method comprising a step of administering an antibiotic against Gram-positive bacteria to the individual.

(12) The composition according to anyone of (5) to (11), wherein the regulatory T cells are transcription factor Foxp3-positive regulatory T cells or IL-10-producing regulatory T cells.

(13) A vaccine composition comprising at least one substance selected from the group consisting of the following (a) to (c):

(a) bacteria belonging to the genus *Clostridium;*

(b) a spore of bacteria in a spore-forming fraction of a fecal sample obtained from a mammal; and (c) bacteria in a chloroform-treated fraction of a fecal sample obtained from a mammal.

(14) A method for treating aiding in treating, reducing the severity of, or preventing at least one disease selected from infectious diseases and autoimmune diseases in an individual (e.g., an individual in need thereof, such as an individual in need of treatment, reduction in the severity of or prevention of at least one such disease), the method comprising administering the vaccine composition according to (13) to the individual.

(15) A method for screening for a compound having an activity to promote proliferation or accumulation of regulatory T cells, the method comprising:

(I) preparing a test substance from at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

(II) preparing non-human mammals in which a reporter gene is to be expressed under control of IL-10 gene expression;

(III) bringing the test substance into contact with the non-human mammal;

(IV) after the contact with the test substance, detecting cells expressing the reporter gene in a $CD4^+$ $Foxp3^+$ cell group of the non-human mammal, and determining the number of cells in the $CD4^+$ $Foxp3^+$ cell group expressing the reporter gene or a ratio of cells in the $CD4^+$ $Foxp3^+$ cell group expressing the reporter gene to cells in the $CD4^+$ $Foxp3^+$ cell group not expressing the reporter gene;

(V) detecting cells expressing the reporter gene in a $CD4^+$ $Foxp3^+$ cell group of the non-human mammal which has not been in contact with the test substance, and determining the number of cells in the $CD4^+$ $Foxp3^+$ cell group expressing the reporter gene or a ratio of cells in the $CD4^+$ $Foxp3^+$ cell group expressing the reporter gene to cells in the $CD4^+$ $Foxp3^+$ cell group not expressing the reporter gene; and (VI) comparing the number or the ratio determined in (IV) with the number or the ratio determined in (V), and determining, when the number or the ratio determined in (IV) is greater than that determined in (V), that the test substance is a compound that promotes proliferation or accumulation of Treg cells.

(16) A non-human mammal which is used for the method according to (15), and in which the reporter gene is expressed under the control of the IL-10 gene expression.

(17) A method for isolating, from a sample of bacteria belonging to the genus *Clostridium*, a compound having an activity to promote proliferation or accumulation of regulatory T cells, the method comprising (I) to (III):

(I) preparing a genomic DNA from the sample of bacteria belonging to the genus *Clostridium;*

(II) inserting the genomic DNA into a cloning system, and preparing a gene library derived from the sample of bacteria belonging to the genus *Clostridium*; and (III) isolating a compound having an activity to promote proliferation or accumulation of regulatory T cells, by use of the gene library obtained in step (II).

(18) A method of treatment comprising (I) to (III):

(I) measuring the percentage and/or absolute amounts of *Clostridium* Clusters IV and XIV in the microbiota of a subject;

(II) comparing them to the same measurements in a healthy individual; and (III) administering a substance to the subject, if a statistically significant decrease in the number/amounts of *Clostridium* cluster IV, XIV in the subject compared to the healthy individual is detected, wherein the substance is at least one substance selected from the group consisting of the following (a) to (c):

(a) the substance according to anyone of claims 1 to 4;

(b) an antibiotic against Gram-negative bacteria; and (c) the substance according to claim 7.

(19) A method of monitoring, comprising (I) to (II):

(I) measuring level of *Clostridium* cluster IV, XIV in a subject after administering at least one substance selected from the group consisting of the following (a) to (c):

(a) the substance according to any one of claims 1 to 4, (b) an antibiotic against Gram-negative bacteria, and (c) the substance according to claim 7; and (II) if the level increases, it is judged to be a sign that the subject is responding favorably.

Advantageous Effects of Invention

The compositions of the present invention containing as an active ingredient bacteria belonging to the genus *Clostridium* or a physiologically active substance derived from the bacteria serves as an excellent composition for inducing the proliferation or accumulation of regulatory T cells (Treg cells). Immunity in a living organism can be suppressed through administration of the composition of the present invention as a pharmaceutical product or ingestion of the composition as a food or beverage. Accordingly, the composition of the present invention can be used, for example, to prevent or treat autoimmune diseases or allergic diseases, as well as to suppress immunological rejection in organ transplantation or the like. In addition, if a food or beverage such as a health food comprises the composition of the present invention, healthy individuals can ingest the composition easily and routinely. As a result, it is possible to induce the proliferation or accumulation of regulatory T cells and thereby to improve immune functions.

DESCRIPTION OF EMBODIMENTS

Figure 1:
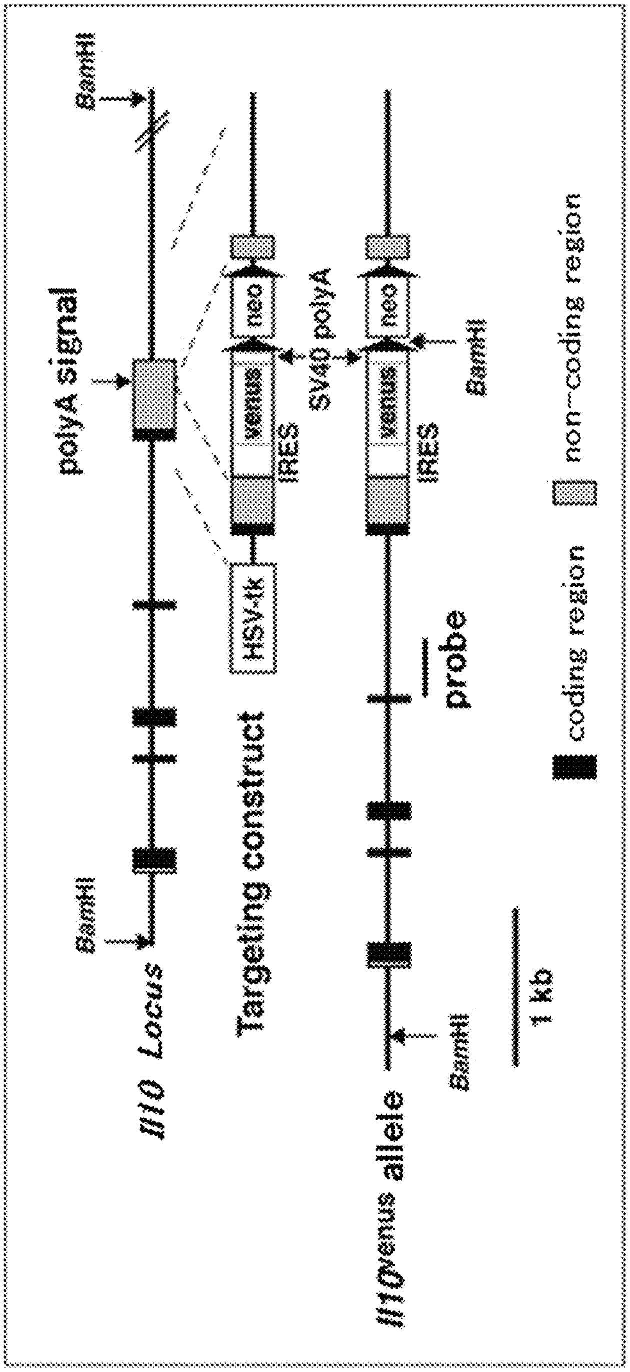
FIG. 1 is a schematic diagram showing a method of producing Il10$^{venus}$ mouse.

<Composition Having Effect of Inducing Proliferation or Accumulation of Regulatory T Cells>

The present invention provides a composition that induces proliferation or accumulation of regulatory T cells, the composition comprising, as an active ingredient, at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

In the present invention "regulatory T cells" mean T cells which have a function of suppressing an abnormal or excessive immune response, and which play a role in immune tolerance. The regulatory T cells are typically transcription factor Foxp3-positive CD4-positive T cells. However, the regulatory T cells of the present invention also include transcription factor Foxp3-negative regulatory T cells, as long as the regulatory T cells are IL-10-producing CD4-positive T cells.

The meaning of the "induces proliferation or accumulation of regulatory T cells" in the present invention includes an effect of inducing the differentiation of immature T cells into regulatory T cells, which differentiation leads to the proliferation or the accumulation of regulatory T cells. In addition, the meaning of the "induces proliferation or accumulation of regulatory T cells" in the present invention includes in-vivo effects, in vitro effects, and ex vivo effects. Accordingly, all of the following effects are included: an effect of inducing in vivo proliferation or accumulation of regulatory T cells through administration or ingestion of the bacteria belonging to the genus *Clostridium* or the physiologically active substance or the like derived from the bacteria; an effect of inducing proliferation or accumulation of cultured regulatory T cells by causing the bacteria belonging to the genus *Clostridium* or the physiologically active substance or the like derived from the bacteria to act on the cultured regulatory T cells; and an effect of inducing proliferation or accumulation of regulatory T cells which are collected from a living organism and which are intended to be subsequently introduced into a living organism, such as the organism from which they were obtained or another organism, by causing the bacteria belonging to the genus *Clostridium* or the physiologically active substance or the like derived from the bacteria to act on the regulatory T cells. The effect of inducing proliferation or accumulation of regulatory T cells can be evaluated, for example, as follows. Specifically, the bacteria belonging to the genus *Clostridium* or the physiologically active substance or the like derived from the bacteria is orally administered to an experimental animal such as a germ-free mouse, then CD4-positive cells in the colon are isolated, and the ratio of regulatory T cells contained in the CD4-positive cells is measured by flow cytometry (refer to Example 7).

The regulatory T cells of which proliferation or accumulation is induced by the composition of the present invention are preferably transcription factor Foxp3-positive regulatory T cells or IL-10-producing regulatory T cells.

The "bacteria belonging to the genus *Clostridium*," which are the active ingredient in the composition of the present invention, is not particularly limited as long as the bacteria have the effect of inducing proliferation or accumulation of regulatory T cells. The bacteria preferably belong to the cluster XIVa or the cluster IV. One strain of the bacteria alone can be used for the composition of the present invention, but two or more strains of the bacteria can be used together for the composition of the present invention. The use of multiple strains of bacteria belonging to the cluster XIVa or the cluster IV in combination can bring about an excellent effect on regulatory T cells. In addition to the bacteria belonging to these clusters, bacteria belonging to other clusters (for example, bacteria belonging to the cluster III) can also be used in combination. If more than one strain of bacteria is used (e.g., one or more strain belonging to cluster XIVa, one or more strain belonging to cluster IV, one or more strain belonging to a cluster other than cluster XIVa or cluster IV, such as one or more strain belonging to cluster III), the type and number of strains used can vary widely. The type and number to be used can be determined based on a variety of factors (e.g., the desired effect, such as induction or inhibition of proliferation or accumulation of regulatory T cells; the disease or condition to be treated, prevented or reduced in severity; the age or gender of the recipient) The strains can be present in a single composition, in which case they will be consumed or ingested together, or can be present in more than one composition (e.g., each can be in a separate composition), in which case they can be consumed individually or the compositions can be combined and the resulting combination (combined compositions) consumed or ingested. Any number or combination of strains that proves effective (e.g., any number from one to 200, such as 1 to 100, 1 to 50, 1 to 40, 1 to 30, 1 to 20, 1 to 10, 1 to 5 and any number therebetween) can be administered. In certain embodiments of the present invention, a combination of some or all of the 46 strains described in Document (Itoh, K., and Mitsuoka, T. Characterization of clostridia isolated from faeces of limited flora mice and their effect on caecal size when associated with germ-free mice. Lab. Animals 19: 111-118 (1985)) is used. For example, at least one, two or more, three, three or more, four, four or more, five, five or more, six, six or more or any other number of the 46 described strains, including 46 strains, can be used. They can be used in combination with one another and in combination with strains not described in the cited reference (e.g, in combination with one or more strains belonging to cluster III).

Note that, the cluster of "bacteria belonging to the genus *Clostridium*" can be identified, for example, as follows. Specifically, the bacteria belonging to the genus *Clostridium* are classified by PCR using a primer set consisting of SEQ ID NOs 64 and 65 (for *Clostridium* spp. belonging to the cluster XIVa) or a primer set consisting of SEQ ID NOs 66 and 67 (for *Clostridium* spp. belonging to the cluster IV) (refer to Example 18). In addition, the bacteria belonging to the genus *Clostridium* are classified by sequencing of 16S rRNA gene amplified using a primer set consisting of SEQ ID NOs 19 and 20 (refer to Example 7).

Viable cells of the bacteria belonging to the genus *Clostridium* can be used for the composition of the present invention, and killed cells thereof may also be used for the composition. In addition, from the viewpoint of stability to heat, resistance to antibiotics and the like, and long storage period, the bacteria belonging to the genus *Clostridium* are preferably in the form of spore.

The meaning of the "physiologically active substance derived from bacteria belonging to the genus *Clostridium*" of the present invention includes substances contained in the bacteria, secretion products of the bacteria, and metabolites of the bacteria. Such a physiologically active substance can be identified by purifying an active component from the bacteria, a culture supernatant thereof, or intestinal tract contents in the intestinal tract of a mouse in which only bacteria belonging to the genus *Clostridium* are colonized by an already known purification method.

The active ingredient "spore-forming fraction of a fecal sample obtained from a mammal" in the composition of the present invention is not particularly limited, as long as the fraction includes spore-forming bacteria present in feces of a mammal, and has the effect of inducing proliferation or accumulation of regulatory T cells.

The active ingredient "chloroform-treated fraction of a fecal sample obtained from a mammal" in the composition of the present invention is not particularly limited, as long as the fraction is obtained by treating feces of a mammal with chloroform (for example, 3% chloroform), and has the effect of inducing proliferation or accumulation of regulatory T cells.

Note that the "mammal" in the present invention is not particularly limited, and examples thereof include humans, mice, rats, cattle, horses, pigs, sheep, monkeys, dogs, and cats.

Meanwhile, when the "spore-forming fraction of a fecal sample obtained from a mammal" or the "chloroform-treated fraction of a fecal sample obtained from a mammal" is cultured in a medium, substances contained in the bacteria, secretion products of the bacteria, metabolites of the bacteria are released from the bacteria and the like contained in the fraction. The meaning of the active ingredient "culture supernatant of the fraction" in the composition of the present invention includes such substances, secretion products, and metabolites. The culture supernatant is not particularly limited, as long as the culture supernatant has the effect of inducing proliferation or accumulation of regulatory T cells. Examples of the culture supernatant include a protein fraction of the culture supernatant, a polysaccharide fraction of the culture supernatant, a lipid fraction of the culture supernatant, and a low-molecular weight metabolite fraction of the culture supernatant.

The composition of the present invention may be in the form of a pharmaceutical composition, a food or beverage (which may also be an animal feed), or a reagent used for an animal model experiment, the pharmaceutical composition, the food or beverage, and the reagent having the effect of inducing proliferation or accumulation of regulatory T cells. An example of the present invention revealed that regulatory T cells (Treg cells) induced by bacteria or the like belonging to the genus *Clostridium* suppressed the proliferation of effector T-cells. Accordingly, the composition of the present invention can be used suitably as a composition having an immunosuppressive effect. The immunosuppressive effect can be evaluated, for example, as follows. Specifically, regulatory T cells isolated from an experimental animal, such as a mouse, to which the composition of the present invention is orally administered are caused to act on effector T-cells ($CD4^+$ $CD25^-$ cells) isolated from the spleen, and then proliferation ability thereof is measured by using the intake amount of [$^3$H]-thymidine as an index (refer to Example 14).

The composition of the present invention can be used, for example, as a pharmaceutical composition for preventing or treating an autoimmune disease such as chronic inflammatory bowel disease, systemic lupus erythematosus, rheumatoid arthritis, multiple sclerosis, or Hashimoto's disease, or an allergic disease such as pollenosis or asthma; a pharmaceutical composition for suppressing rejection in organ transplantation or the like; a food or beverage for improving immune functions; or a reagent for suppressing the proliferation or function of effector T-cells.

More specific examples of target diseases of the composition of the present invention include autoimmune diseases, allergic diseases, and rejection in organ transplantations and the like, such as inflammatory bowel disease (IBD), ulcerative colitis, Crohn's disease, sprue, autoimmune arthritis, rheumatoid arthritis, Type I diabetes, multiple sclerosis, graft vs. host disease following bone marrow transplantation, osteoarthritis, juvenile chronic arthritis, Lyme arthritis, psoriatic arthritis, reactive arthritis, spondy loarthropathy, systemic lupus erythematosus, insulin dependent diabetes mellitus, thyroiditis,. asthma, psoriasis, dermatitis scleroderma, atopic dermatitis, graft versus host disease, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlejn purpurea, microscopic vasculitis of the kidneys, chronic active hepatitis, uveitis, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, polyglandular deficiency type I syndrome and polyglandular deficiency type II syndrome, Schmidt's syndrorme, adult (acute) respiratory distress syndrome, alopecia, alopecia areata, seronegative arthopathy, arthropathy, Reiter's disease, psoriatic arthropathy, chlamydia, yersinia and salmonella associated arthropathy, spondyloarhopathy, atheromatous disease/arteriosclerosis, atopic allergy, food allergies, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondy litis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, discoid lupus, erythematosus, male infertility idiopathic or NOS, sperm autoimmunity, multiple sclerosis (all subtypes), insulindependent diabetes mellitus, sympathetic ophthalmia, pulmonary hypertension secondary to connective tissue disease, Goodpasture's syndrome, pulmonary manifestation of polyarteritis nodosa, acute rheumatio fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, allergic rhinitis (pollen allergies), anaphylaxis, pet allergies, latex allergies, drug allergies, allergic rhinoconjuctivitis, eosinophilic esophagitis, hypereosinophilic syndrome, eosinophilic gastroenteritis cutaneous lupus erythematosus, eosinophilic esophagitis, hypereosinophilic syndrome, and eosinophilic gastroenteritis.

The composition of the present invention can also be used as a pharmaceutical composition for preventing or treating infectious diseases in an individual whose resistance to the infectious diseases is impaired because of damage due to excessive inflammation caused by the immunity.

Example of infectious pathogens which impair maintenance or recovery of homeostasis of a host, and which eventually bring about such immunopathological tissue damage include *Salmonella, Shigella, Clostridium difficile, Mycobacterium* (which cause the disease tuberculosis), protozoa (which cause the disease malaria), filarial nematodes (which cause the disease filariasis), *Schistosoma* (which cause the disease schistosomiasis), *Toxoplasma* (which cause the disease toxoplasmosis), *Leishmania* (which cause the disease leishmaniasis), HCV and HBV (which cause the disease hepatitis C and hepatitis B), and herpes simplex viruses (which cause the disease herpes).

Pharmaceutical preparations can be formulated from the composition of the present invention by already known drug formulation methods. For example, the composition of the present invention can be used orally or parenterally in the forms of capsules, tablets, pills, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like.

For formulating these preparations, the composition of the present invention can be used in appropriate combination with carriers acceptable pharmacologically or acceptable for a food or beverage, specifically, with sterile water, physiological saline, vegetable oil, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, a flavor corrigent, a solubilizer, other additives, or the like.

Meanwhile, for formulating a pharmaceutical preparation thereof, and particularly for formulating a pharmaceutical preparation for oral administration, it is preferable to use in combination a composition which enables an efficient delivery of the composition of the present invention to the colon, from the viewpoint of more efficiently inducing the proliferation or accumulation of regulatory T cells in the colon.

Such a composition or method which enables the delivery to the colon is not particularly limited, and known compositions or methods can be employed as appropriate. Examples thereof include pH sensitive compositions, more specifically, enteric polymers which release their contents when the pH becomes alkaline after the enteric polymers pass through the stomach. When a pH sensitive composition is used for formulating the pharmaceutical preparation, the pH sensitive composition is preferably a polymer whose pH threshold of the decomposition of the composition is 6.8 to 7.5. Such a numeric value range is a range where the pH shifts toward the alkaline side at a distal portion of the stomach, and hence is a suitable range for use in the delivery to the colon.

Moreover, another example of the composition enabling the delivery to the colon is a composition which ensures the delivery to the colon by delaying the release of the contents by approximately 3 to 5 hours, which corresponds to the small intestinal transit time. In an example of formulating a pharmaceutical preparation using the composition for delaying the release, a hydrogel is used as a shell. The hydrogel is hydrated and swells upon contact with gastrointestinal fluid, so that the contents are effectively released. Furthermore the delayed release dosage units include drug-containing compositions having a material which coats or selectively coats a drug. Examples of such a selective coating material include in vivo degradable polymers, gradually hydrolyzable polymers, gradually water-soluble polymers, and/or enzyme degradable polymers. A preferred coating material for efficiently delaying the release is not particularly limited, and examples thereof include cellulose-based polymers such as hydroxypropyl cellulose, acrylic acid polymers and copolymers such as methacrylic acid polymers and copolymers, and vinyl polymers and copolymers such as polyvinylpyrrolidone.

Examples of the composition enabling the delivery to the colon further include bioadhesive compositions which specifically adhere to the colonic mucosal membrane (for example, a polymer described in the specification of U.S. Pat. No. 6,368,586), and compositions into which a protease inhibitor is incorporated for protecting particularly a biopharmaceutical preparation in the gastrointestinal tracts from decomposition due to an activity of a protease.

An example of a system enabling the delivery to the colon is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

Another example of the system enabling the delivery to the colon is a system of delivering a composition to the colon, the system being specifically decomposed by an enzyme (for example, a carbohydrate hydrolase or a carbohydrate reductase) present in the colon. Such a system is not particularly limited, and more specific examples thereof include systems which use food components such as non-starch polysaccharides, amylose, xanthan gum, and azopolymers.

When used as a pharmaceutical composition, the composition of the present invention may be used in combination with an already known pharmaceutical composition for use in immunosuppression. Such a known pharmaceutical composition is not particularly limited, and may be at least one therapeutic composition selected from the group consisting of corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines (preferably vaccines used for vaccination where the amount of an allergen is gradually increased), and combinations thereof. It is preferable to use these therapeutic compositions in combination with the composition of the present invention.

When the composition of the present invention is used as a food or beverage, the food or beverage can be, for example, a health food, a functional food, a food for specified health use, a dietary supplement, a food for patients, or an animal feed. The food or beverage of the present invention can be ingested in the forms of the compositions as described above, and also can be ingested in the forms of various foods and beverages. Specific examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, and Chinese soups; soups; dairy products such as milk, dairy beverages, ice creams, cheeses, and yogurts; fermented products such as fermented soybean pastes, yogurts, fermented beverages, and pickles; bean products; various confectionery products such as Western confectionery products including biscuits, cookies, and the like, Japanese confectionery products including steamed bean-jam buns, soft adzuki-bean jellies, and the like, candies, chewing gums, gummies, cold desserts including jellies, creme caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies. The composition of the present invention can be used for animals including humans. The animals, other than humans, are not particularly limited, and the composition can be used for various livestock, poultry, pets, experimental animals, and the like. Specific examples of the animals include pigs, cattle, horses, sheep, goats, chickens, wild ducks, ostriches, domestic ducks, dogs, cats, rabbits, hamsters, mice, rats, monkeys, and the like, but the animals are not limited thereto.

Without wishing to be bound by theory, in the present invention, individuals in which the relative abundance of bacteria belonging to the group Firmicutes (the group to which the *Clostridium* clusters IV and XIVa belong) is large gain more body weight than individuals in which the relative abundance of bacteria belonging to the group Bacteroidetes is large. Accordingly, the composition of the present invention is capable of conditioning absorption of nutrients and improving feed efficiency. From such a viewpoint, the composition of the present invention can be used for promoting body weight gain, or for an animal feed good in feed efficiency.

Moreover, the addition of the composition of the present invention to an antibiotic-free animal feed makes it possible to increase the body weight of a subject that ingests the animal feed to a level equal to or higher than those achieved by antibiotic-containing animal feeds, and also makes it possible to reduce pathogenic bacteria in the stomach to a level equal to those achieved by typical antibiotic-containing animal feeds. Accordingly, the composition of the present invention can be used for an animal feed which does not need the addition of antibiotics.

In addition, unlike conventional bacteria (*Lactobacillus* and *Bifidobacteria*) in commercial use which are not easy to incorporate into the livestock production, the composition of the present invention in the spore form can be pelletized, sprayed, or easily mixed with an animal feed, and also can be added to drinking water.

The feeding of such an animal feed using the composition of the present invention is not particularly limited, and the animal feed may be fed to a subject at regular intervals in a selective manner, or may be fed for a certain period (for example, at its birth, during weaning, or when the subject to be fed is relocated or shipped).

Moreover, from the above-described viewpoint, the composition of the present invention can be preferably used for malnourished humans. In other words, also when the subject who ingests the composition is a human, the composition of the present invention can preferably be used for promoting the body weight gain, and enhancing the energy absorption from foods.

The food or beverage of the present invention can be manufactured by a manufacturing technique which is well known in the technical field. To the food or beverage, one or more components (for example, a nutrient) which are effective for the improvement of an immune function by the immunosuppressive effect may be added. In addition, the food or beverage may be combined with another component or another functional food exhibiting a function other than the function of the improvement of an immune function to thereby serve as a multi-functional food or beverage.

Moreover, the composition of the present invention can be preferably incorporated into foods requiring a processing step which may destroy ordinary probiotic strains. Specifically, most commercially usable probiotic strains cannot be incorporated into foods which need to be processed by any one of a heat treatment, long term storage, a freezing treatment, a mechanical stress treatment, and a high-pressure treatment (for example, extrusion forming or roll forming). On the other hand, because of an advantageous nature of forming spores, the composition of the present invention can be easily incorporated into such processed foods.

For example, the composition of the present invention in the form of spore can survive even in a dried food, and can remain living even after being ingested. Likewise, the composition of the present invention can withstand low-temperature sterilization processes, typically processes at a temperature in a range from 70° C. to the boiling point, both inclusive. Thus, the composition of the present invention can be incorporated into all kinds of dairy products. Furthermore, the composition of the present invention can withstand long-term storage of many years; high-temperature processing such as baking and boiling; low-temperature processing such as freezing and cold storage; and high-pressure treatments such as extrusion forming and roll forming.

The foods which need to be processed under such harsh conditions are not particularly limited, and examples thereof include foods which need to be processed in a microwave oven to be edible (for example, oatmeal), foods which need to be baked to be edible (for example, muffin), foods which need to be subjected to a sterilization high-temperature treatment for a short period of time to be edible (for example, milk), and foods which need to be heated to be drinkable (for example, hot tea).

When the composition of the present invention is administered or ingested, the amount thereof for the administration or ingestion is selected as appropriate depending on the age, body weight, symptoms, health conditions, of a subject, the kind of the composition (a pharmaceutical product, a food or beverage, or the like), and the like. For example, the amount per administration or ingestion is generally 0.01 mg/kg body weight to 100 mg/kg body weight, and preferably 1 mg/kg body weight to 10 mg/kg body weight. The present invention also provides a method for suppressing the immunity of a subject, the method being characterized in that the bacteria belonging to the genus *Clostridium* or the physiologically active substance derived from the bacteria is administered into or ingested by the subject as described above.

A product of the composition of the present invention (a pharmaceutical product, a food or beverage, or a reagent) or a manual thereof may be provided with a note stating that the product can be used to suppress the immunity (including a note stating that the product has an immunosuppressive effect, and a note stating that the product has an effect of suppressing the proliferation or function of effector T-cells). Here, the "provision to the product or the manual thereof with the note" means that the note is provided to a main body, a container, a package, or the like of the product, or the note is provided to a manual, a package insert, a leaflet, or other printed matters, which disclose information on the product.

<Method for Inducing Proliferation or Accumulation of Regulatory T Cells>

As described above, and as will be shown in Examples, the administration of the composition of the present invention to an individual makes it possible to induce proliferation or accumulation of regulatory T cells in the individual. Thus, the present invention can provides a method for inducing proliferation or accumulation of regulatory T cells in an individual, the method comprising a step of administering, to the individual, at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

Note that, the "individual" in the present invention is not particularly limited, and examples thereof include humans, various kinds of livestock, poultry, pets, experimental animals, and the like. The "individual" may be in a healthy state or a diseased state.

Moreover, as will be shown in Example 5 to be described later, Gram-positive commensal bacteria play principal roles in the proliferation or accumulation of regulatory T cells. Accordingly, the present invention can also provide a method for inducing proliferation or accumulation of regulatory T cells in an individual, the method comprising a step of administering an antibiotic against Gram-negative bacteria to the individual.

In the present invention, the "antibiotic against Gram-negative bacteria" is not particularly limited, and examples thereof include aminoglycoside antibiotics (amikacin, gentamicin, kanamycin, neomycin, netilmicin, tobramycin, and paromomycin), cephalosporin antibiotics (cefaclor, cefamandole, cefoxitin, cefprozil, cefuroxime, cefixime, cefdinir, cefditoren, cefoperazone, cefotaxime, ceftazidime, ceftibuten, ceftizoxime, ceftriaxone, and cefoxotin), sulfonamides, ampicillin, and streptomycin. Without wishing to be bound by theory, the "antibiotic against Gram-negative bacteria" according to the present invention is preferably one which reduces Gram-negative bacteria, and contributes to the colonization of Gram-positive bacteria.

Moreover, a prebiotic composition such as almond skin, inulin, oligofructose, raffinose, lactulose, pectin, hemicellulose (such as xyloglucan and alpha-glucans), amylopectin, and resistant starch which are not decomposed in the upper gastrointestinal tract and promote the growth of intestinal microbes in the intestinal tract, as well as growth factors such as acetyl-Co A, biotin, beet molasses, and yeast extracts, contribute to the proliferation of bacteria belonging to the genus *Clostridium*. Accordingly, the present invention can also provide a method for inducing proliferation or accumulation of regulatory T cells in an individual, the method comprising a step of administering, to the individual, at least one substance selected from the group consisting of these substances.

Meanwhile, in the "method for inducing proliferation or accumulation of regulatory T cells" of the present invention, the composition of the present invention, the above-described "antibiotic against Gram-negative bacteria," and the above-described "prebiotic composition or growth factor" may be used in combination. Such combined use is not particularly limited, and examples of the combined use are as follows: the "antibiotic against Gram-negative bacteria" is administered to an individual in advance, and then the composition of the present invention is administered; the "antibiotic against Gram-negative bacteria" and the composition of the present invention are simultaneously administered to an individual; the "prebiotic composition or growth factor" is administered to an individual in advance, and then the composition of the present invention is administered; the "prebiotic composition or growth factor" and the composition of the present invention are simultaneously administered to an individual; the composition of the present invention, the "antibiotic against Gram-negative bacteria," and the "prebiotic composition or growth factor" are administered to an individual simultaneously or individually at any appropriate time.

Moreover, a therapeutic composition may be administered to an individual together with at least one substance selected from the group consisting of the composition of the present invention, the "antibiotic against Gram-negative bacteria," and the "prebiotic composition or growth factor."

Such a therapeutic composition is not particularly limited, and may be at least one therapeutic composition selected from the group consisting of corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines (preferably, vaccines used for vaccination where the amount of an allergen is gradually increased), and combinations thereof. It is preferable to use these therapeutic compositions in combination with the above-described substance.

Moreover, there is no particular limitation imposed on the combined use of the therapeutic composition with at least one substance selected from the group consisting of the composition of the present invention, the "antibiotic against Gram-negative bacteria," and the "prebiotic composition or growth factor". For example, the "one substance" and the therapeutic composition are administered orally or parenterally to an individual simultaneously or individually at any appropriate time.

Moreover, in the above-described "method for inducing proliferation or accumulation of regulatory T cells," whether or not the administration of the composition of the present invention or the like actually induces the proliferation or accumulation of regulatory T cells can be determined by using, as an index, increase or reinforcement of at least one selected from the group consisting of the number of regulatory T cells, the ratio of regulatory T cells in the T cell group of the colon, a function of regulatory T cells, and expression of a marker of regulatory T cells. It is preferable to use one measurement selected from the group consisting of promotion of IL-10 expression, promotion of CTLA4 expression, promotion of IDO expression, and suppression of IL-4 expression, as the index of the induction of proliferation or accumulation of regulatory T cells.

Note that examples of a method for detecting such expression include the northern blotting, the RT-PCR, and the dot blotting for detection of gene expression at the transcription level; and the ELISA, the radioimmunoassay, the immunoblotting, the immunoprecipitation, and the flow cytometry for detection of gene expression at the translation level.

Meanwhile, a sample used for measuring such an index is not particularly limited, and examples thereof include blood sampled from an individual and tissue pieces obtained in a biopsy.

<Method for Predicting Response of Individual to Composition of Present Invention and/or Prognosis of Individual>

The present invention can provide a method in which the absolute amount or the ratio of bacteria belonging to the genus *Clostridium* in a microbiota of an individual is determined, and, when the ratio or the absolute value of the bacteria belonging to the genus *Clostridium* is reduced in comparison with a base line value obtained by performing a similar determination on an individual in a typical health state, it is determined that the individual is possibly responsive to the composition of the present invention.

In one embodiment, a method to predict a subject's response to a substance and/or the subject's prognosis is provided. The method comprises measuring the percentage or absolute amounts of *Clostridium* clusters IV and XIV in the microbiota of the subject and comparing them to a baseline value of the same measurements in a prototypical healthy subject, wherein a decreased absolute amount or percentage level of *Clostridium* clusters IV and/or XIV indicates that the subject may respond favorably to the compositions of the invention.

In one embodiment, the method further comprises measuring the composition of the microbiota of the subject after administration of the substance, wherein an increase in the percentage or absolute number of *Clostridium* spp. belonging to clusters IV, XIV after administration of the compositions of the present invention relative to prior to the administering is a positive indicator of enhanced immunosuppression (or immunoregulation). The measurement of the composition of the subject's microbiota can be made with techniques known in the art, such as 16srRNA sequencing.

Note that, in these embodiments, the substance is at least one substance selected from the group consisting of the following (a) to (e):

(a) bacteria belonging to the genus *Clostridium* or a physiologically active substance derived from the bacteria;
(b) a spore-forming fraction of a fecal sample obtained from a mammal or a culture supernatant of the fraction;
(c) a chloroform-treated fraction of a fecal sample obtained from a mammal or a culture supernatant of the fraction;
(d) an antibiotic against Gram-negative bacteria according to the present invention; and
(e) at least one substance selected from the group consisting of almond skin, inulin, oligofructose, raffinose, lactulose, pectin, hemicellulose (such as xyloglucan and alpha-glucans), amylopectin, acetyl-Co A, biotin, beet molasses, yeast extracts, and resistant starch.

<Method for Inhibiting Proliferation or Accumulation of Regulatory T Cells>

As will be shown in Example 5 to be described later, Gram-positive commensal bacteria have principal roles in the proliferation or accumulation of regulatory T cells. Accordingly, the present invention can also provide a method for inhibiting proliferation or accumulation of regulatory T cells in an individual, the method comprising a step of administering an antibiotic against Gram-positive bacteria to the individual.

In the present invention, the "antibiotic against Gram-positive bacteria" is not particularly limited, and examples thereof include cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

As described above, the "individual" in the present invention is not particularly limited, and examples thereof include humans, various kinds of livestock, poultry, pets, experimental animals, and the like. The "individual" may be in a healthy state or a diseased state. Such a diseased state is not particularly limited, and examples thereof include states of being subjected to cancer immunotherapy and of suffering from an infectious disease.

Moreover, as another mode of the "method for inhibiting proliferation or accumulation of regulatory T cells," the present invention can provide a method for inhibiting proliferation or accumulation of regulatory T cells in an individual, the method comprising a step of administering, to the individual, any one of an antibody, an antibody fragment, and a peptide, which are against an antigen that is at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

<Vaccine Composition and Method for Treating or Preventing Infectious Disease or Autoimmune Disease by Using the Vaccine Composition>

As described above, and as will be shown in Example 15 to be described later, the induction of Treg cells in the colon by the *Clostridium* has an important role in local and systemic immune responses. Accordingly, the present invention can also provide a "vaccine composition comprising at least one substance selected from the group consisting of the following (a) to (c): (a) bacteria belonging to the genus *Clostridium*; (b) a spore of bacteria in a spore-forming fraction of a fecal sample obtained from a mammal; and (c) bacteria in a chloroform-treated fraction of a fecal sample obtained from a mammal" and a "method for treating, aiding in treating, reducing the severity of, or preventing at least one disease selected from infectious diseases and autoimmune diseases in an individual, the method comprising administering the vaccine composition to the individual."

Note that such "autoimmune diseases" are not particularly limited, and examples thereof include those described as the "specific examples of target diseases" in <Composition Having Effect of Inducing Proliferation or Accumulation of Regulatory T cells>. The "infectious diseases" are also not particularly limited, and examples thereof include infectious diseases associated with "infectious pathogens" described as the "example of infectious pathogens" in <Composition Having Effect of Inducing Proliferation or Accumulation of Regulatory T cells>.

<Method for Screening for Compound Having Activity to Promote Proliferation or Accumulation of Regulatory T Cells>

The present invention can also provide a method for screening for a compound having an activity to promote proliferation or accumulation of regulatory T cells, the method comprising:

(1) preparing a test substance from at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

(2) preparing non-human mammals in which a reporter gene is to be expressed under control of IL-10 gene expression;

(3) bringing the test substance into contact with the non-human mammal;

(4) after the contact with the test substance, detecting cells expressing the reporter gene in a $CD4^+$ $Foxp3^+$ cell group of the non-human mammal, and determining the number of cells in the $CD4^+$ $Foxp3^+$ cell group expressing the reporter gene or a ratio of cells in the $CD4^+$ $Foxp3^+$ cell group expressing the reporter gene to cells in the $CD4^+$ $Foxp3^+$ cell group not expressing the reporter gene;

(5) detecting cells expressing the reporter gene in a $CD4^+$ $Foxp3^+$ cell group of the non-human mammal which has not been in contact with the test substance, and determining the number of cells in the $CD4^+$ $Foxp3^+$ cell group expressing the reporter gene or a ratio of cells in the $CD4^+$ $Foxp3^+$ cell group expressing the reporter gene to cells in the $CD4^+$ $Foxp3^+$ cell group not expressing the reporter gene; and (6) comparing the absolute numbers or the ratios determined in steps (4) with the number or the ratio determined in (5), and determining, when the number or the ratio determined in (4) is greater than that determined in (5), that the test substance is a compound that promotes proliferation or accumulation of Treg cells.

The "test substance" according to the present invention is not particularly limited, as long as the test substance is a substance prepared from at least one substance selected from the group consisting of the substances (a) to (c). Examples of the test substance include proteins, polysaccharides, lipids, and nucleic acids which are derived from at least one substance selected from the group consisting of the above described substances (a) to (c).

The "non-human mammal in which a reporter gene is to be expressed under control of IL-10 gene expression" according to the present invention is not particularly limited, as long as the non-human mammal is a non-human mammal having a reporter gene whose expression is controlled by an IL-10 gene expression control region (for example, a promoter, or an enhancer). Examples of such a reporter gene include genes encoding fluorescent proteins (for example, GFP), and genes encoding luciferase. As the "non-human mammal in which a reporter gene is to be expressed under control of IL-10 gene expression" according to the present invention, an $Il10^{venus}$ mouse to be shown later in Examples can be preferably used.

The "contact" according to the present invention is not particularly limited, and examples thereof include administration of the test substance to the non-human mammal orally or parenterally (for example, intraperitoneal injection, or intravenous injection).

The present invention can also provide a non-human mammal which is used for the method, and in which the reporter gene is to be expressed under the control of the IL-10 gene expression.

Furthermore, the present invention can also provide a method for isolating, from a sample of bacteria belonging to the genus *Clostridium*, a compound having an activity to promote proliferation or accumulation of regulatory T cells, the method comprising the following steps (1) to (3):

(1) preparing a genomic DNA from the sample of bacteria belonging to the genus *Clostridium;*

(2) inserting the genomic DNA into a cloning system, and preparing a gene library derived from the sample of bacteria belonging to the genus *Clostridium*; and (3) isolating a compound having an activity to promote proliferation or accumulation of regulatory T cells, by use of the gene library obtained in step (2).

In such steps, methods for the preparation and the isolation are not particularly limited, and known techniques for an in-vitro or in-vivo system can be used as appropriate. Moreover, the compound isolated by this method is not particularly limited, and examples thereof include nucleic acids (for example, a DNA, a mRNA, and a rRNA) derived from bacteria belonging to the genus *Clostridium*, as well as polypeptides and proteins derived from the bacteria belonging to the genus *Clostridium*.

<Other Embodiment Modes According to Present Invention>

In addition to the above-described embodiment modes, the present invention can also provide the following embodiment modes.

Specifically, the present invention can also provide a method for determining the composition of a microbiota in an individual, wherein the increase in the ratio or the absolute number of bacteria belonging to the genus *Clostridium* after the administration of the composition of the present invention to the individual with respect to the ratio or the absolute number before the administration is used as an index of increased immunosuppression. In such a method, the method for determining the composition of the microbiota is not particularly limited, and known techniques (for example, 16S rRNA sequencing) can be used as appropriate.

The present invention can also provide a method for measuring differentiation of Treg cells, wherein the increase in differentiation of Treg cells in an individual after administration of the composition of the present invention to the individual with respect to that before the administration is used as an index of increased immunosuppression (or immunoregulation).

Moreover, the composition of the present invention can also be administered to an individual under an antibiotic treatment. The timing of the administration is not particularly limited, and the composition of the present invention can be administered before or simultaneously with the antibiotic treatment, for example. Meanwhile, the composition of the present invention is preferably administered in the spore form from the viewpoint of resistance to antibiotics.

Moreover, in a preferred mode of such administration, the composition of the present invention is administered after or simultaneously with administration of an antibiotic against Gram-positive bacteria, for example. Note that such an "antibiotic against Gram-positive bacteria" is not particularly limited, and examples thereof include cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

Meanwhile, in another preferred mode of such administration, the composition of the present invention is administered after (or simultaneously with) a treatment using vancomycin, metronidazole, linezolid, ramoplanin, or fidaxomicin, for example.

EXAMPLES

Hereinafter, the present invention is described more specifically on the basis of Examples. However, the present invention is not limited to Examples below.

Note that mice used in Examples were prepared or produced as follows. In the following description, mice may be referred to with "SPF" or "GF" attached in front thereof. These "SPF" and "GF" indicate that the mice were maintained in the absence of specific pathogenic bacteria (specific pathogen-free, SPF), and that the mice were maintained under Germ-Free (GF) conditions, respectively.

<Mice>

C57BL/6, Balb/c, and IQI mice maintained under SPF or GF conditions were purchased from Sankyo Labo Service Corporation, Inc. (Japan), JAPAN SLC, INC. (Japan), CLEA Japan, Inc. (Japan), or The Jackson Laboratory (USA). GF mice and gnotobiotic mice were bread and maintained within the gnotobiotic facility of The University of Tokyo, Yakult Central Institute for Microbiological Research, or Sankyo Labo Service Corporation, Inc. $Myd88^{-/-}$, $Rip2^{-/-}$, and $Card9^{-/-}$ mice were produced as described in Non-Patent Documents 1 to 3, and backcrossed for 8 generations or more, so that a C57BL/6 genetic background was achieved. $Foxp3^{eGFP}$ mice were purchased from the Jackson Laboratory.

<$Il10^{venus}$ Mice>

To form a bicistronic locus encoding both Il10 and Venus under control of an Il10 promoter, a targeting construct was first created. Specifically, a cassette (IRES-Venus-SV40 polyA signal cassette, refer to Non-Patent Document 4) which was made of an internal ribosome entry site (IRES), a yellow fluorescent protein (Venus), and a SV40 polyA signal (SV40 polyA) and which was arranged next to a neomycin-resistant gene (neo), was inserted between a stop codon and a polyA signal (Exon 5) of a Il10 gene. Next, the obtained targeting construct was used to cause homologous recombination with the Il10 gene region in the genome of mice. Thus, $Il10^{venus}$ mice having an $Il10^{venus}$ alleles were produced (refer to FIG. 1). Note that in FIG. 1 "tk" represents a gene coding thymidine kinase, "neo" represents the neomycin-resistant gene, and "BamH1" represents a cleavage site by the restriction enzyme BamH1.

Figure 2:
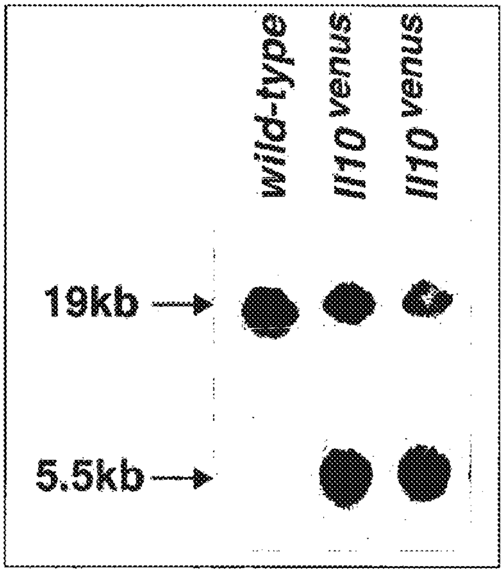
FIG. 2 is a diagram showing results of Southern blotting performed for analysis as to whether or not the Il10$^{venus}$ mice have an Il10$^{venus}$ allele.

Genomic DNAs were extracted from the $Il10^{venus}$ mice, treated with BamH1, and Southern blotted by use of a probe shown in FIG. 1. FIG. 2 shows the obtained results. Wild-type and $Il10^{venus}$ alleles were detected as bands having sizes of 19 kb and 5.5 kb, respectively. Hence, as is apparent from the results shown in FIG. 2, it was found that the homologous recombination shown in FIG. 1 occurred in the genome of the $Il10^{venus}$ mice.

Figure 3:
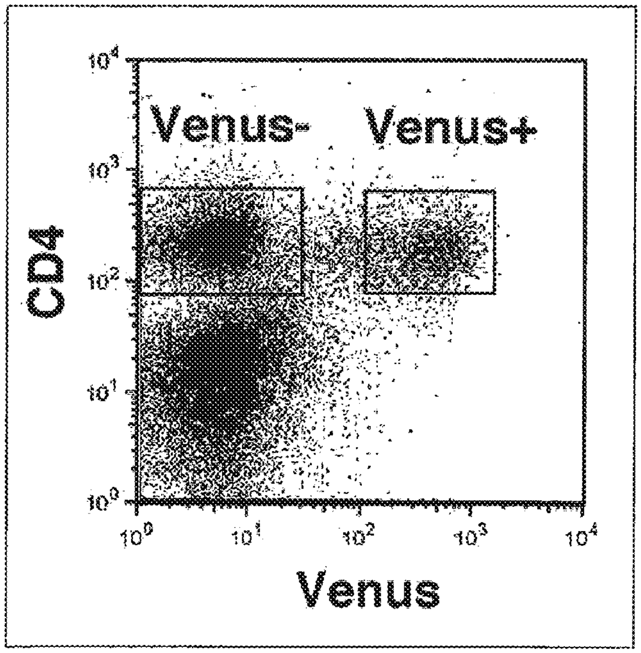
FIG. 3 is a FACS dot-plot diagram showing results obtained when Venus-positive cells and Venus-negative cells from the Il10$^{venus}$ mice were sorted.
Figure 4:
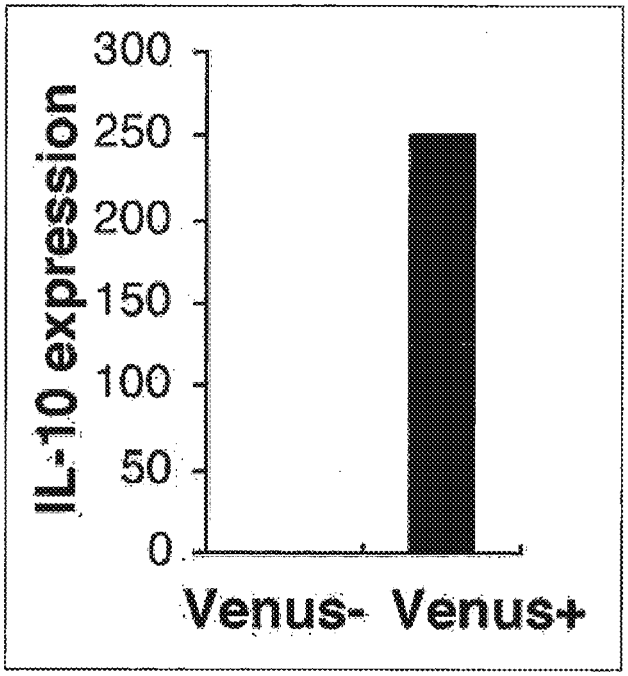
FIG. 4 is a graph showing the results obtained when the amounts of IL-10 mRNA expressed in Venus positive-cells and Venus-negative cells of the Il10$^{venus}$ mice were analyzed by real-time RT-PCR.

Further, $CD4^+$ $Venus^-$ cells or $CD4^+$ $Venus^+$ cells in the colonic lamina propria of the $Il10^{venus}$ mice were sorted by use of a FACSAria. Then, real-time RT-PCR was carried out on an ABI 7300 system by a method to be described later, to determine the amount of IL-10 mRNA expressed. FIGS. 3 and 4 show the obtained results. As is apparent from the results shown in FIGS. 3 and 4, it was found that, since the development of the IL-10 mRNA was detected only in the $CD4^+$ $Venus^+$ cells, the expression of IL-10 mRNA in the $Il10^{venus}$ mice was correctly reflected in the expression of Venus. Note that the germ-free states of such $Il10^{venus}$ mice were established in Central Institute for Experimental Animals (Kawasaki, Japan). The $Il10^{venus}$ mice in the germ-free states were maintained in vinyl isolators in Sankyo Labo Service Corporation, Inc. (Tokyo, Japan), and used in the following Examples.

Meanwhile, experiments and analyses in Examples were carried out as follows.

<Method for Colonization of Mice with Bacteria and Analysis Thereof>

According to the description in Non-Patent Documents 5 and 6, mice in which SFB or *Clostridium* were colonized were produced. Cecal contents or feces of the obtained gnotobiotic mice were dissolved in sterile water or an anaerobic dilution solution. The dissolved cecal contents or feces as they were or after a chloroform treatment were orally administered to GF mice. Three strains of the *Lactobacillus* and 16 strains of the *Bacteroides* were cultured separately from each other in a BL or EG agar medium in an anaerobic manner. The cultured bacteria were harvested, suspended in an anaerobic TS broth, and orally administrated forcibly to GF mice. The state of the colonization of the bacteria in the mice was assessed by microscopic observation conducted on a smear preparation of fecal pellets.

<Cell Separation and Flow Cytometry>

In order to isolate lymphocytes from the colonic lamina propria and the small intestinal lamina propria, the small intestine and the colon were collected, and cut open longitudinally. Then, fecal content and the like thereinside were washed to remove. Subsequently, the small intestine and the colon were shaken in HESS containing 5 mM of EDTA at 37° C. for 20 minutes. After removal of epithelium and fat tissue, the intestinal tissues were cut into small pieces. To the small pieces, RPMI 1640 (4% fetal bovine serum (FBS), 1 mg/ml of collagenase D, 0.5 mg/ml of dispase, and 40 μg/ml of DNaseI (all of which were manufactured by Roche Diagnostics K.K.)) were added, and the mixture was shaken in a water bath kept at 37° C. for 1 hour. The digested tissues were washed with HBSS containing 5 mM of EDTA, and resuspended in 5 ml of 40% percoll (GE Healthcare). The suspension was overlayered on 2.5 ml of 80% percoll in a 15-ml Falcon tube. Then, centrifugation was carried out at room temperature and at 2000 rpm for 20 minutes to conduct cell separation by percoll density gradient centrifugation. Cells at the interface were collected, and used as lamina propria lymphocytes. The collected cells were suspend in a staining buffer (PBS, 2% FBS, 2 mM EDTA, and 0.09% $NaN_3$), and stained by use of an anti-CD4 antibody (RM4-5, BD Biosciences) labeled with PE or PE-Cy7. After the staining of CD4, Foxp3 in the cells were stained by use of Cytofix/Cytoperm Kit Plus with Golgistop (BD Biosciences) or Foxp3 Staining Buffer Set (eBioscience), as well as an anti-Foxp3 antibody (FJK-16s, eBioscience) labeled with Alexa647. Flow cytometry was performed by use of a FACScant II, and the data were analyzed by FlowJo software (TreeStar Inc.). The sorting of the cells were performed by use of a FACSAria.

<Real-Time RT-PCR>

From an RNA prepared by using RNeasy Mini Kit (Qiagen), a cDNA was synthesized by use of a MMV reverse transcriptase (Promega KK). The obtained cDNA was analyzed by real-time RT-PCR using Power SYBR Green PCR Master Mix (Applied Biosystems) and ABI 7300 real time PCR system (Applied Biosystems), or real-time RT-PCR using SYBR Premix Ex Taq (TAKARA) and Light Cycler 480. For each sample, a value obtained was normalized for the amount of GAPDH. A primer set was designed by using Primer Express Version 3.0 (Applied Biosystems), and those exhibiting a 90% or higher sequence identity at an initial evaluation were selected. The primer set used was as follows:

```
Foxp3
                                   (SEQ ID NO: 1)
5'-GGCAATAGTTCCTTCCCAGAGTT-3'

                                   (SEQ ID NO: 2)
5'-GGGTCGCATATTGTGGTACTTG-3'

CTLA4
                                   (SEQ ID NO: 3)
5'-CCTTTTGTAGCCCTGCTCACTCT-3'

                                   (SEQ ID NO: 4)
5'-GGGTCACCTGTATGGCTTCAG-3'

GITR
                                   (SEQ ID NO: 5)
5'-TCAGTGCAAGATCTGCAAGCA-3'

                                   (SEQ ID NO: 6)
5'-ACACCGGAAGCCAAACACA-3'

IL-10
                                   (SEQ ID NO: 7)
5'-GATTTTAATAAGCTCCAAGACCAAGGT-3'

                                   (SEQ ID NO: 8)
5'-CTTCTATGCAGTTGATGAAGATGTCAA-3'

GAPDH
                                   (SEQ ID NO: 9)
5'-CCTCGTCCCGTAGACAAAATG-3'

                                  (SEQ ID NO: 10)
5'-TCTCCACTTTGCCACTGCAA-3'

Mmp2
                                  (SEQ ID NO: 11)
5'-GGACATTGTCTTTGATGGCA-3'

                                  (SEQ ID NO: 12)
5'-CTTGTCACGTGGTGTCACTG-3'

Mmp9
                                  (SEQ ID NO: 13)
5'-TCTCTGGACGTCAAATGTGG-3'

                                  (SEQ ID NO: 14)
5'-GCTGAACAGCAGAGCCTTC-3'

Mmp13
                                  (SEQ ID NO: 15)
5'-AGGTCTGGATCACTCCAAGG-3'

                                  (SEQ ID NO: 16)
5'-TCGCCTGGACCATAAAGAA-3'

Ido1
                                  (SEQ ID NO: 17)
5'-AGAGGATGCGTGACTTTGTG-3'

                                  (SEQ ID NO: 18)
5'-ATACAGCAGACCTTCTGGCA-3'.
```

<Preparation and Culturing of Large Intestinal Epithelial Cells (IECs)>

First, the colon was collected, cut open longitudinally, and rinsed with PBS. Subsequently, the colon was treated with 1 mM dithiothreitol (DTT) at 37° C. for 30 minutes on a shaker, and then vortexed for one minute to disrupt the epithelial integrity. The released IECs were collected, and suspended in 5 ml of 20% percoll. The suspension was overlayered on 2.5 ml of 80% percoll in a 15-ml Falcon tube. Then, the tube was centrifuged at 25° C. and 780 g for 20 minutes to conduct cell separation by percoll density gradient centrifugation. Cells at the interface were collected, and used as colonic IECs (purity: 90% or higher, viability: 95%). The obtained IECs thus collected were suspended in RPMI containing 10% FBS, and $1\times10^5$ cells of the IECs were cultured in a 24-well plate for 24 hours. Thereafter, the culture supernatant was collected, and measured for active TGF-β1 level by ELISA (Promega).

Meanwhile, for culturing T cells in vitro, $1.5\times10^5$ MACS-purified splenic $CD4^+$ T cells were cultured in each well of a round-bottomed 96-well plate, together with a 50% conditioned medium in which IECs isolated from GF mice or *Clostridium*-colonized mice were cultured, and with 25 ng/ml of hIL-2 (Peprotech), in the presence or absence of 25 μg/ml of an anti-TGF-β antibody (R&D). Note that 10 μg/ml of an anti-CD3 antibody and an anti-CD28 antibody (BD Bioscience) were bound to the round-bottomed plate. After a 5-day culture, the $CD4^+$ T cells were collected, and subjected to a real-time PCR.

<Colitis Experimental Model>

A fecal suspension of *Clostridium*-colonized mice was orally administered to C57BL/6 mice (2-week old), and grown in a conventional environment for six weeks.

For preparing a DSS-induced colitis model, 2% (wt/vol) DSS (reagent grade, DSS salt, molecular weight =36 to 50 kD, manufactured by MP Biomedicals), together with drinking water, was given to the mice for six days.

Meanwhile, for preparing an oxazolone-induced colitis model, the mice were presensitized by transdermally applying, onto the mice, 150 μl of a 3% oxazolone (4-ethoxymethylene-2-phenyl-2-oxazolin-5-one, Sigma-Aldrich)/100% ethanol solution. Five days after that, 150 μl of a 1% oxazolone/50% ethanol solution was intrarectally administered again to the presensitized mice under a light anesthesia. Note that the intrarectal administration was conducted by using a 3.5 F catheter.

Each mouse was analyzed daily for body weight, occult blood, bleeding visible with the naked eyes (gross blood), and the hardness of stool. Moreover, the body weight loss percentage, intestinal bleeding (no bleeding, occult blood (hemoccult+), or bleeding visible with the naked eyes), and the hardness of stool (normal stool, loose stool, or diarrhea) were evaluated numerically, and the disease activity index (DAI) was calculated in accordance with the description in "S. Wirtz, C. Neufert, B. Weigmann, M. F. Neurath, Nat Protoc 2, 541 (2007)."

<OVA Specific IgE Reaction>

BALE/c SPF mice were inoculated with a fecal suspension of *Clostridium*-colonized mice (2-week old), and grown in a conventional environment. Then, 1 μg of OVA (grade V, Sigma) and 2 mg of alum (Thermo Scientific), 0.2 ml in total, were intraperitoneally injected to the mice (at their ages of 4 weeks and 6 weeks). Sera were collected every week from the mice at the root of their tail, and OVA-specific IgE was measured by ELISA (Chondrex). Then, at their ages of 8 weeks, splenic cells were collected, inoculated in a 96-well plate at $1\times10^6$ cells per well, and stimulated with OVA (100 μg/ml) for three days. Thereafter, the culture supernatant was collected, and measured for IL-4 and IL-10 levels by ELISA (R&D).

<Statistical Analysis>

The difference between control and experimental groups was evaluated by the Student's t-test.

Example 1

Figure 5:
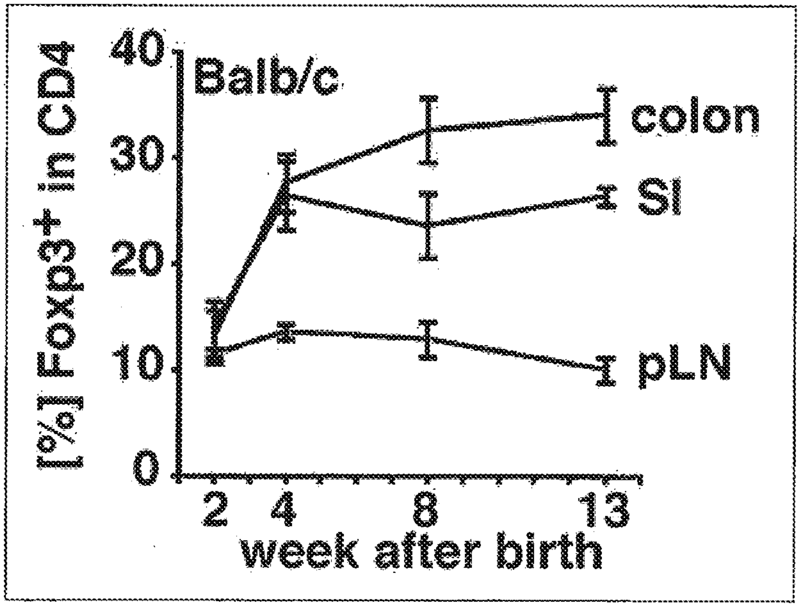
FIG. 5 is a graph showing change in the ratio of Foxp3$^+$ cells in CD4$^+$ lymphocytes of SPF mice.

First, it was investigated whether or not accumulation of regulatory T cells (Treg cells) in the colonic lamina propria was dependent on commensal bacteria. Specifically, lymphocytes were isolated from peripheral lymph nodes (pLN) of Balb/c mice bred in the absence of specific pathogenic bacteria (SPF) or from lamina propria of the colon or the small intestine (SI) of the mice. The CD4 and Foxp3 were stained by antibodies. Then, the ratio of $Foxp3^+$ cells in $CD4^+$ lymphocytes was analyzed by flow cytometry. FIG. 5 shows the obtained results. As is apparent from the results shown in FIG. 5, it was found that $Foxp3^+$ Treg cells were present at a high frequency in the lamina propria of the gastrointestinal tracts, especially in the colonic lamina propria, of the mice kept under the environment free from specific pathogenic microorganisms (SPF). In addition, it was also found that the number of the $Foxp3^+$ Treg cells in the colonic lamina propria gradually increased up to three months after their birth, whereas the number of the $Foxp3^+$ Treg cells in the peripheral lymph nodes was basically constant from the time of two weeks after their birth.

Example 2

Figure 6:
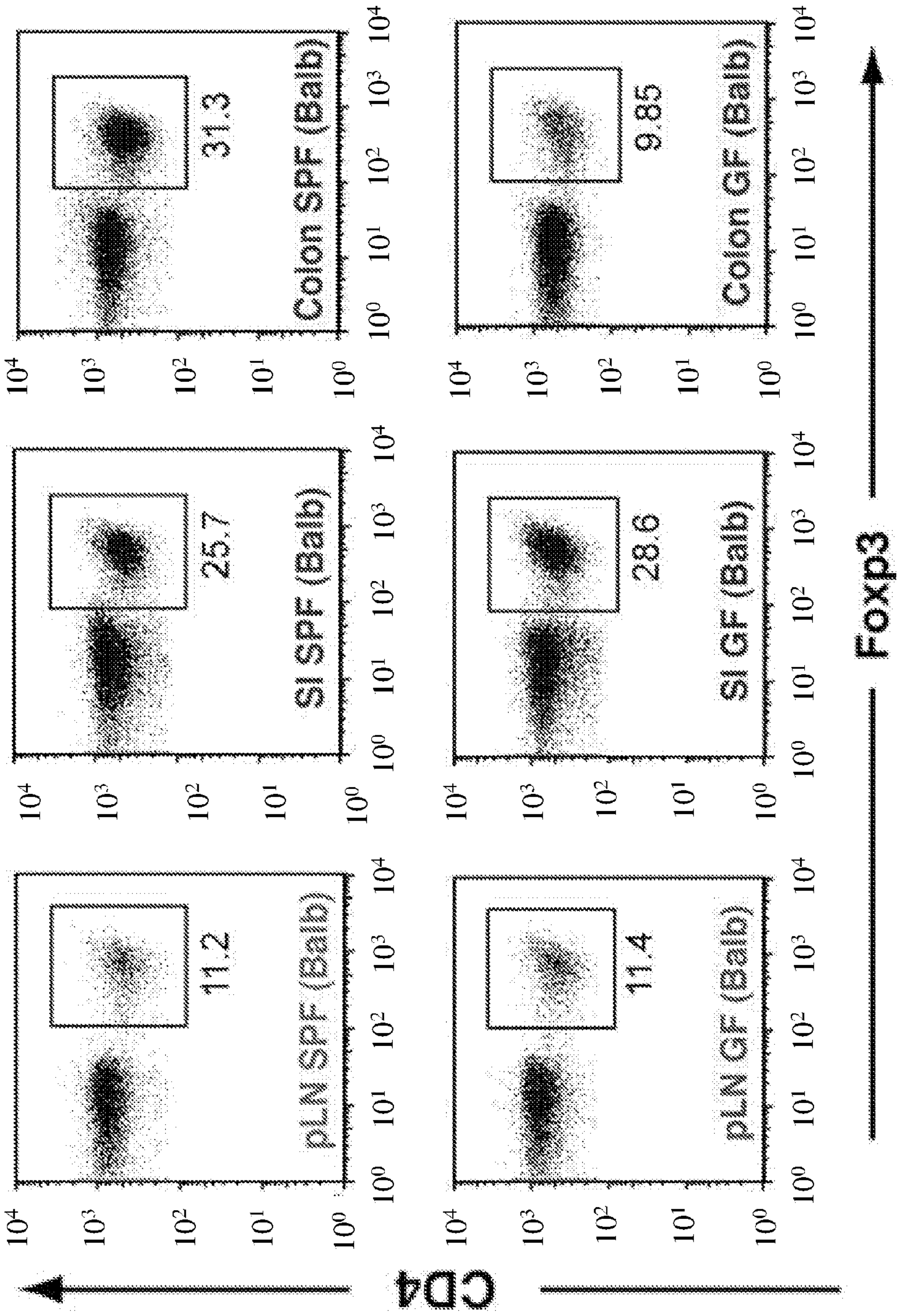
FIG. 6 shows FACS dot-plot diagrams showing analysis results of the ratios of Foxp3$^+$ cells in CD4$^+$ lymphocytes isolated from the small intestine, the colon, and the peripheral lymph nodes of GF mice and SPF mice.
Figure 7:
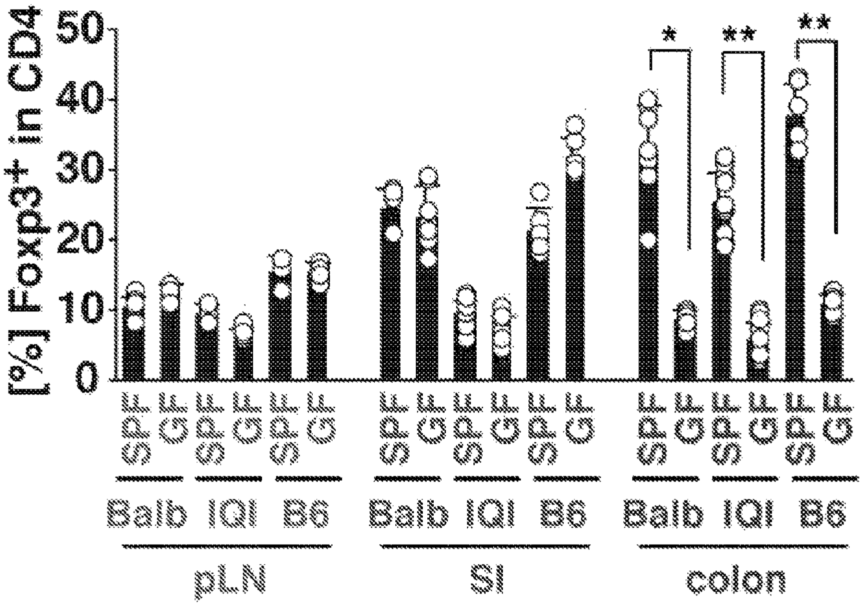
FIG. 7 is a graph showing analysis results of the ratios of Foxp3$^+$ cells in CD4$^+$ lymphocytes isolated from the small intestine, the colon, and the peripheral lymph nodes of GF mice and SPF mice.

Next, it was investigated whether or not the temporal accumulation of the Treg cells in the colon as found in Example 1 had a relationship with the colonization of intestinal commensal microbiota. Specifically, the expression of CD4 and the expression of Foxp3 in lymphocytes isolated from the small intestine, the colon, and the peripheral lymph nodes of mice bred under a germ-free (GF) or SPF environment (8 weeks old: Balb/c mice, IQI mice, and C57BL/6 mice) were analyzed. Similar results were obtained in three or more independent experiments. FIGS. 6 and 7 show the obtained results. Note that, in FIG. 7, each white circle represents the absolute number of $CD4^+$ $Foxp3^+$ cells in an individual mouse, and the error bars represent standard deviations (SDs).

Figure 8:
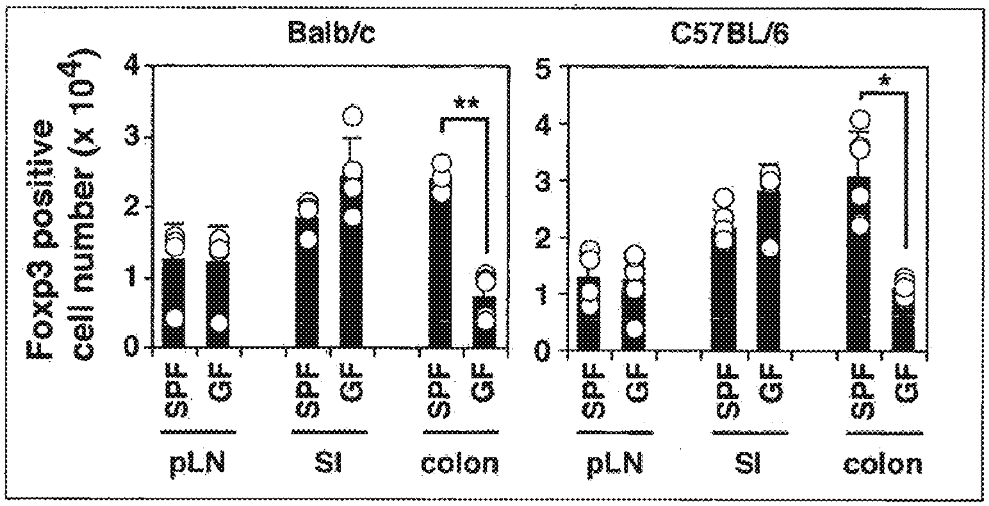
FIG. 8 shows graphs showing analysis results of the numbers of CD4$^+$ Foxp3$^+$ cells isolated from the small intestine, the colon, and the peripheral lymph nodes of GF mice and SPF mice.

In addition, lamina propria lymphocytes were collected from SPF mice and GF mice (Balb/c mice or C57BL/6 mice). CD4 and Foxp3 were stained with antibodies. Then, the lamina propria lymphocytes were analyzed by FACS. FIG. 8 shows the obtained results. Note that in FIG. 8 each white circle represents the absolute number of $CD4^+$ $Foxp3^+$ cells in an individual mouse, ** indicates that "P<0.001", and * indicates that "P<0.01."

Figure 9:
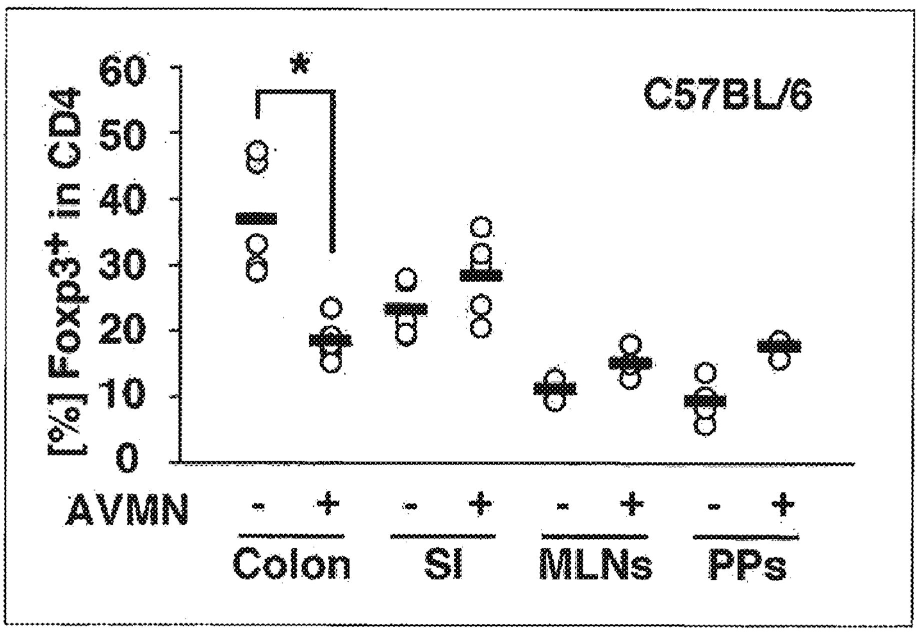
FIG. 9 is a plot diagram showing analysis results of the ratios of Venus$^+$ cells in CD4$^+$ cells in various tissues of SPF mice treated with antibiotics.

Further, lymphocytes were isolated from the lamina propria of the colon, the lamina propria of the small intestine (SI), Peyer's patches (PPs), and mesenteric lymph nodes (MLNs) of mice (SPF C57BL/6 mice) to which antibiotics were orally administered with water for eight weeks. CD4 and Foxp3 were stained with antibodies. Then, the lymphocytes were analyzed by FACS. Similar results were obtained in two or more independent experiments. FIG. 9 shows the obtained results (the ratio of the $Foxp3^+$ cells in the $CD4^+$ cells of an individual mouse). Note that the following antibiotics were used in combination in accordance with the description in the following document:

ampicillin (A; 500 mg/L, Sigma)

vancomycin (V; 500 mg/L, NACALAI TESQUE, INC.)

metronidazole (M; 1 g/L, NACALAI TESQUE, INC.)

neomycin (N; 1 g/L, NACALAI TESQUE, INC.)

Rakoff-Nahoum, J. Paglino, F. Eslami-Varzaneh, S. Edberg, R. Medzhitov, Cell 118, 229 (Jul. 23, 2004)

Fagarasan et al., Science 298, 1424 (Nov. 15, 2002)

In FIG. 9, each white circle represents the absolute number of the $CD4^+$ $Foxp3^+$ cells in an individual mouse, each horizontal bar represents the average value of the absolute numbers, * indicates that "P<0.01," and "AVMN" represents the kinds of the administered antibiotics by using the first letters of the antibiotics.

As is apparent from the results shown in FIGS. 6 to 9, the frequencies and the absolute numbers of $Foxp3^+$ $CD4^+$ cells in the small intestine and the peripheral lymph nodes of the GF mice were equal to or greater than those of the SPF mice (refer to FIGS. 6 to 8). In addition, the numbers of the Treg cells in the small intestinal lamina propria, Peyer's patches, and mesenteric lymph nodes of the SPF mice to which the antibiotics were orally administered for eight weeks were equal to or greater than those of the SPF mice (refer to FIG. 9). Meanwhile, the number of the $Foxp3^+$ $CD4^+$ cells in the colonic lamina propria of the GF mice was decreased significantly in comparison with that of the SPF mice (refer to FIGS. 6 and 7). This decrease was commonly observed among mice of different genetic backgrounds (Balb/c, IQI, and C57BL/6), as well as among mice bred in different animal facilities (refer to FIG. 7 for the data regarding the different genetic backgrounds, the data regarding the mice bred in the different animal facilities are not shown in the drawings). In addition, it was also shown that the number of Treg cells in the colonic lamina propria of the SPF C57BL/6 mice to which the antibiotics were administered was decreased significantly (refer to FIG. 9).

Example 3

Figure 10:
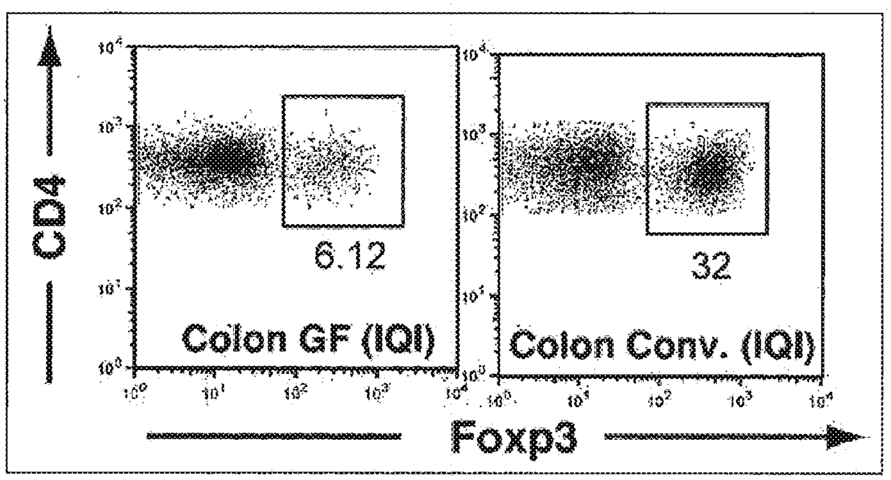
FIG. 10 shows FACS dot-plot diagrams showing analysis results of the ratio of Foxp3$^+$ cell in CD4$^+$ lymphocytes isolated from the colonic lamina propria of GF mice to which a fecal suspension of SPF mice was administered.
Figure 11:
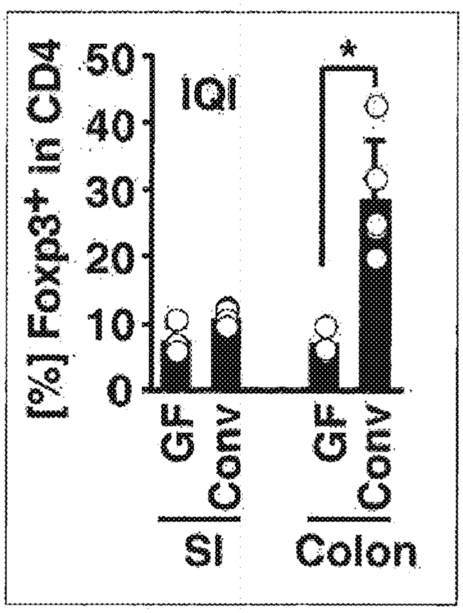
FIG. 11 is a graph showing analysis results of the ratios of Foxp3$^+$ cells in CD4$^+$ lymphocytes isolated from the lamina propria of the colon and the lamina propria of the small intestine of GF mice to which a fecal suspension of SPF mice was administered.

Next, it was directly checked whether or not the decrease in the number of the Treg cells in the colonic lamina propria of the GF mice shown in Example 2 was attributed to the absence of microbiota. Specifically, a fecal suspension of B6 SPF mice purchased from The Jackson Laboratory was orally administered to GF-IQI mice (conventionalization). Three weeks after the administration, lymphocytes were isolated from the colonic lamina propria, and the expression of Foxp3 in $CD4^+$ lymphocytes was analyzed. FIGS. 10 and 11 show the obtained results. Note that each white circle in FIG. 11 represents the absolute number of $CD4^+$ $Foxp3^+$ cells in an individual mouse, the error bars represent standard deviations (SD), * indicates that "P<0.01" in Student's t-test, and  indicates that "P<0.001." As is apparent from the results shown in FIGS. 10 and 11**, the number of Treg cells in the small intestinal lamina propria did not change. However, the number of the Treg cells in the colonic lamina propria increased significantly. Hence, it was shown that host-microbial interaction played an important role in the accumulation of $Foxp3^+$ Treg cells in the colonic lamina propria, while the accumulation of the Treg cells in the small intestinal lamina propria had a different mechanism.

Example 4

Figure 12:
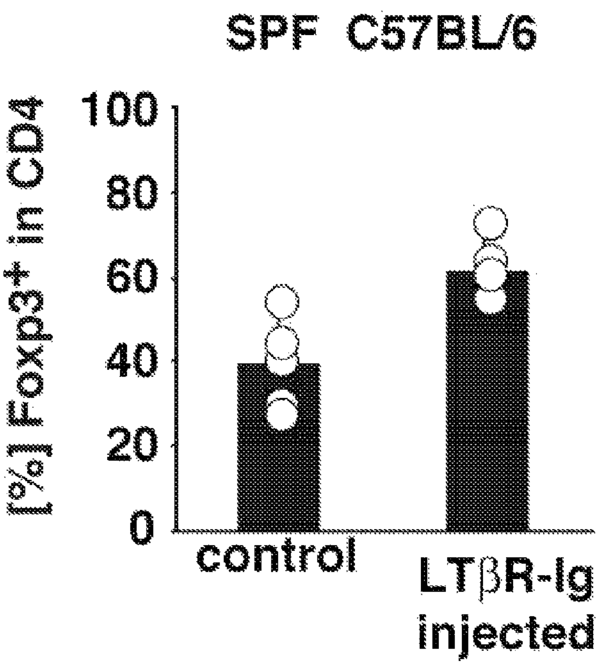
FIG. 12 is a graph showing analysis results of the ratio of Foxp3$^+$ cells in CD4$^+$ lymphocytes isolated from the lamina propria of mice deficient in ILFs, PPs, and colonic-patches.

Next, the relationship between the gut-associated lymphoid tissues of mice and the number of $Foxp3^+$ cells in the colonic lamina propria of the mice was investigated in accordance with the method described in M. N. Kweon et al., J Immunol 174, 4365 (Apr. 1, 2005). Specifically, 100 μg of an extracellular domain recombinant protein (a fusion protein (LTβR-Ig) between a lymphotoxin β receptor (LTβR) and a Fc region of human IgG1, refer to Honda et al., J Exp Med 193, 621 (Mar. 5, 2001)) was injected intraperitoneally into pregnant C57BL/6 mice 14 days after conception. The LTβR-Ig was again injected intraperitoneally into fetuses obtained from such mice, so that mice from which isolated lymphoid follicles (ILFs), Peyer's patches (PPs), and colonic-patches (CPs) were completely removed were produced. Then, the ratios of $Foxp3^+$ cells in $CD4^+$ cells in the colonic lamina propria of the mice treated with the LTβR-Ig, and mice treated with rat IgG (control) were analyzed by FACS. FIG. 12 shows the obtained results. Note that in FIG. 12 each white circle represents the ratio of $Foxp3^+$ cells in an individual mouse, and the error bars represent standard deviations. As is apparent from the results shown in FIG. 12, it was found that the ratio of the $Foxp3^+$ cells in the colonic lamina propria of the mice deficient in isolated lymphoid follicles, Peyer's patches, and the colonic-patches (the mice treated with the LTβR-Ig) rather increased. Accordingly, it was suggested that the decrease in the number of the Treg cells in the colonic lamina propria of the GF mice and the mice treated with the antibiotics was caused because the transmission of specific signals which promotes the accumulation of Treg cells in the colonic lamina propria and which is caused by the intestinal microbes did not occur, rather than simply because of a secondary effect of disorganized gut-associated lymphoid tissues.

Example 5

Figure 30:
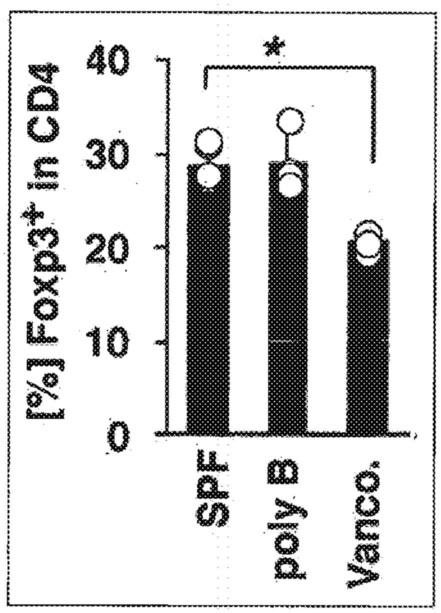
FIG. 30 is a graph showing the results obtained when SPF B6 mice were treated with polymyxin B or vancomycin for 4 weeks, and then analyzed for the ratio of Foxp3$^+$ cells in the CD4$^+$ cell group.

To investigate whether or not a specific intestinal flora induced the accumulation of colonic Treg cells, vancomycin as an antibiotic against Gram-positive bacteria or polymyxin B as an antibiotic against Gram-negative bacteria was administered to SPF mice (from 4 weeks of age) for four weeks, and analyzed for the ratio of $Foxp3^+$ cells in the $CD4^+$ cell group ([%] $Foxp3^+$ in CD4). FIG. 30 shows the obtained results. Note that, in FIG. 30, "SPF" indicates the result of SPF mice (control), "poly B" indicates the result of the SPF mice to which polymyxin B was administered, and "Vanco." indicates the result of the SPF mice to which vancomycin was administered. Meanwhile, * indicates that "P<0.01."

As is apparent from the results shown in FIG. 30, the number of Treg cells in the colon of the mice to which vancomycin was administered was markedly decreased in comparison with that of the control. In contrast, no influence was observed on the number of Treg cells of the mice to which polymyxin B was administered. Those facts suggested that Gram-positive commensal bacteria played a major role in accumulation of Treg cells.

Example 6

Figure 31:
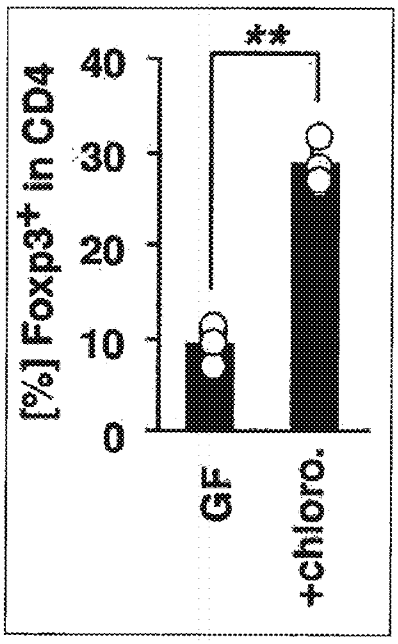
FIG. 31 is a graph showing the results obtained when SPF mice-derived chloroform-treated feces were orally administered to GF mice, and then the ratio of Foxp3$^+$ cells in the CD4$^+$ cell group was analyzed.

A recent report has suggested that spore-forming bacteria play an important role in intestinal T cells response (see V. Gaboriau-Routhiau et al., Immunity 31, 677 (Oct. 16, 2009)). In this respect, fecal microorganisms (spore-forming fraction) resistant to 3% chloroform were orally administered to GF mice, which were then analyzed for the ratio of $Foxp3^+$ cells in the $CD4^+$ cell group ([%] $Foxp3^+$ in CD4). FIG. 31 shows the obtained results. Note that, in FIG. 31, "GF" indicates the result of GF mice, and "+chloro" indicates the result of the GF mice to which the chloroform-treated feces were administered. Meanwhile, ** indicates that "P<0.001."

As is apparent from the results shown in FIG. 31, three weeks after the administration of the chloroform-treated feces, the number of Treg cells in the administered mice was markedly increased to the same level as those of the SPF mice and the GF mice to which the untreated feces was forcibly administered (see FIGS. 7 and 11).

Accordingly, considering the results shown in Example 5 in combination, it was revealed that the specific components of the indigenous microbiota were highly likely to belong to the Gram-positive group, and that the spore-forming fraction played an important role in the induction of Treg cells.

Example 7

Next, the species of the intestinal microbiota which induced the accumulation of Treg cells in the colon as suggested in Examples 4 to 6 were identified. Specifically, segmented filamentous bacteria (SFB), 16 strains of the *Bacteroides* spp. (*Bactero.* (6 strains of *B. vulgatus,* 7 of the *B. acidifaciens* group 1, and 3 of the *B. acidifaciens* group 2)), 3 strains of the *Lactobacillus* (*Lacto.* (*L. acidophilus, L. fermentum*, and *L. murinum*)), and 46 strains of *Clostridium* spp. (*Clost.*, refer to "Itoh, K., and Mitsuoka, T. Characterization of clostridia isolated from faeces of limited flora mice and their effect on caecal size when associated with germ-free mice. Lab. Animals 19: 111-118 (1985))"), or microbiota collected from mice (SPF) bred under a conventional environment was orally administered to GF-Balb/c mice or GF-IQI mice. The mice were maintained in vinyl isolators for three weeks. Then, CD4 cells were isolated from the colon and the small intestine of these mice. The numbers of Treg cells in the colon and the small intestine were analyzed by flow cytometry.

Figure 13:
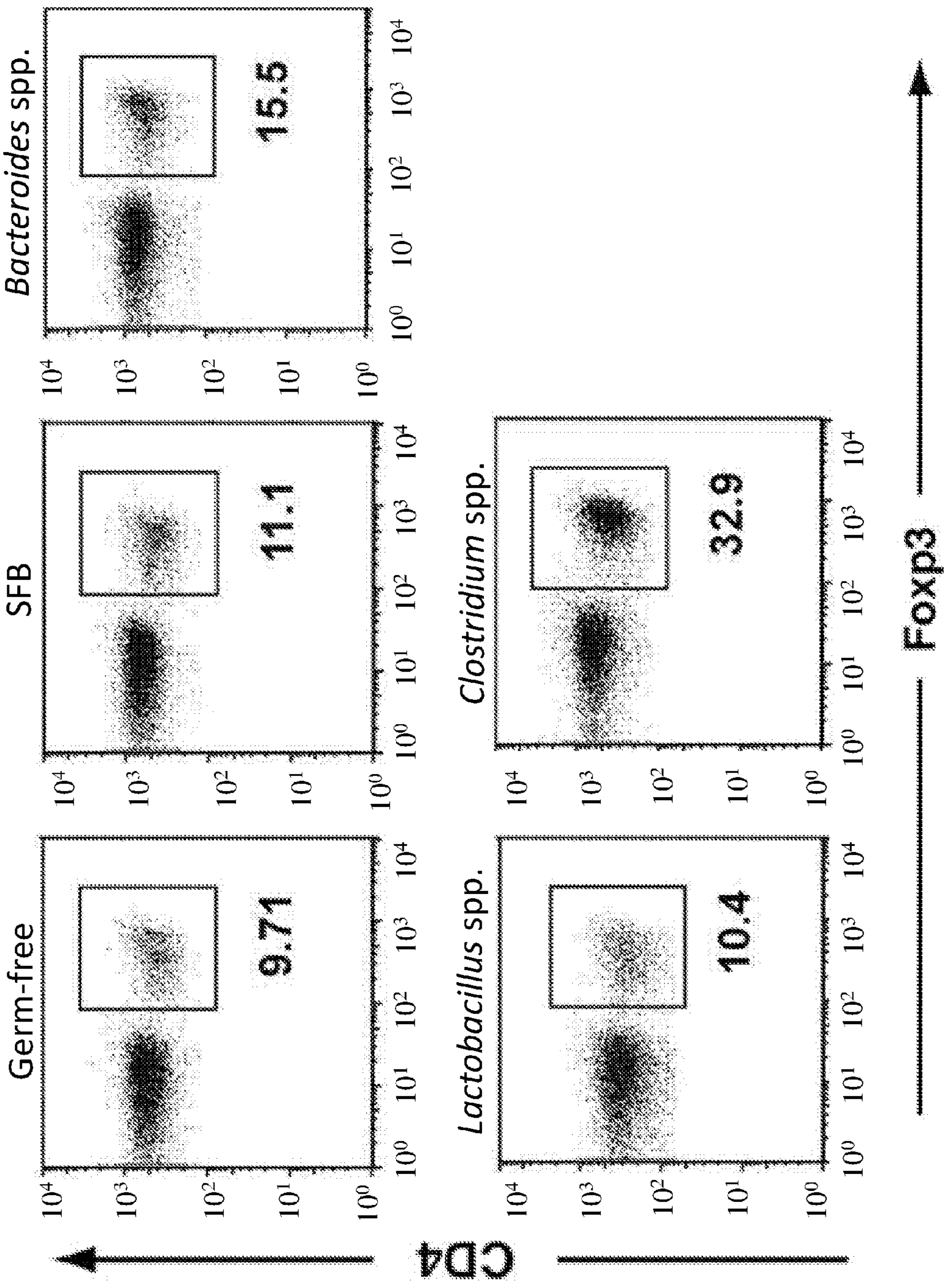
FIG. 13 shows FACS dot-plot diagrams showing analysis results of the ratios of Foxp3$^+$ cells in CD4$^+$ lymphocytes isolated from the colonic lamina propria of GF mice to which specific commensal bacteria were administered.
Figure 14:
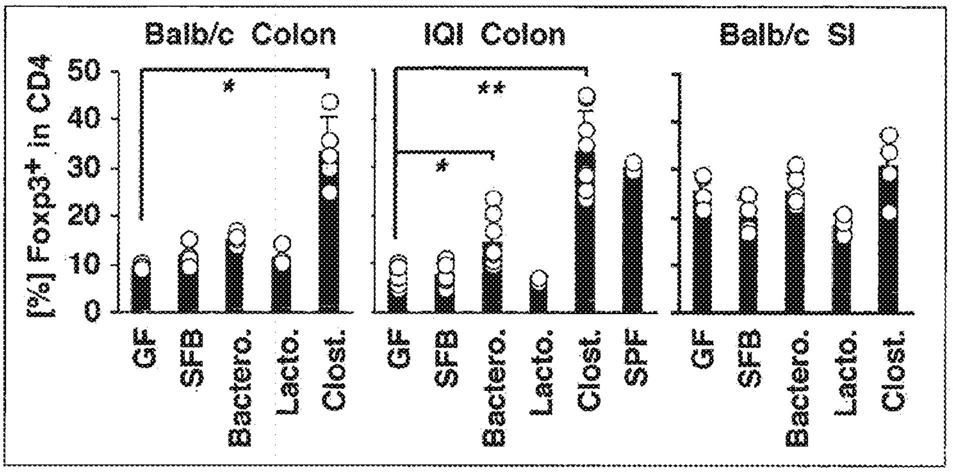
FIG. 14 shows graphs showing analysis results of the ratios of Foxp3$^+$ cells in CD4$^+$ lymphocytes isolated from the colonic lamina propria of GF mice to which specific commensal bacteria were administered.

FIG. 13 shows FACS dot-plots obtained when a gate was set on $CD4^+$ cells of the Balb/c mice. FIG. 14 shows the ratio of $Foxp3^+$ cells in $CD4^+$ cells of each mouse.

Note that, the bacteria belonging to the genus *Clostridium* are classified by sequencing of 16S rRNA gene, as follows. Specifically, the 16S rRNA genes of the bacteria were amplified by PCR using 16S rRNA gene-specific primer pairs: 5'-AGAGTTTGATCMTGGCTCAG-3' (SEQ ID NO: 19) and 5'-ATTACCGCGGCKGCTG-3' (SEQ ID NO: 20) (see T. Aebischer et al., Vaccination prevents *Helicobacter pylori*-induced alterations of the gastric flora in mice. FEMS Immunol. Med. Microbiol. 46, 221-229(2006)). The 1.5-kb PCR product was then introduced into pCR-Blunt Vector. The inserts were sequenced and aligned using the ClustalW software program. The resulting sequences of 16S rRNA genes derived from strain 1-41 of 46 strains of *Clostridium* spp. were shown in SEQ ID NOs: 21-61. Phylogenetic tree which was constructed by the neighbor-joining method with the resulting sequences of the 41 strains of *Clostridium* and those of known bacteria obtained from Genbank database using Mega software was shown in FIG. 49.

As is apparent from the results shown in FIGS. 13 and 14, no effect on the number of the Treg cells in the colon was observed in the GF mice in which the segmented filamentous bacteria (SFB) were colonized (refer to FIG. 14). Moreover, mice in which the cocktail of three strains of *Lactobacillus* was colonized gave similar results (refer to FIG. 14). On the other hand, it was shown that the accumulation of $Foxp3^+$ cells in the colonic lamina propria was strongly induced in the mice in which 46 strains of *Clostridium* spp. were colonized. Importantly, such accumulation was promoted irrespective of the genetic backgrounds of the mice, and led to the increase in number similar to that in the SPF mice although intestinal microbiota of only a single genus were colonized. It was also shown that the colonization of the *Clostridium* did not change the number of Treg cells in the small intestinal lamina propria (refer to FIG. 14). Note that, when the 16 strains of Bactericides spp. were colonized, the number of Treg cells in the colon was increased significantly. However, the extent of the increase varied depending on the genetic background of the mice in which the bacteria were colonized (refer to FIGS. 13 and 14).

Example 8

Next, CD4 expression, Foxp3 expression, and Helios expression in LP lymphocytes of the thymuses and the colons of SPF mice, GF mice, *Lactobacillus*-colonized mice, and *Clostridium*-colonized mice were analyzed by flow cytometry.

Figure 32:
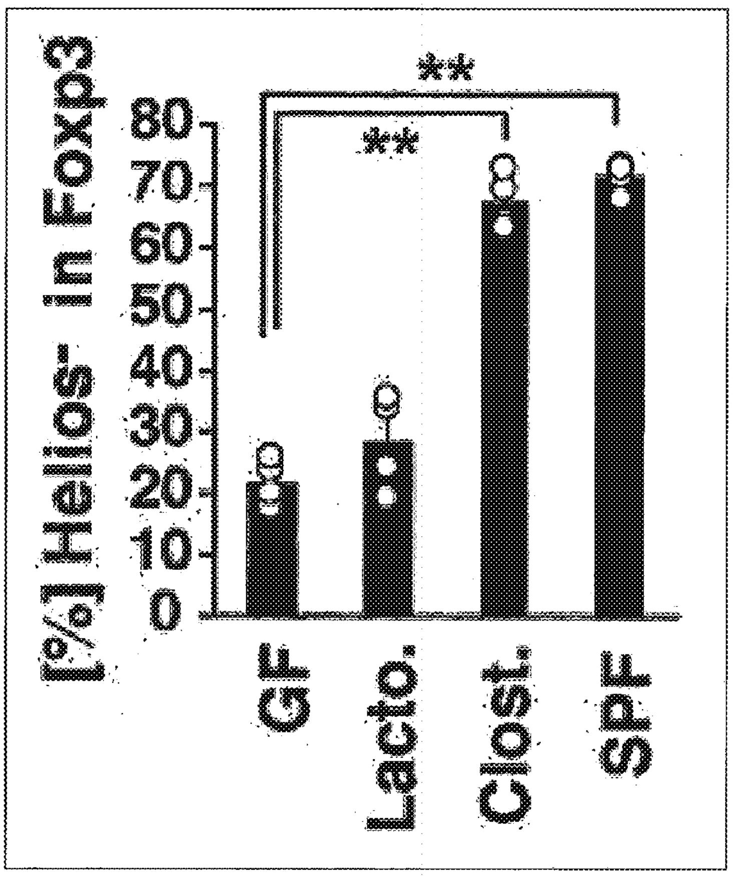
FIG. 32 is a graph showing the general results of flow cytometry analysis on Helios expression in LP lymphocytes in the thymuses or the colons of SPF mice, GF mice, *Lactobacillus*-colonized mice, or *Clostridium*-colonized mice.
Figure 33:
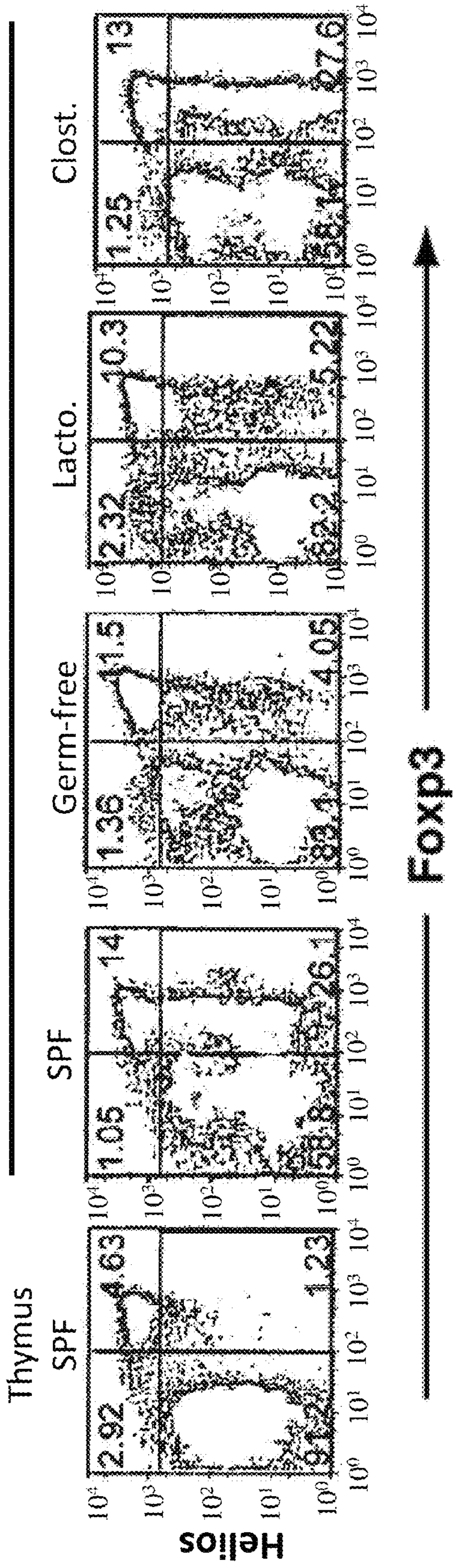
FIG. 33 shows plot diagrams showing representative results of flow cytometry analysis on CD4 expression, Foxp3 expression, and Helios expression in the LP lymphocytes in the thymuses or the colons of the SPF mice, the GF mice, the *Lactobacillus*-colonized mice, or the *Clostridium*-colonized mice.

FIGS. 32 and 33 show the obtained results. Note that, in FIGS. 32 and 33, "GF" or "Germ Free" indicates the results of the GF mice, "SPF" indicates the results of the SPF mice, "*Lacto*." indicates the results of the *Lactobacillus*-colonized mice, and "*Clost*." indicates the results of the *Clostridium*-colonized mice. In FIG. 32, the vertical axis represents the ratio of $Helios^-$ cells in the $Foxp3^+$ cell group ([%] $Helios^-$ in $Foxp3^+$), and ** indicates that "P<0.001."

As is apparent from the results shown in FIGS. 32 and 33, most $Foxp3^+$ cells found in the SPF mice or the *Clostridium*-colonized mice did not express Helios. Note that Helios is a transcription factor known to be expressed in thymic-derived natural Treg cells (see A. M. Thornton et al., J Immunol 184, 3433 (Apr. 1, 2010)). Accordingly, it was suggested that most of the Treg cells in the SPF mice and the *Clostridium*-colonized mice were Treg cells induced in peripheral portions, i.e., so-called iTreg cells.

Example 9

Figure 15:
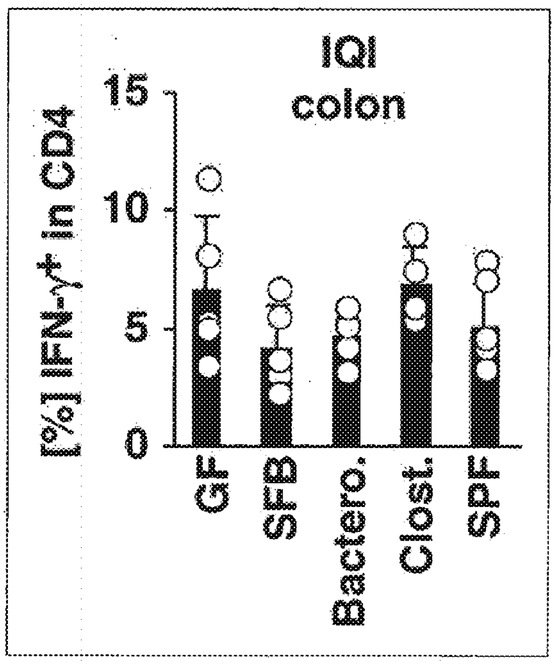
FIG. 15 is a graph showing analysis results of the ratios of IFN-γ$^+$ cells in CD4$^+$ lymphocytes isolated from the colonic lamina propria of mice in which specific commensal bacteria were colonized.
Figure 16:
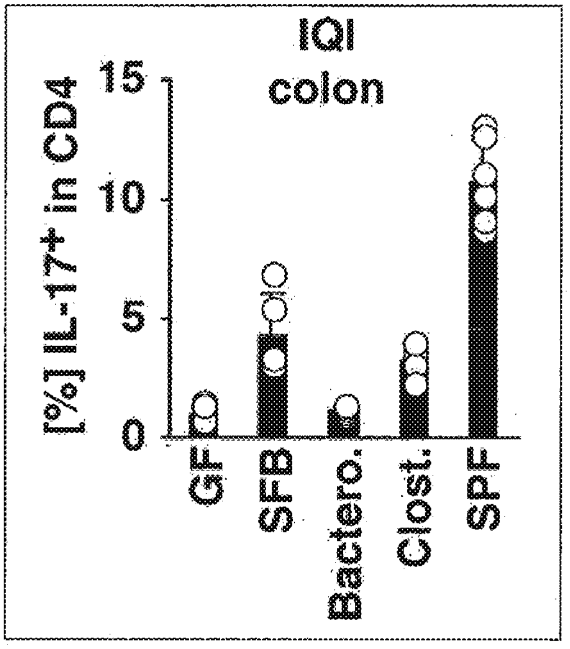
FIG. 16 is a graph showing analysis results of the ratios of IL-17$^+$ cells in CD4$^+$ lymphocytes isolated from the colonic lamina propria of mice in which specific commensal bacteria were colonized.

Next, it was investigated whether or not the colonization of the *Clostridium* or the like had an influence on other T cells. Specifically, SFB, 16 strains of *Bacteroides* spp. (*Bactero*.), 46 strains of *Clostridium* spp. (*Clost*.), or microbiota collected from mice bred under a conventional environment (SPF) was colonized in GF IQI mice. Three weeks later, lymphocytes in the colonic lamina propria were isolated from these mice, and stimulated with PMA (50 ng/ml) and ionomycin (1 μg/ml) for four hours in the presence of Golgistop (BD Bioscience). After the stimulation was given, intracellular cytokines were stained by using an anti-IL-17 PE antibody (TC11-18H10) and an anti-IFN-g FITC antibody (BD Bioscience) in accordance with the manual of a cytofix/cytoperm kit (BD Bioscience). Then, the ratio of $IFN\text{-}\gamma^+$ cells or $IL\text{-}17^+$ cells in $CD4^+$ leucocytes was analyzed by flow cytometry. FIGS. 15 and 16 show the obtained results. Note that, in FIGS. 15 and 16, each white circle represents the absolute number of $CD4^+$ $IFN\text{-}\gamma^+$ cells or the absolute number of $CD4^+$ $IL\text{-}17^+$ cells in each individual mouse, and the error bars represent standard deviations (SD). As is apparent from the results shown in FIGS. 15 and 16, the colonization of the *Clostridium* did not have any influence on Th1 cells ($CD4^+$ $IFN\text{-}\gamma^+$ cells) in the colon, and caused only a slight increase of Th17 cells ($CD4^+$ $IL\text{-}17^+$ cells). Accordingly, it was suggested that the genus *Clostridium* was a genus of bacteria which specifically induced Treg cells.

Example 10

It has been reported that 46 strains of *Clostridium* spp. exert an influence on the accumulation of $CD8^+$ intestinal tract intraepithelial lymphocytes (IELs) in the colon. Accordingly, it is conceivable that *Clostridium* regulates the immune system in various aspects, and that *Clostridium* exhibits a marked ability to induce and maintain Treg cells especially in the colon, as described above. In addition, a kind of cytokines, transforming growth factor-β (TGF-β), is known to play an important role in regulation of Treg cell generation.

Figure 34:
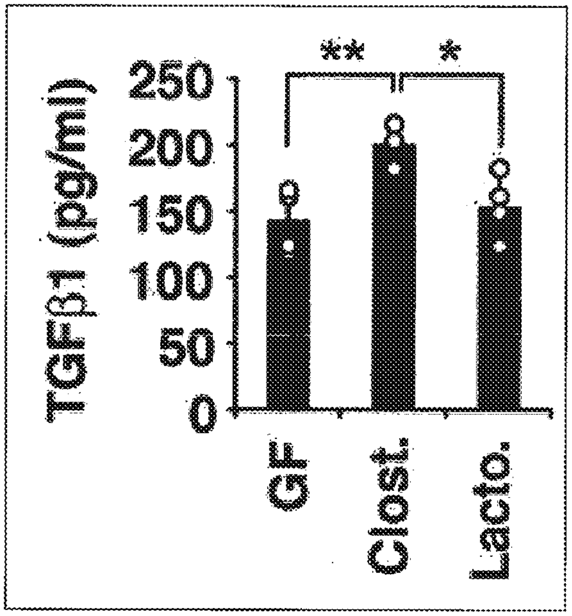
FIG. 34 is a graph showing the results obtained when the whole colons derived from GF mice, *Lactobacillus*-colonized mice, or *Clostridium*-colonized mice were cultured, and the culture supernatants thereof were analyzed for the TGF-β1 concentration by ELISA.

In this respect, it was examined whether or not the colonization of *Clostridium* provided a colonic environment rich in TGF-β. Specifically, first, the whole colons of GF mice, *Clostridium*-colonized mice, and *Lactobacillus*-colonized mice were cultured for 24 hours, and the culture supernatants thereof were measured for the concentration of active TGF-β (TGF-β1) by ELISA (the number of mice analyzed was four per group). FIG. 34 shows the obtained results. Note that, in FIG. 34, "GF" indicates the result of the GF mice, "*Clost*." indicates the result of the *Clostridium*-colonized mice, and "*Lacto*." indicates the result of *Lactobacillus*-colonized mice. Meanwhile, * indicates that "P<0.02," and ** indicates that "P<0.001."

As is apparent from the results shown in FIG. 34, the amount of TGF-β produced in the colons of the *Clostridium*-colonized mice was significantly larger than those of the GF mice and the *Lactobacillus*-colonized mice.

Figure 35:
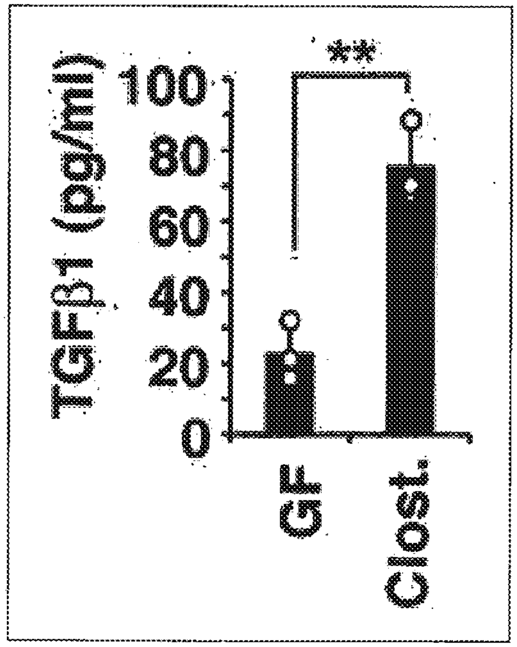
FIG. 35 is a graph showing the results obtained when intestinal epithelial cells (IECs) derived from GF mice or *Clostridium*-colonized mice were cultured, and the culture supernatants thereof were analyzed for the TGF-β1 concentration by ELISA.

Next, intestinal epithelial cells (IECs) of GF mice and *Clostridium*-colonized mice were cultured for 24 hours, and the culture supernatants thereof were measured for the concentration of active TGF-β (TGF-β1) by ELISA (the number of mice analyzed was four per group). FIG. 35 shows the obtained results. Note that, in FIG. 35, "GF" indicates the result of the GF mice, and "*Clost*." indicates the result of the *Clostridium*-colonized mice. Meanwhile, ** indicates that "P<0.001."

As is apparent from the results shown in FIG. 35, TGF-β was detected in the culture supernatant of the IECs isolated from the *Clostridium*-colonized mice, whereas no TGF-β was detected in the culture supernatant of the IECs isolated from the GF mice.

Figure 36:
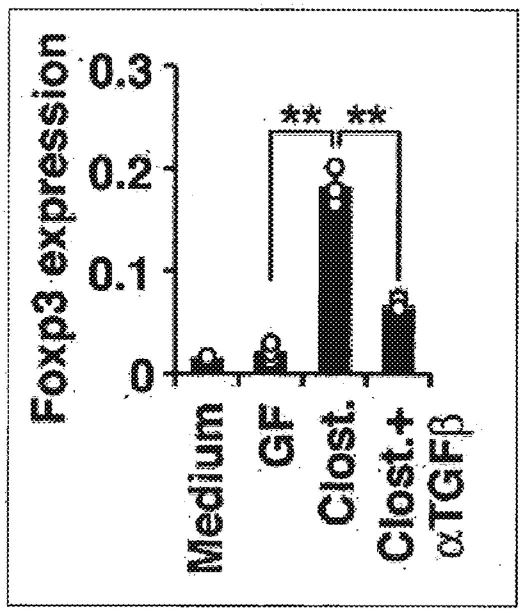
FIG. 36 is a graph showing the results obtained when splenic $CD4^+$ T cells were cultured together with an anti-CD3 antibody and with a culture supernatant of IECs isolated from GF mice or mice colonized with 46 bacterial strains of the genus *Clostridium* (*Clost.*) in the presence or absence of an anti-TGF-β antibody, and the T cells were collected on day 5 of the culture and analyzed for Foxp3 expression by real-time RT-PCR.

Next, as described above, splenic CD4+ T cells were cultured for five days together with a 50% conditioned medium in which IECs isolated from the GF mice or the *Clostridium*-colonized mice were cultured, and with the anti-CD3 antibody, in the presence or absence of an anti-TGF-β antibody. Then, the T cells were collected, and analyzed for expression of Foxp3 by real-time RT-PCR. FIG. 36 shows the obtained results. Note that, in FIG. 36, "Medium" indicates the result of a medium in which no cells were cultured, "GF" indicates the result of the conditioned medium in which the IECs of the GF mice were cultured, "*Clost*." indicates the result of the conditioned medium in which the IECs of the *Clostridium*-colonized mice were cultured, and "*Clost*.+αTGFβ" indicates the result of the conditioned medium to which the anti-TGF-β antibody was added and in which the IECs of the *Clostridium*-colonized mice were cultured. Meanwhile, ** indicates that "P<0.001."

As is apparent from the results shown in FIG. 36, when the culture supernatant of the IECs derived from the *Clostridium*-colonized mice was added to the splenic $CD4^+$ T cells, the differentiation into Foxp3-expressing cells was accelerated. Meanwhile, the differentiation into the Treg cells was inhibited by the anti-TGF-β antibody.

Moreover, the expression of MMP2, MMP9, and MMP13, which are thought to contribute to the activation of latent TGF-β was investigated. The expression of indoleamine 2,3-dioxygenase (IDO), which is thought to be involved in the induction of Treg cells, was also investigated. Specifically, 46 bacterial strains of the genus *Clostridium* (*Clost.*), or three bacterial strains of the genus *Lactobacillus* (*Lacto.*) were orally administered to C57BL/6 germ-free mice. Three weeks after the administration, IECs were collected, and analyzed for relative mRNA expression levels of MMP2, MMP9, MMP13, and IDO genes by real-time RT-PCR (the number of mice analyzed was three per group). FIGS. 37 to 40 show the obtained results. Note that, in FIGS. 37 to 40, "GF#1 to 3" indicate the results of GF mice, "*Clost.*#1 to 3" indicate the results of the *Clostridium*-colonized mice, and "*Lacto.*#1 to 3" indicate the results of the *Lactobacillus*-colonized mice.

For the relationship between the activation of latent TGF-β and the above-describe MMP, see D'Angelo et al., J. Biol. Chem. 276, 11347-11353, 2001; Heidinger et al., Biol. Chem. 387, 69-78, 2006; Yu et al., Genes Dev. i4, 163-176, 2000. For the relationship between IDO and the induction of Treg cells, see G. Matteoli et al., Gut 59, 595 (May, 2010).

Figure 37:
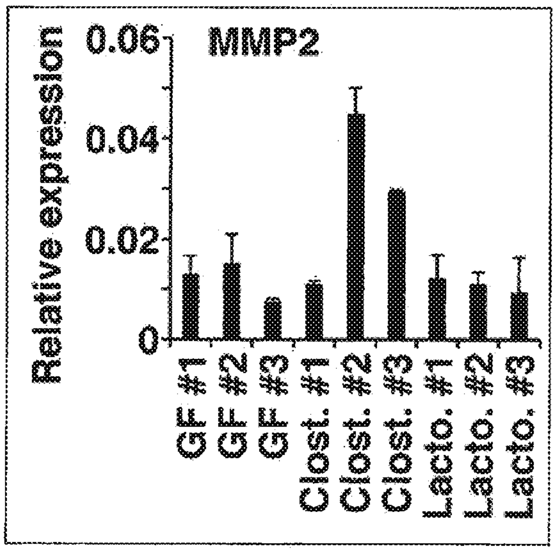
FIG. 37 is a graph showing the results obtained when C57BL/6 GF mice were orally inoculated with 46 bacterial strains of the genus *Clostridium* (*Clost.*) or three bacterial strains of the genus *Lactobacillus* (*Lacto.*), and IECs were collected three weeks after the inoculation and analyzed for the relative mRNA expression level of the MMP2 gene by real-time RT-PCR.
Figure 38:
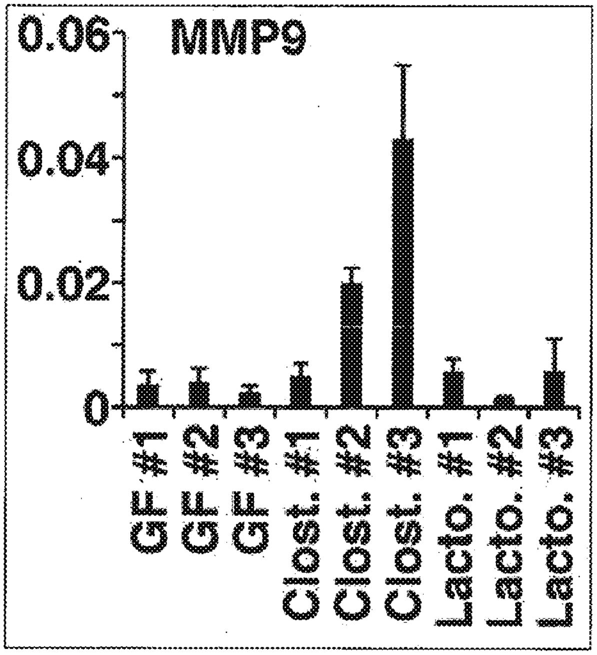
FIG. 38 is a graph showing the results obtained when C57BL/6 GF mice were orally inoculated with 46 bacterial strains of the genus *Clostridium* (*Clost.*) or three bacterial strains of the genus *Lactobacillus* (*Lacto.*), and IECs were collected three weeks after the inoculation and analyzed for the relative mRNA expression level of the MMP9 gene by real-time RT-PCR.
Figure 39:
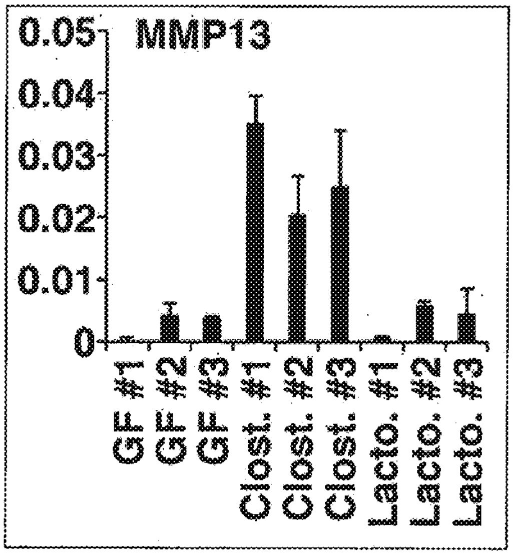
FIG. 39 is a graph showing the results obtained when C57BL/6 GF mice were orally inoculated with 46 bacterial strains of the genus *Clostridium* (*Clost.*) or three bacterial strains of the genus *Lactobacillus* (*Lacto.*), and IECs were collected three weeks after the inoculation and analyzed for the relative mRNA expression level of the MMP13 gene by real-time RT-PCR.

As is apparent from the results shown in FIGS. 37 to 39, in agreement with the production of TGF-β described above, transcription products of the genes encoding MMP2, MMP9, and MMP13 were expressed at higher levels in the IECs derived from the *Clostridium*-colonized mice than those in the GF mice and in the *Lactobacillus*-colonized mice.

Figure 40:
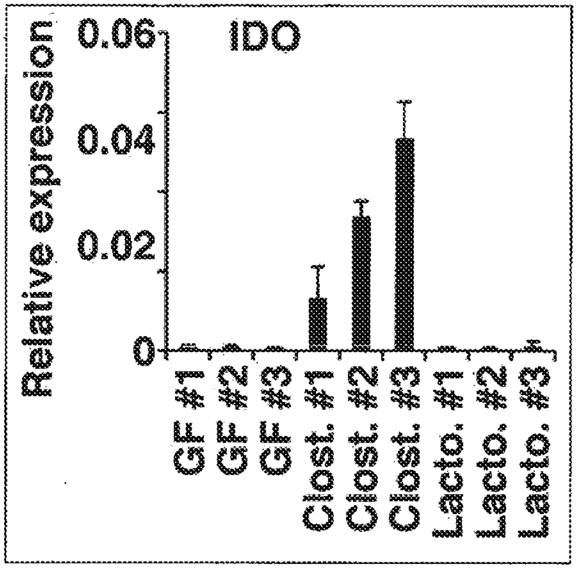
FIG. 40 is a graph showing the results obtained when C57BL/6 GF mice were orally inoculated with 46 bacterial strains of the genus *Clostridium* (*Clost.*) or three bacterial strains of the genus *Lactobacillus* (*Lacto.*), and IECs were collected three weeks after the inoculation and analyzed for the relative mRNA expression level of the IDO gene by real-time RT-PCR.

Moreover, as is apparent from the results shown in FIG. 40, IDO was expressed only in the *Clostridium*-colonized mice.

Accordingly, it was revealed that the *Clostridium* activated the IECs, and led to the production of TGF-β and other Treg cell-inducing molecules in the colon.

Example 11

Figure 17:
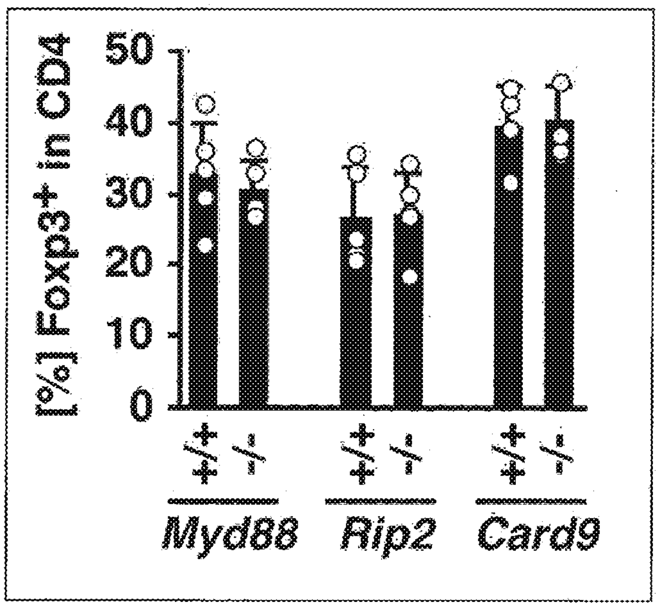
FIG. 17 is a graph showing analysis results of the ratios of Foxp3$^+$ cells in CD4$^+$ lymphocytes isolated from the colon of kinds of SPF mice each being deficient in a pathogen-associated molecular pattern recognition receptor-associated factor.
Figure 18:
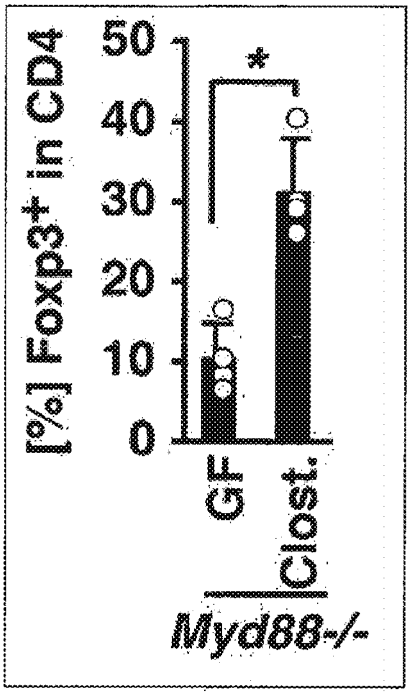
FIG. 18 is a graph showing analysis results of the ratios of Foxp3$^+$ cells in CD4$^+$ lymphocytes isolated from the colonic lamina propria of Myd88$^{-/-}$ mice in which the *Clostridium* was colonized.

Next, it was investigated whether or not the Treg cell accumulation induced by the colonization of the *Clostridium* was dependant on signal transmission by pathogen-associated molecular pattern recognition receptors. Specifically, the numbers of Treg cells in the colonic lamina propria of each of SPF mice of $Myd88^{-/-}$ (deficient in Myd88 (signaling adaptor for Toll-like receptor)), $Rip2^{--}$ (deficient in Rip2 (NOD receptor adaptor)), and $Card9^{-/-}$(deficient in Card9 (essential signal transmission factor for Dectin-1 signal transmission)) were examined. In addition, *Clostridium* spp. were caused to be colonized in the $Myd88^{-/-}$ GF mice, and the change in the number of Treg cells was investigated. FIGS. 17 and 18 show the obtained results. As is apparent from the results shown in FIGS. 17 and 18, the number of Treg cells of each kind of the SPF mice deficient in the associated factors of the pathogen-associated molecular pattern recognition receptors did not change relative to that of wild-type mice of the same litter, which served as a control. In addition, it was found that also when *Clostridium* spp. were colonized in GF mice deficient in Myd88, the accumulation of Treg cells in the colonic lamina propria was induced. Accordingly, it has been suggested that the mechanism of inducing the accumulation of Treg cells in the colonic lamina propria relies not on activation of recognition pathway for major pathogen-associated molecular patterns as is caused by most of bacterium, but on specific commensal bacterial species.

Example 12

Figure 19:
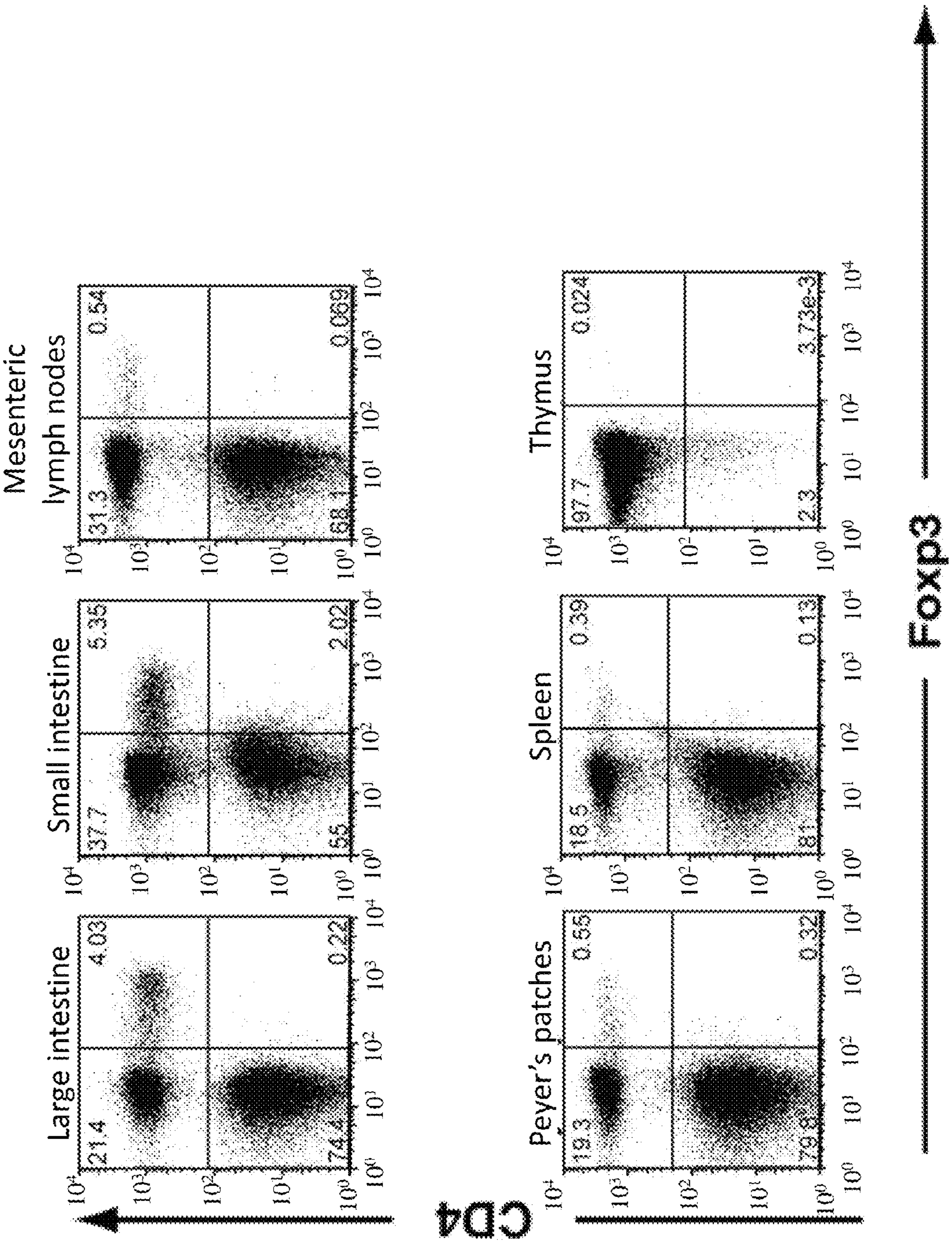
FIG. 19 shows FACS dot-plot diagrams showing analysis results of the ratios of Venus$^+$ cells in lymphocytes isolated from various tissues of Il10$^{venus}$ mice.
Figure 19:
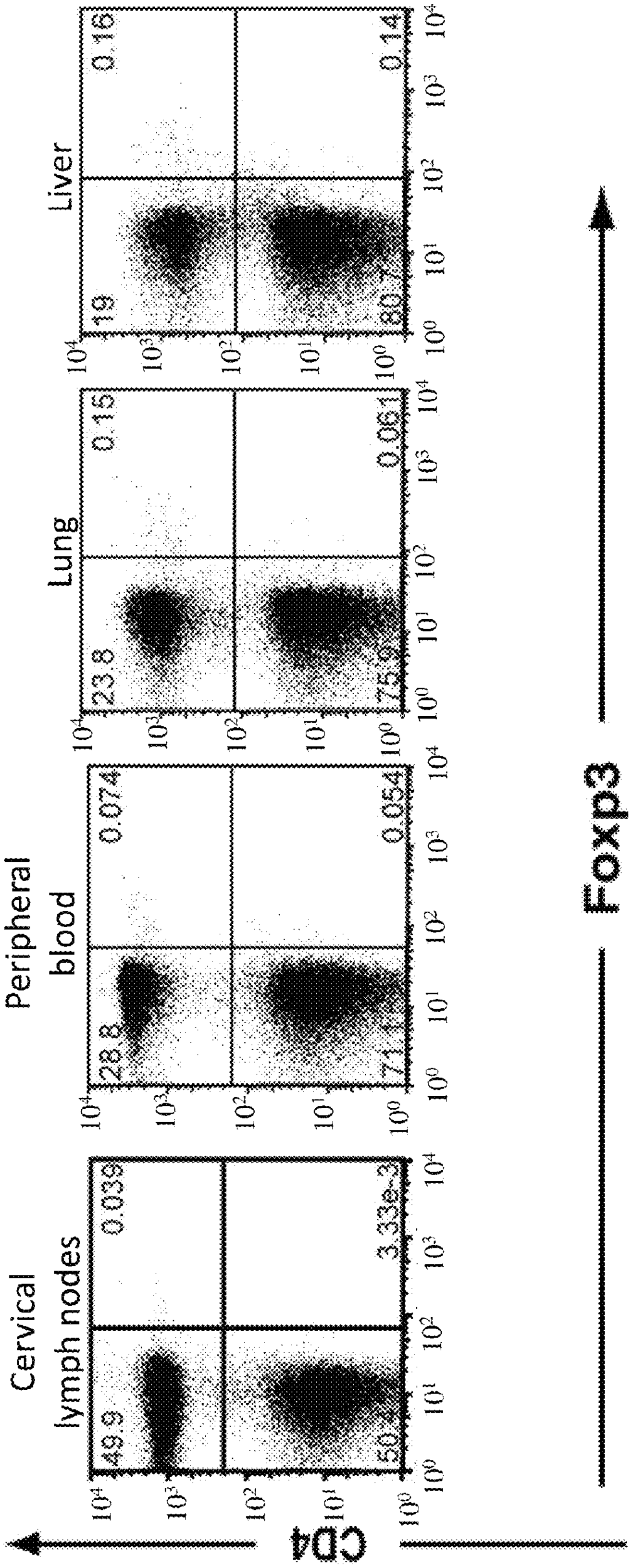

Intestinal tract $Foxp3^+$ Treg cells are known to exert some immunosuppressive functions through IL-10 production (refer to Non-Patent Document 9). Meanwhile, animals having $CD4^+$ $Foxp3^+$ cells from which IL-10 is specifically removed are known to develop inflammatory bowel disease (refer to Non-Patent Document 18). In this respect, first, the expression of IL-10 in lymphocytes of various tissues was examined. Specifically, lymphocytes were isolated from various tissues of SPF $Il10^{venus}$ mice, and the expression of CD4 and the expression of Venus were analyzed by flow cytometry. FIG. 19 shows the obtained results. Note that each numeric value in FIG. 19 represents the ratio of cells within the corresponding one of regions divided into four.

Figure 20:
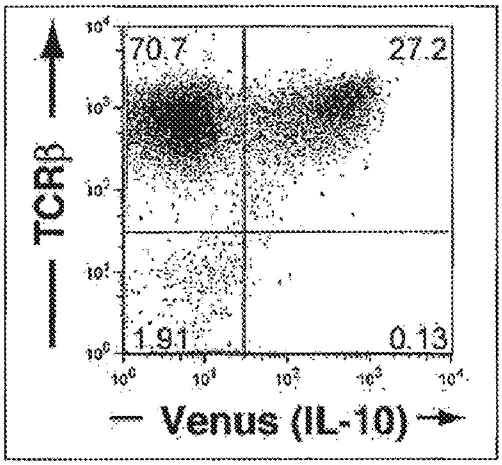
FIG. 20 is a FACS dot-plot diagram showing analysis results of the expression of a T cell receptor β chain on cell surfaces of lymphocytes isolated from the colonic lamina propria of Il10$^{venus}$ mice.

Moreover, lymphocytes in the colonic lamina propria were isolated from $Il10^{venus}$ mice, and the expression of T cell receptor β chain (TCRβ) on the surfaces of the cells was detected by FACS. FIG. 20 shows the obtained results (FACS dot-plots obtained when a gate was set on $CD4^+$ cells). Note that each numeric value in FIG. 20 represents the ratio of cells within the corresponding one of regions divided into four.

Figure 21:
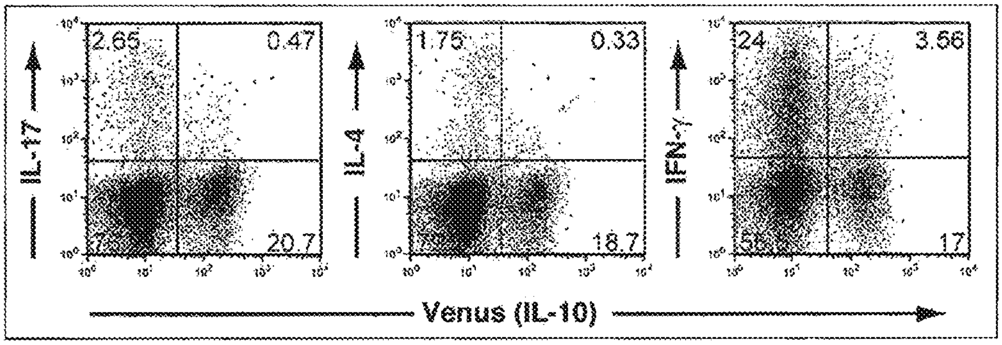
FIG. 21 shows FACS dot-plot diagrams showing analysis results of the expression of IL-17, IL-4, and IFN-γ in lymphocytes isolated from the colonic lamina propria of Il10$^{venus}$ mice.

Furthermore, lymphocytes in the colonic lamina propria were isolated from $Il10^{venus}$ mice. The lymphocytes were stimulated with PMA (50 ng/ml) and ionomycin (1 μg/ml) for four hours in the presence of Golgistop (BD Bioscience) Then, after the stimulation was given, intracellular cytokines were stained by using an anti-IL-17 PE antibody, an anti-IL-4 APC antibody (11B11), and an anti-IFN-g FITC antibody (BD Bioscience) in accordance with the manual of a cytofix/cytoperm kit (BD Bioscience). FIG. 21 shows the obtained results (FACS dot-plots obtained when a gate was set on $CD4^+$ cells).

Note that each numeric value in FIG. 21 represents the ratio of cells within the corresponding one of regions divided into four.

Figure 22:
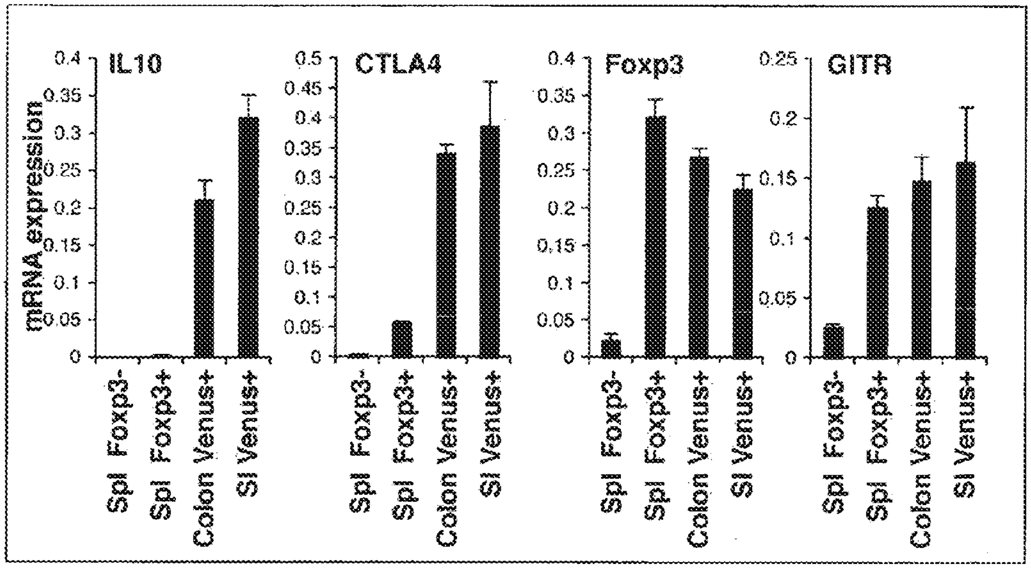
FIG. 22 shows graphs showing analysis results of the amounts of mRNAs of IL-10, CTLA4, Foxp3, and GITR expressed in spleen Foxp3$^-$CD4$^+$ cells, spleen Foxp3$^+$ CD4$^+$ cells, colonic lamina propria Venus$^+$ cells, and small intestinal lamina propria Venus$^+$ cells.

In addition, $Foxp3^+$ $CD4^+$ cells and $Foxp3^-$ $CD4^+$ cells were isolated from the spleen (Spl) of $Foxp3^{eGFP}$ reporter mice, and $Venus^+$ cells were isolated from the colonic lamina propria and the small intestine (SI) lamina propria of $Il10^{venus}$ mice. Then, the obtained cells were analyzed in terms of the expression of predetermined genes. The gene expression was analyzed by real-time RT-PCR using a Power SYBR Green PCR Master Mix (Applied Biosystems) and an ABI 7300 real time PCR system (Applied Biosystems). Here, the value for each cell was normalized for the amount of GAPDH. FIG. 22 shows the obtained results. Note that in FIG. 22 the error bars represent standard deviations.

As is apparent from the results shown in FIGS. 19 to 22, almost no $Venus^+$ cells (IL-10-producing cells) were detected in the cervical lymph nodes (peripheral lymph nodes), *thymus*, peripheral blood, lung, and liver of mice kept under the SPF conditions. Meanwhile, in the spleen, Peyer's patches, and mesenteric lymph nodes thereof, $Venus^+$ cells were slightly detected (refer to FIG. 19). On the other hand, many $Venus^+$ cells were found in the lymphocytes in the small intestine lamina propria and colonic lamina propria. In addition, most of the $Venus^+$ cells in the intestines were positive for CD4, and also positive for T cell receptor β chain (TCRβ) (refer to FIGS. 19 and 20). Moreover, it was found that the $Venus^+$ $CD4^+$ T cells expressed Foxp3 and other Treg cell-associated factors such as a cytotoxic T-Lymphocyte antigen (CTLA-4) and a glucocorticoid-induced TNFR-associated protein (GITR) although the $Venus^+$ $CD4^+$ T cells showed none of the phenotypes of Th2 (IL-4-producing) and Th17 (IL-17-producing) (refer to FIGS. 21 and 22). In addition, it was shown that the expression level of CTLA-4 in the intestinal $Venus^+$ cells was higher than that in the splenic $GFP^+$ Treg cells isolated from the $Foxp3^{eGFP}$ reporter mice (refer to FIG. 22).

Example 13

Figure 23:
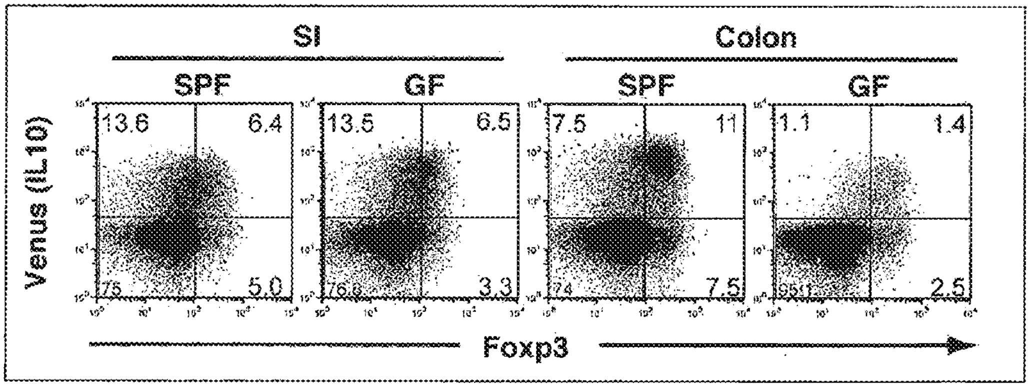
FIG. 23 shows FACS dot-plot diagrams showing analysis results of the expression of CD4, Foxp3, and Venus in the lamina propria of the small intestine and the lamina propria of the colon of GF Il10$^{venus}$ mice and SPF Il10$^{venus}$ mice.

$Venus^+$ cells can be classified into at least two subsets, namely, $Venus^+$ $Foxp3^+$ double positive (DP) Treg cells and $Venus^+$ $Foxp3^-$ Treg cells on the basis of intracellular Foxp3 expression. Cells of the latter subset correspond to type 1 regulatory T cells (Tr1) (refer to Non-Patent Documents 8 and 9). In this respect, the $Venus^+$ cells (IL-10-producing cells) observed in Example 8 were investigated in terms of the expression of Foxp3. Specifically, the expression of CD4, Foxp3, and Venus in the lamina propria of the colon and the lamina propria of the small intestine of $Il10^{venus}$ mice kept under GF or SPF conditions was analyzed by FACS, and the numbers of $Venus^+$ cells in the intestinal tract lamina propria were compared between SPF and GF $Il10^{venus}$ mice. FIG. 23 shows the obtained results (dot-plots obtained when a gate was set on $CD4^+$ cells).

Figure 24:
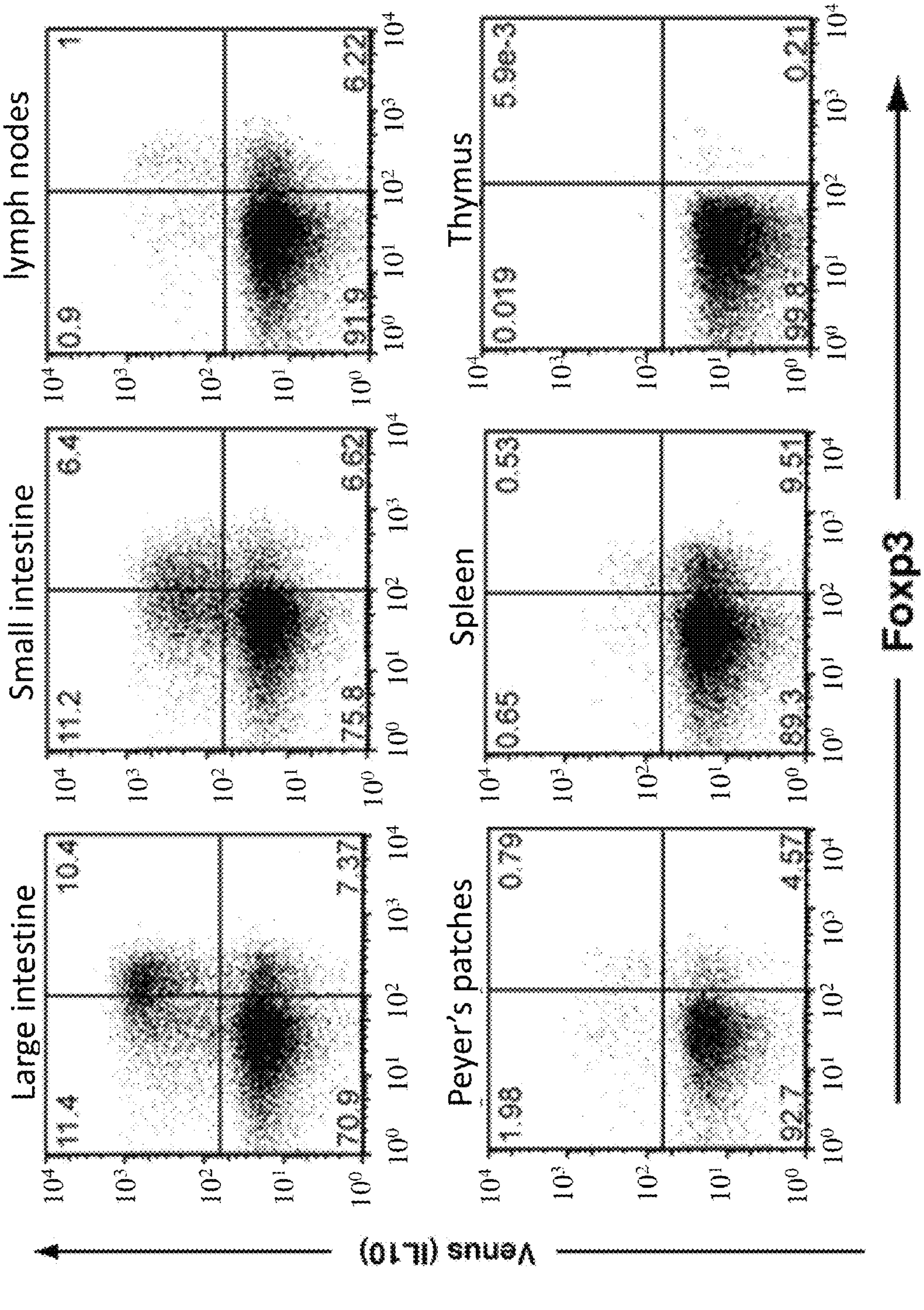
FIG. 24 shows FACS dot-plot diagrams showing analysis results of the expression of Venus and Foxp3 of CD4 cells in various tissues of SPF Il10$^{venus}$ mice.
Figure 24:
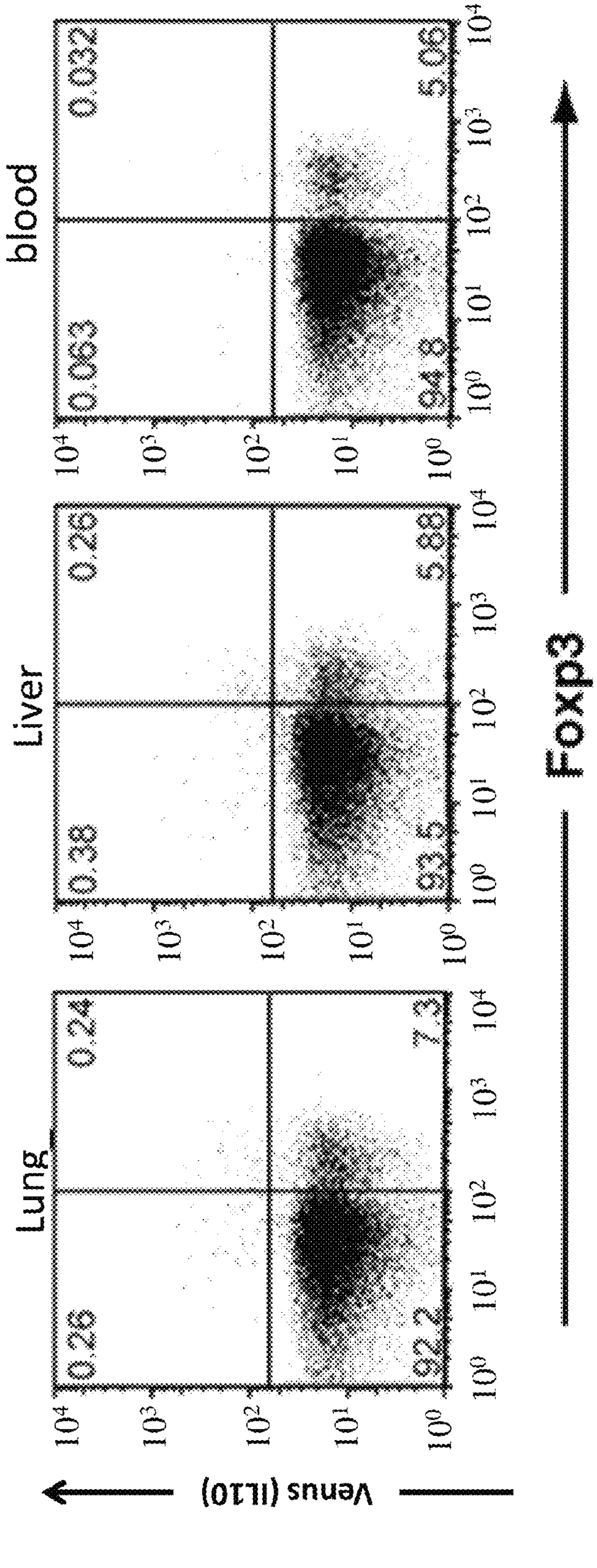

In addition, the intracellular expression of Venus and Foxp3 in CD4 cells in various tissues of SPF $Il10^{venus}$ mice was analyzed by flow cytometry. FIG. 24 shows the obtained results (dot-plots obtained when a gate was set on $CD4^+$ cells). Note that each numeric value in FIG. 24 represents the ratio of cells within the corresponding one of regions divided into four.

Figure 25:
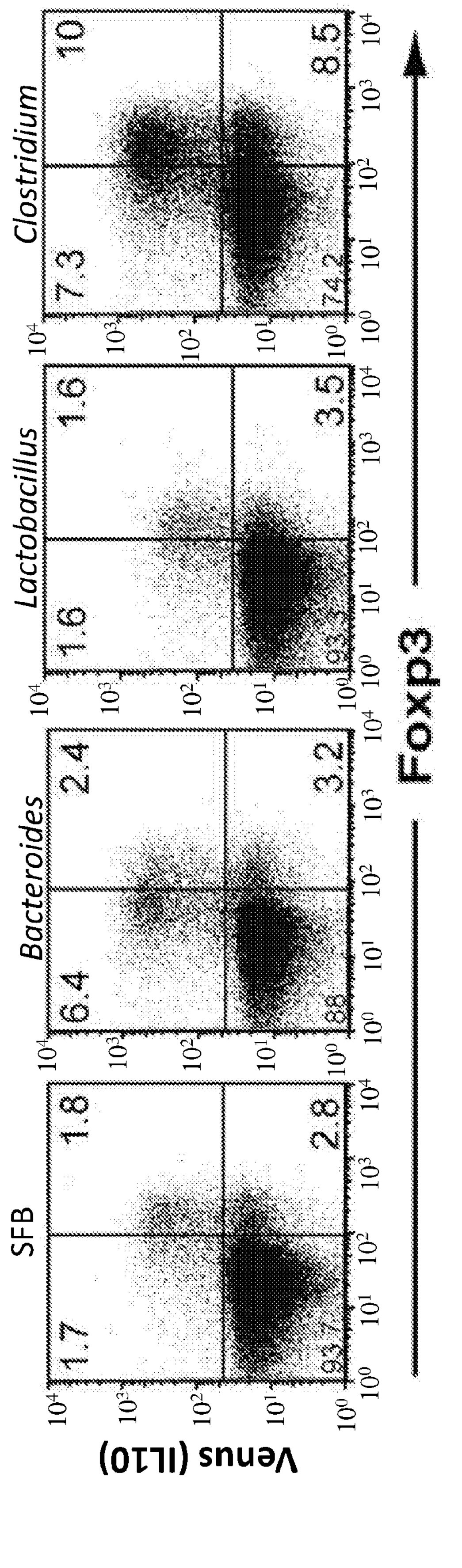
FIG. 25 shows FACS dot-plot diagrams showing analysis results of the expression of Foxp3 and Venus in Il10$^{venus}$ mice in which specific commensal bacteria were colonized.
Figure 26:
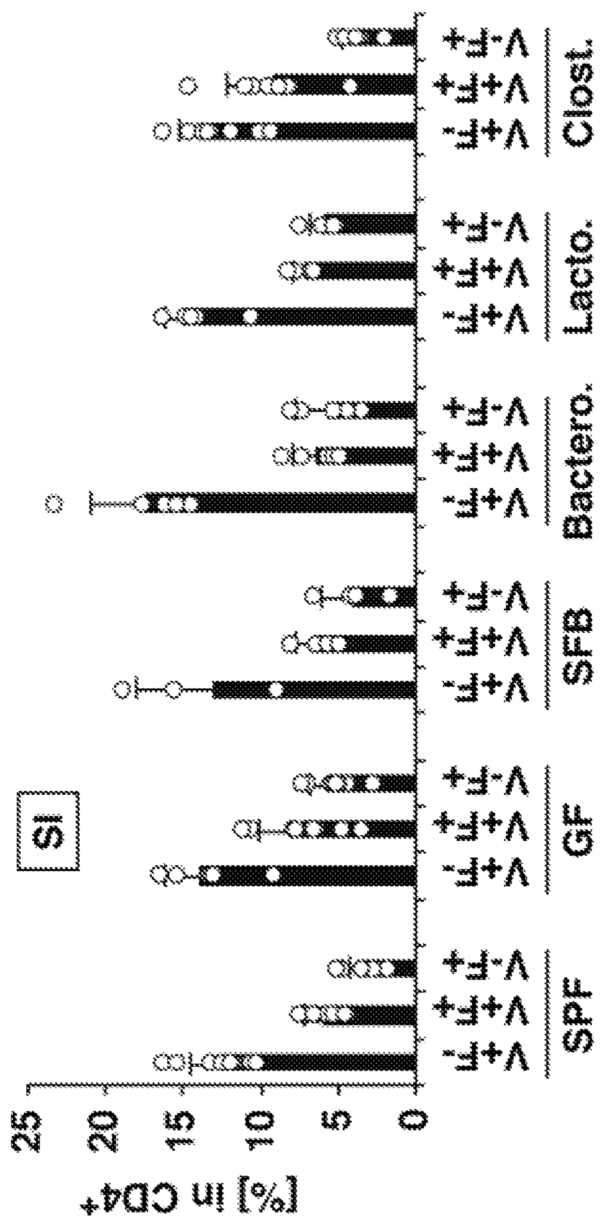
FIG. 26 is a graph showing analysis results of the expression of Foxp3 and/or Venus of CD4$^+$ cells in the small intestine of Il10$^{venus}$ mice in which specific commensal bacteria were colonized.
Figure 27:
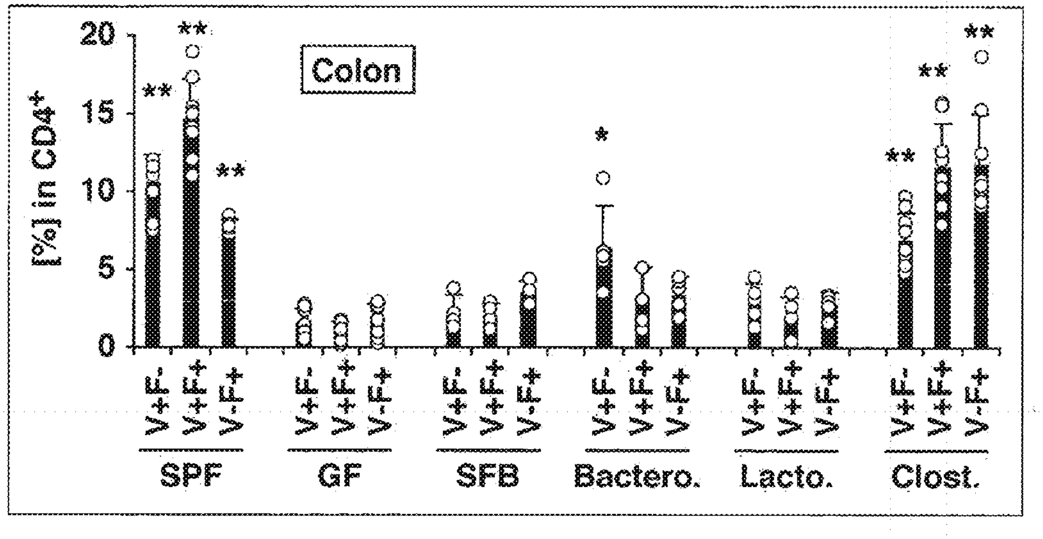
FIG. 27 is a graph showing analysis results of the expression of Foxp3 and/or Venus of CD4$^+$ cells in the colon of Il10$^{venus}$ mice in which specific commensal bacteria were colonized.

Moreover, in order to investigate whether or not the presence of commensal bacteria had any influence on the expression of IL-10 in regulatory cells in the gastrointestinal tracts, germ-free (GF) $Il10^{venus}$ mice were prepared. Then, predetermined species of bacteria were caused to be colonized in the obtained GF $Il10^{venus}$ mice. Three weeks after the species of bacteria were colonized, a $CD4^+$ cell group ($V^+F^-$, $Venus^+$ $Foxp3^-$ cells; $V^+F^+$, $Venus^+$ $Foxp3^+$ cells; and $V^-F^+$, $Venus^-Foxp3^+$ cells) in which Foxp3 and/or Venus were expressed in the colon and the small intestine was analyzed by flow cytometry. FIG. 25 shows dot-plots obtained when a gate was set on colonic $CD4^+$ cells, and FIGS. 26 and 27 show the ratios in the $CD4^+$ cell group of each mouse. Note that each numeric value in FIG. 25 represents the ratio of cells within the corresponding one of regions divided into four. Meanwhile, the error bars in FIGS. 26 and 27 represent standard deviations, * indicates that "P<0.02," and ** indicates that "P<0.001."

Moreover, in order to check whether or not the presence of commensal bacteria had any influence on the expression of IL-10 in regulatory cells in the gastrointestinal tracts, antibiotics were orally given with water to five or six $Il10^{venus}$ mice per group for 10 weeks. The following antibiotics were used in combination.

ampicillin (A; 500 mg/L Sigma)
vancomycin (V; 500 mg/L NACALAI TESQUE, INC.)
metronidazole (M; 1 g/L NACALAI TESQUE, INC.)
neomycin (N; 1 g/L NACALAI TESQUE, INC.)

Figure 28:
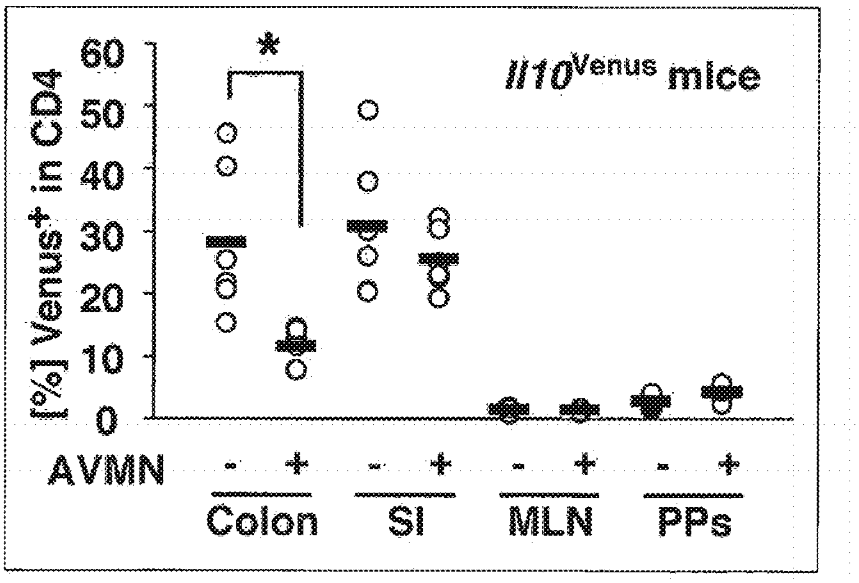
FIG. 28 is a plot diagram showing analysis results of the ratios of Venus$^+$ cells in CD4$^+$ cells isolated from various tissues of Il10$^{venus}$ mice treated with antibiotics.

Then, CD4 and Foxp3 of lymphocytes in the lamina propria of the colon, the lamina propria of the small intestine (SI), mesenteric lymph nodes (MLN), and Peyer's patches (PPs) were stained with antibodies, and analyzed by FACS. The results were obtained from two or more independent experiments which gave similar results. FIG. 28 shows the obtained results (the ratio of $Venus^+$ cells in $CD4^+$ cells in each sample). Note that each white circle in FIG. 28 represents an individual sample, each horizontal bar represents an average value, * indicates that "P<0.02," and "AVMN" represents the kinds of the administered antibiotics by using the first letters of the antibiotics.

As is apparent from the results shown in FIGS. 23 and 24, it was shown that the small intestinal lamina propria was rich in $Venus^+$ $Foxp3^-$ cells, namely, Tr1-like cells, and that the Venus+ $Foxp3^+$ DP Treg cells were present at a high frequency in the colon of the SPF mice (refer to FIGS. 23 and 24). In contrast, although sufficient numbers of $Foxp3^+$ cells were observed also in other tissues, the expression of Venus was not observed in almost all of the cells (refer to FIG. 24).

In addition, as is apparent from the results shown in FIGS. 23 and 25 to 28, it was shown that all regulatory T cell fractions of $Venus^+$ $Foxp3^-$, $Venus^+$ $Foxp3^+$, and $Venus^-$ $Foxp3^+$ in the colon significantly decreased under the GF conditions (FIGS. 23 and 26 to 27). Moreover, similar decrease in $Venus^+$ cells was observed also in the SPF $Il10^{venus}$ mice treated with the antibiotics (refer to FIG. 28).

Moreover, as is apparent from the results shown in FIGS. 25 to 27, the colonization of *Clostridium* spp. strongly induced all regulatory T cell fractions of $Venus^+$ $Foxp3^-$, $Venus^+$ $Foxp3^+$, and $Venus^-$ $Foxp3^+$ in the colon, and the degrees of the induction thereof were equal to those in the SPF mice (refer to FIGS. 25 and 27). In addition, it was found that the colonization of the three strains of *Lactobacillus* or the colonization of SFB had an extremely small influence on the number of $Venus^+$ and/or $Foxp3^+$ cells in the colon (refer to FIGS. 25 and 27). Moreover, the colonization of 16 strains of *Bacteroides* spp. also induced $Venus^+$ cells, but the influence of the colonization was specific to $Venus^+$ $Foxp3^-$ Tr1-like cells (refer to FIGS. 25 and 27). On the other hand, it was found that none of the bacterial species tested exerted any significant influence on the number of IL-10-producing cells in the small intestinal lamina propria (refer to FIG. 26).

Hence, it was shown that the genus *Clostridium* colonized in the colon or a physiologically active substance derived from the bacteria provided a signal for inducing the accumulation of $IL-10^+$ regulatory T cells in the colonic lamina propria or the expression of IL-10 in T cells. Meanwhile, it was shown that the number of $Venus^+$ cells in the small intestine was not significantly influenced by the situation where no commensal bacteria were present or commensal bacteria were decreased (refer to FIGS. 23 and 26 to 28), and that $IL-10^+$ regulatory cells (Tr1-like cells) accumulated in the small intestinal lamina propria independently of commensal bacteria.

Example 14

It was investigated whether or not $Venus^+$ cells induced by the genus *Clostridium* had an immunosuppressive function similar to that of $Venus^+$ cells in the colon of SPF mice. Specifically, $CD4^+$ $CD25^-$ cells (effector T cells, Teff cells) isolated from the spleen were seeded in a flat-bottomed 96-well plate at $2\times10^4$/well, and cultured for three days together with $2\times10^4$ splenic $CD11c^+$ cells (antigen-representing cells) subjected to 30 Gy radiation irradiation treatment, 0.5 μg/ml of an anti-CD3 antibody, and a lot of Treg cells. In addition, for the last six hours, the $CD4^+$ $CD25^-$ cells were cultured, with [$^3$H]-thymidine (1 μCi/well) was added thereto. Note that, Treg cells used in Example 14 were $CD4^+$ $GFP^+$ T cells isolated from the spleen of $Foxp3^{eGFP}$ reporter mice, or $CD4^+$ $Venus^+$ T cells in the colonic lamina propria of GF $Il10^{venus}$ mice in which *Clostridium* spp. were colonized or SPF $Il10^{venus}$ mice. Then, proliferation of the cells was determined based on the uptake amount of [$^3$H]-thymidine, and represented by a count per minute (cpm) value.

Figure 29:
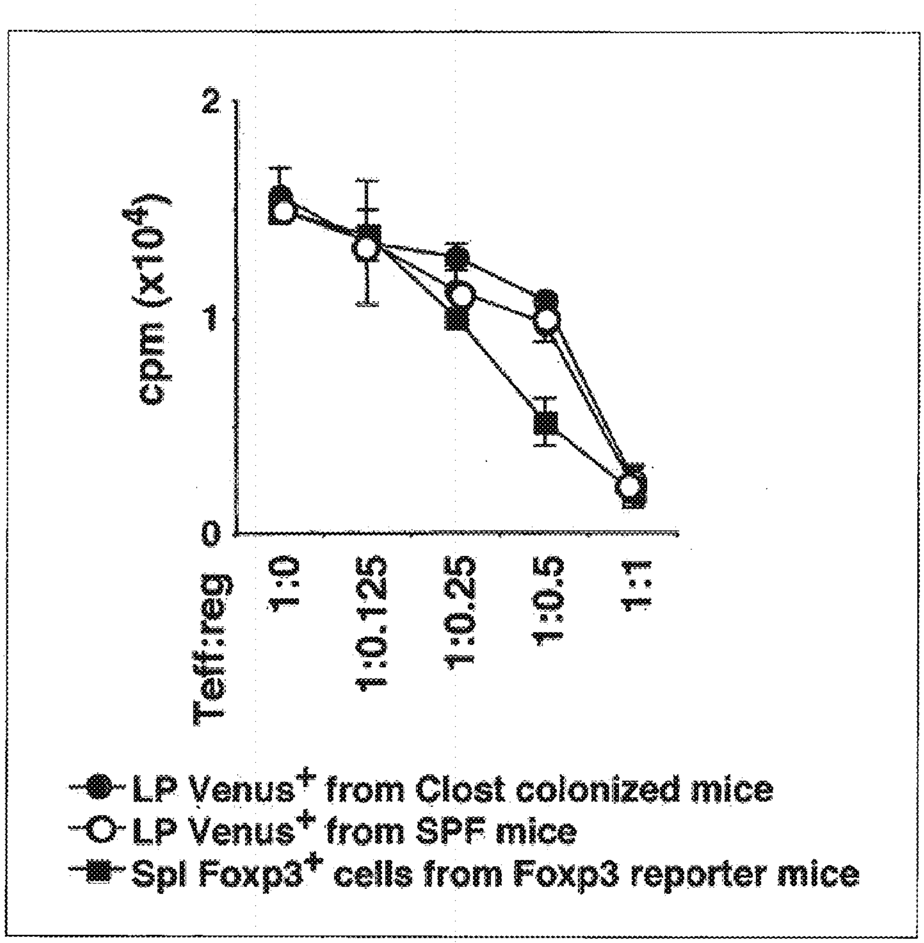
FIG. 29 is a graph showing analysis results of immunoregulatory functions of CD4 Venus$^+$ cells from the colonic lamina propria of GF Il10$^{venus}$ mice in which the genus *Clostridium* was colonized, CD4$^+$ Venus$^+$ cells from the colonic lamina propria of SPF Il10$^{venus}$ mice, and CD4$^+$ GFP$^+$ cells from the spleen of Foxp3$^{eGFP}$ reporter mice.

As is apparent from the results shown in FIG. 29, Venus$^+$ CD4$^+$ cells of the mice in which the genus *Clostridium* was colonized suppressed in vitro proliferation of CD25$^-$ CD4$^+$ activated T cells. The suppression activity was slightly inferior to that of GFP$^+$ cells isolated from the Foxp3$^{eGFP}$ reporter mice, but equal to that of Venus$^+$ cells isolated from the SPF Il10$^{venus}$ mice. Accordingly, it has been shown that the genus *Clostridium* induces IL-10-expressing T cells having sufficient immunosuppressive activities, and thereby plays a critical role in maintaining immune homeostasis in the colon.

Example 15

Next, the influence, on the local immune response, of the colonization of a large number of *Clostridium* and the resultant proliferation of Treg cells was investigated.

<Dextran Sulfate Sodium (DSS)-Induced Colitis Model>

Figure 41:
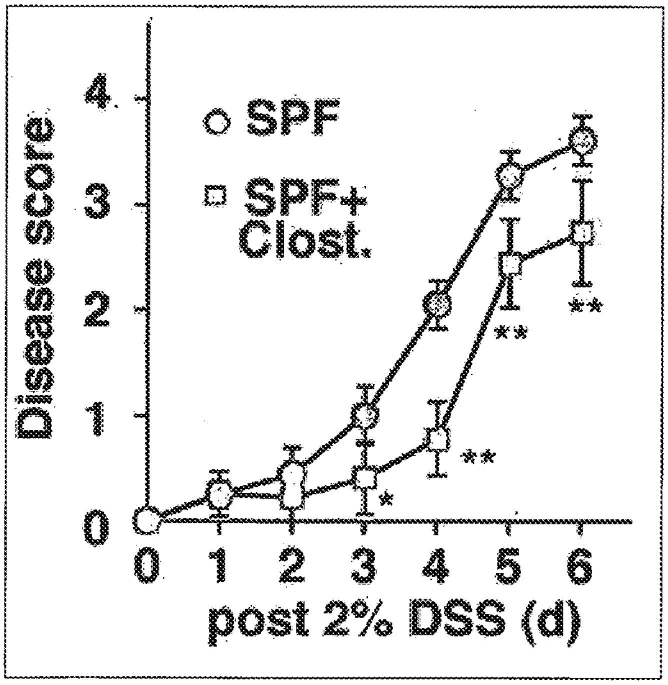
FIG. 41 is a graph showing the results obtained when control mice (SPF) and *Clostridium*-administered mice (SPF+*Clost.*) were treated with 2% DSS, observed and measured for the body weight loss, the hardness of stool, and bleeding for six days, and then evaluated numerically.
Figure 42:
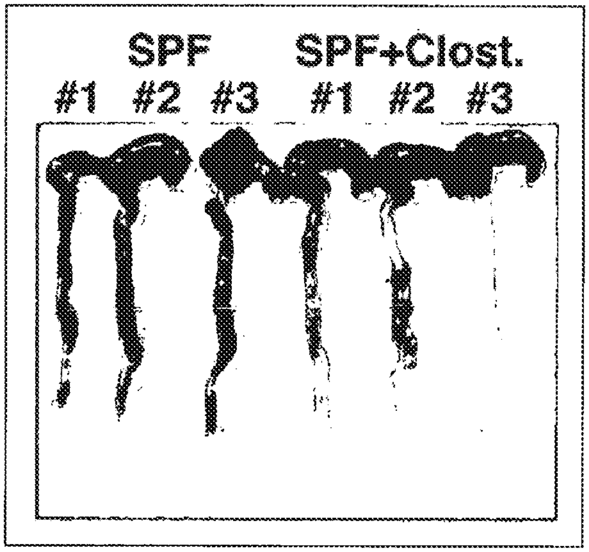
FIG. 42 is a photograph showing the state of the colons collected on day 6 after the control mice (SPF) and the *Clostridium*-administered mice (SPF+*Clost.*) were treated with 2% DSS.
Figure 43:
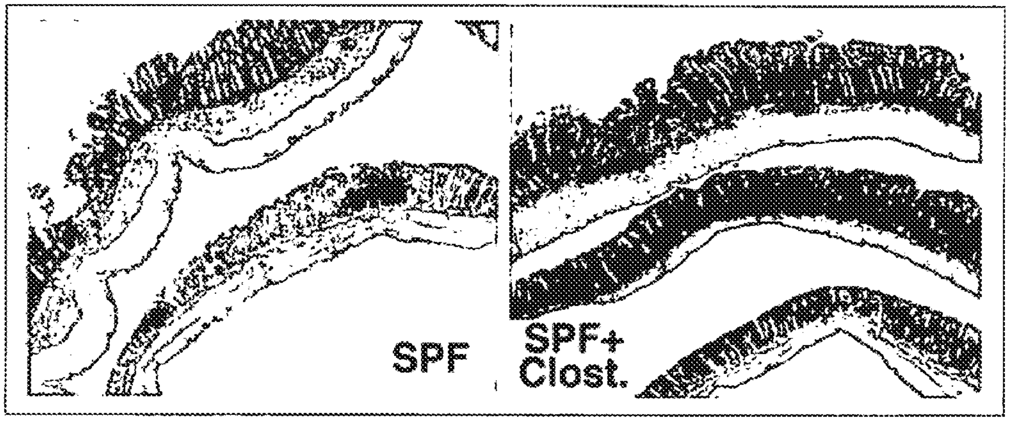
FIG. 43 shows photomicrographs showing the results obtained when the control mice (SPF) and the *Clostridium*-administered mice (SPF+*Clost.*) were treated with 2% DSS, and the colons thereof were collected on day 6 and analyzed histologically by HE staining.

First, the DSS-induced colitis model was prepared as described above, and the influence, on the model mice, of the inoculation of the *Clostridium* and the proliferation of Treg cells was investigated. Specifically, control mice and *Clostridium*-inoculated mice were treated with 2% DSS, then observed and measured for six days for the body weight loss, the hardness of stool, and bleeding, and then were evaluated numerically. In addition, on day 6, the colons were collected, dissected, and analyzed histologically by HE staining. FIGS. 41 to 43 show the obtained results. Note that, in FIGS. 41 to 43, "SPF+*Clost.*" or "SPF+*Clost.*#1 to 3" indicate the results of C57BL/6 mice inoculated with a fecal suspension of *Clostridium*-colonized mice, and grown in a conventional environment for six weeks, and "SPF" or "SPF#1 to 3" indicate the results of C57BL/6 mice (control mice) grown in a conventional environment for six weeks without being inoculated with the fecal suspension. In addition, in FIG. 41, the vertical axis "Disease score" represents the disease activity index (DAI) described above, and the horizontal axis "post 2% DSS(d)" represents the days elapsed after the initial administration of 2% DSS to the mice. Moreover, in FIG. 41, * indicates that "P<0.02," and ** indicates that "P<0.001." Meanwhile, Treg cells induced by regulatory dendritic cells are known to play a preventive role in a DSS-induced colitis model (see S. Manicassamy et al., Science 329, 849 (Aug. 13, 2010)).

As is apparent from the results shown in FIGS. 41 to 43, the symptoms of the colitis such as body weight loss and rectal bleeding were significantly suppressed in the mice having a large number of *Clostridium* (hereinafter also referred to as "*Clostridium*-abundant mice") in comparison with the control mice (see FIG. 41). All the features typical for colonic inflammation, such as shortening of the colon, edema, and hemorrhage, were observed markedly in the control mice in comparison with the *Clostridium*-abundant mice (see FIG. 42). Moreover, histological features such as mucosal erosion, edema, cellular infiltration, and crypt loss were less severe in the DSS-treated *Clostridium*-abundant mice than in the control mice (see FIG. 43).

<Oxazolone-Induced Colitis Model>

Figure 44:
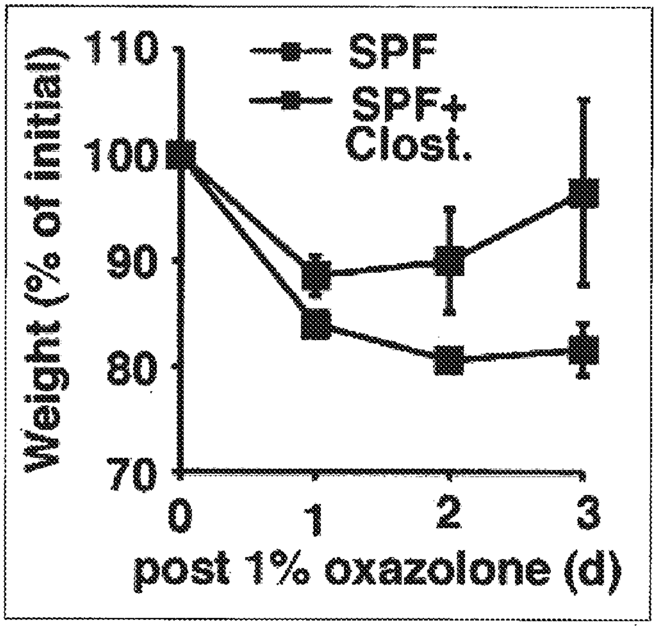
FIG. 44 is a graph showing the results obtained when control mice (SPF) and *Clostridium*-administered mice (SPF+*Clost.*) were sensitized with oxazolone, and subsequently the inside of each rectum was treated with a 1% oxazolone/50% ethanol solution, and the body weight loss was measured.
Figure 45:
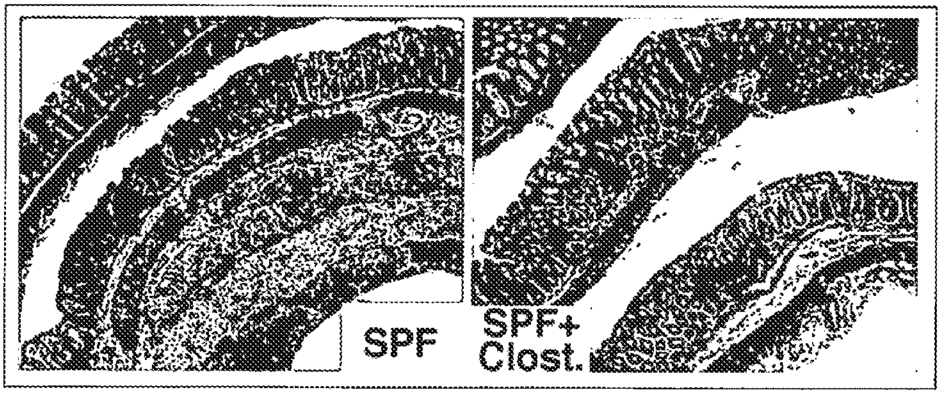
FIG. 45 shows photomicrographs showing the results obtained when the control mice (SPF) and the *Clostridium*-administered mice (SPF+*Clost.*) were sensitized with oxazolone, and subsequently the inside of each rectum was treated with a 1% oxazolone/50% ethanol solution, and the colons obtained by the treatment were analyzed histologically by HE staining.

Next, the oxazolone-induced colitis model was prepared as described above, and the influence, on the model mice, of the inoculation of *Clostridium* and the proliferation of Treg cells was investigated. Specifically, control mice and *Clostridium*-inoculated mice were sensitized with oxazolone, and subsequently the inside of the rectums thereof were treated with a 1% oxazolone/50% ethanol solution. Then, the body weight loss was observed and measured. In addition, the colons were dissected, and analyzed histologically by HE staining. FIGS. 44 and 45 show the obtained results. Note that, in FIGS. 44 and 45, "SPF+*Clost.*" indicates the results of C57BL/6 mice (*Clostridium*-abundant mice) inoculated with a fecal suspension of *Clostridium*-colonized mice, and grown in a conventional environment for six weeks, and "SPF" indicates the results of C57BL/6 mice (control mice) grown in a conventional environment for six weeks without being inoculated with the fecal suspension. In addition, in FIG. 44, the vertical axis "Weight (% of initial)" represents the body weight after the administration of 1% oxazolone where the body weight before the administration was taken as 100%, and the horizontal axis "post 1% oxazolone (d)" represents the days elapsed after the administration of 1% oxazolone to the mice. Meanwhile, it is known that Th2-type T cells are involved in colitis induced by oxazolone. (see M. Boirivant, I. J. Fuss, A. Chu, W. Strober, J Exp Med 188, 1929 (Nov. 16, 1998)).

As is apparent from the results shown in FIGS. 44 and 45, the colitis proceeded along with persistent body weight loss in the control mice. Meanwhile, the body weight loss of the *Clostridium*-abundant mice was reduced (see FIG. 44). In addition, it was also revealed that portions having histological diseases such as mucosal erosion, edema, cellular infiltration, and hemorrhage were reduced in the colon of the *Clostridium*-abundant mice (see FIG. 45).

Example 16

Figure 46:
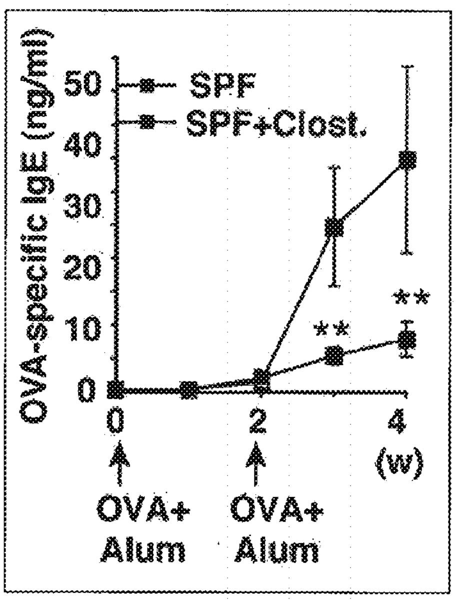
FIG. 46 is a graph showing the results obtained when control mice (SPF) and *Clostridium*-administered mice (SPF+*Clost.*) were immunized by administering alum-absorbed ovalbumin (OVA) twice at a 2-week interval, and the sera were collected therefrom and analyzed for the concentration of OVA-specific IgE in these sera by ELISA.
Figure 47:
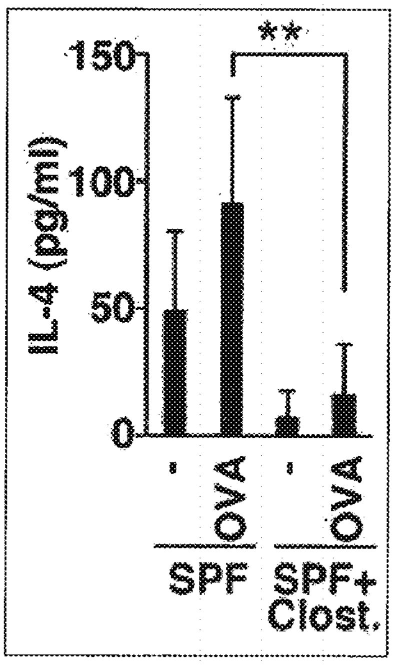
FIG. 47 is a graph showing the results obtained when the control mice (SPF) and the *Clostridium*-administered mice (SPF+*Clost.*) were immunized by administering the alum-absorbed OVA twice at a 2-week interval, and splenic cells were collected and analyzed for IL-4 production of these splenic cells by in-vitro OVA restimulation.
Figure 48:
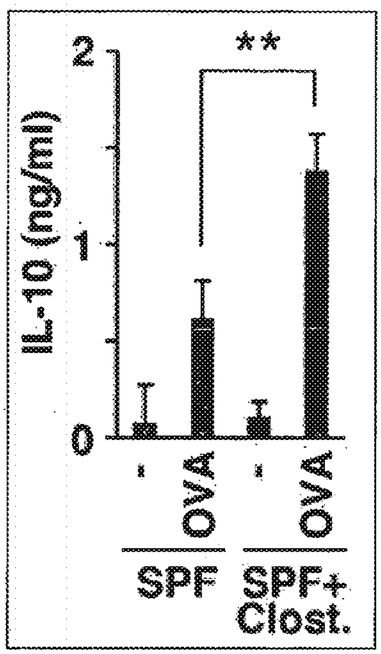
FIG. 48 is a graph showing the results obtained when the control mice (SPF) and the *Clostridium*-administered mice (SPF+*Clost.*) were immunized by administering the alum-absorbed OVA twice at a 2-week interval, and the splenic cells were collected and analyzed for IL-10 production of these splenic cells by the in-vitro OVA restimulation.

Next, the influence, on the systemic immune response (systemic IgE production), of the colonization of a large number of *Clostridium* and the resultant proliferation of Treg cells was investigated. Specifically, as described above, control mice and *Clostridium*-inoculated mice were immunized by administering alum-absorbed ovalbumin (OVA) twice at a 2-week interval. Then, sera were collected from these mice, and the OVA-specific IgE level thereof was investigated by ELISA. In addition, splenic cells were collected from the mice in each group, and IL-4 and IL-10 production by in-vitro OVA restimulation was investigated. FIGS. 46 to 48 show the obtained results. Note that, in FIGS. 46 to 48, "SPF+*Clost.*" indicates the results of BALB/c SPF mice (*Clostridium*-abundant mice) inoculated with a fecal suspension of *Clostridium*-colonized mice, and grown in a conventional environment, "SPF" indicates the results of BALB/c SPF mice (control mice) grown in a conventional environment without being inoculated with the fecal suspension, and  indicates that "P<0.001." Meanwhile, in FIG. 46, the vertical axis "OVA-specific IgE (ng/ml)" represents the concentration of OVA-specific IgE in the sera. Moreover, in FIG. 46**, the horizontal axis represents the days elapsed after the initial administration of the alum-absorbed ovalbumin to the *Clostridium*-abundant mice or the control mice (4-week old), and "OVA+Alum" indicates the timing of the administration of the alum-absorbed ovalbumin. In addition, in FIGS. 47 and 48, "OVA" on the horizontal axis indicates the results in the case where the in-vitro OVA restimulation was performed, and "-" indicates the results in the case where no in-vitro OVA restimulation was performed. Moreover, in FIGS. 47 and 48, the vertical axes "IL-4 (pg/ml)" and "IL-10 (pg/ml)" show the IL-4 concentration and the IL-10 concentration in culture supernatants of splenic cells, respectively.

As is apparent from the results shown in FIGS. 46 to 48, the IgE level was significantly lower in the *Clostridium*-abundant mice than in the control mice (see FIG. 46). Moreover, the IL-4 production by the OVA restimulation was reduced (see FIG. 47) and the IL-10 production thereby was increased (see FIG. 48) in the splenic cells of the *Clostridium*-abundant mice sensitized with OVA and alum, in comparison with those of the control mice.

Accordingly, in consideration of the results shown in Example 15 in combination, it has been revealed that the induction of Treg cells by *Clostridium* in the colon plays an important role in local and systemic immune responses.

Example 17

Figure 49:
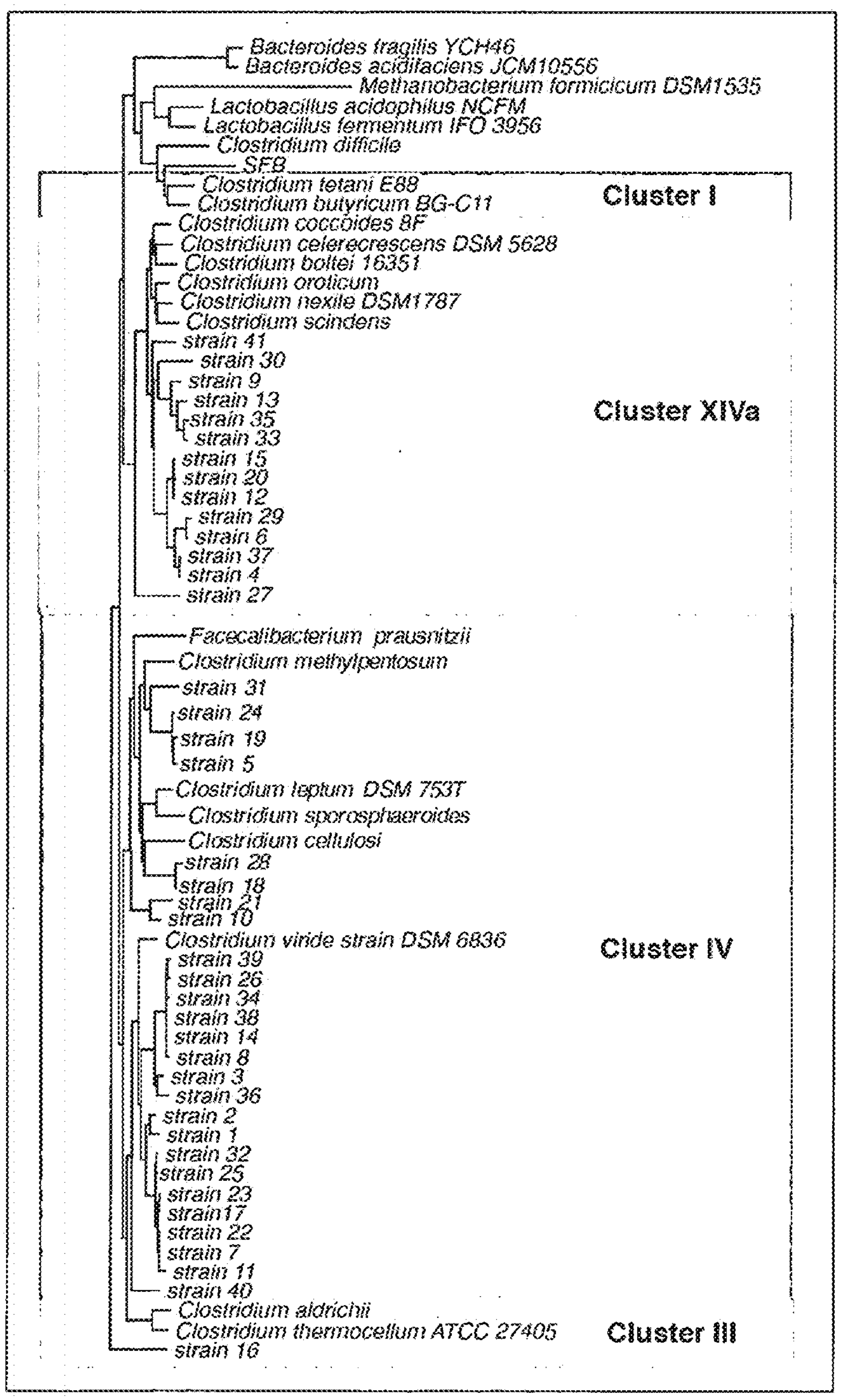
FIG. 49 is Phylogenetic tree constructed by the neighbor-joining method with the resulting sequences of the 41 strains of *Clostridium* and those of known bacteria obtained from Genbank database using Mega software.
Figure 50:
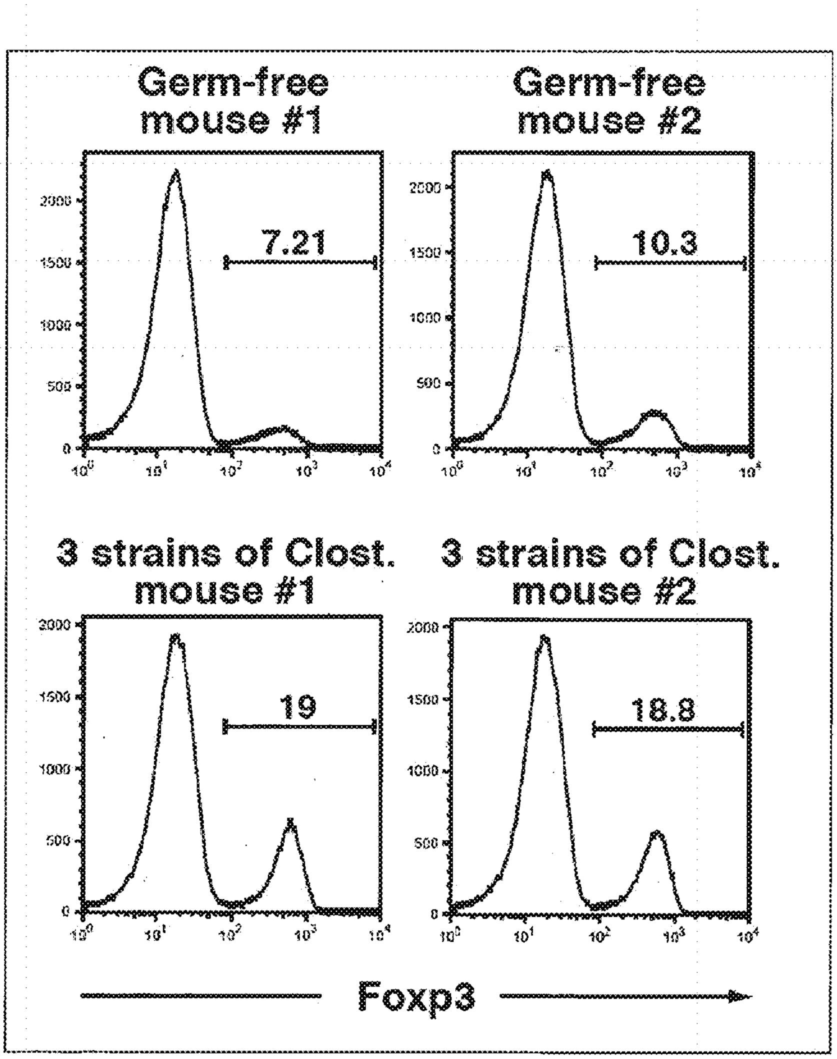
FIG. 50 is histograms showing Foxp3 expression gated CD4 cells from GF mice (Germ-free mouse #1 and #2) or GF mice colonized with three strains of *Clostridium* belonging to cluster IV (3 strains of *Clost.* mouse #1 and #2).

Next, GF Balb/c were colonized with three strains of *Clostridium* belonging to cluster IV (strains 22, 23 and 32 listed in FIG. 49). Three weeks later, colonic $Foxp3^+$ Treg cells were analyzed by FACS. FIG. 50 shows the obtained results. As is apparent from the results shown in FIG. 50, gnotobiotic mice colonized with three strains of *Clostridium* showed an intermediate pattern of Treg induction between GF mice and mice inoculated with all 46 strains.

Example 18

Next, it was investigated whether or not a spore-forming (for example, a chloroform resistant) fraction of a fecal sample obtained from humans had the effect of inducing proliferation or accumulation of regulatory T cells similar to the spore-forming fraction of the fecal sample obtained from mice.

Figure 51:
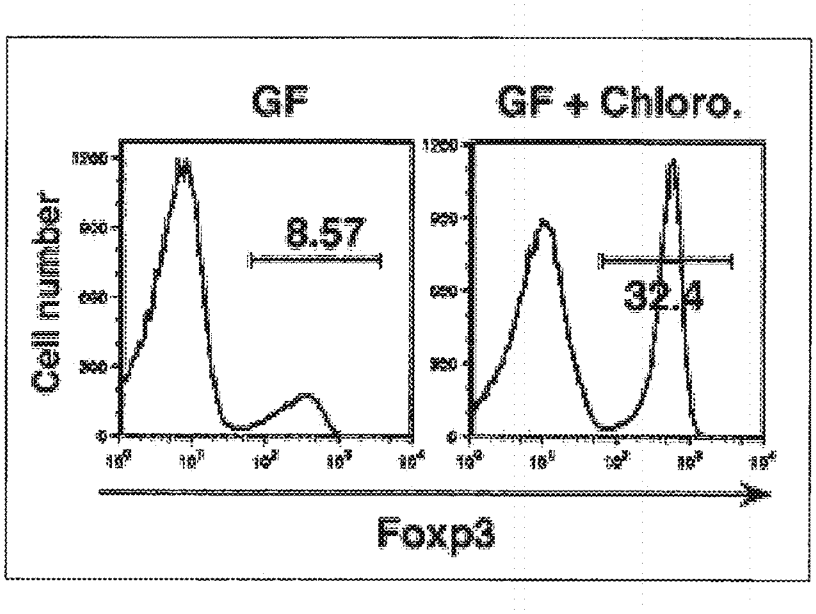
FIG. 51 is histograms showing Foxp3 expression by CD4 positive lymphocytes from GF mice (GF) or GF mice gavaged with chloroform-treated human stool (GF+Chloro.).
Figure 52:
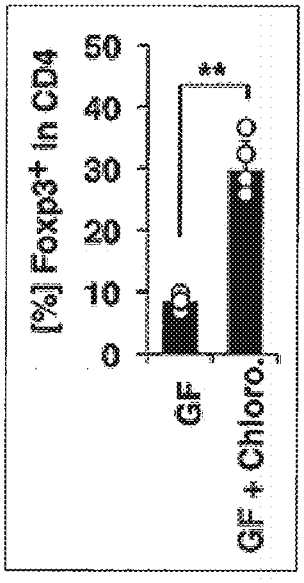
FIG. 52 is a graph showing Foxp3 expression by CD4 positive lymphocytes from GF mice (GF) or GF mice gavaged with chloroform-treated human stool (GF+Chloro.).

Specifically, human stool from a healthy volunteer (Japanese, male, 29 years old) was suspended with phosphate-buffered saline (PBS), mixed with chloroform (final concentration 3%), and then incubated in a shaking water bath for 60 min. After evaporation of chloroform by bubbling with $N_2$ gas, the aliquots containing chloroform-resistant (for example, spore-forming) fraction of human intestinal bacteria were orally inoculated into germ-free (GF) mice (IQI, 8 weeks old). The treated mice were kept in a vinyl isolator for 3 weeks. The colon was collected and opened longitudinally, washed to remove fecal content, and shaken in Hanks' balanced salt solution (HBSS) containing 5 mM EDTA for 20 min at 37° C. After removing epithelial cells and fat tissue, the colon was cut into small pieces and incubated with RPMI1640 containing 4% fetal bovine serum, 1 mg/ml collagenase D, 0.5 mg/ml dispase and 40 μg/ml DNase I (all manufactured by Roche Diagnostics) for 1 hour at 37° C. in a shaking water bath. The digested tissue was washed with HBSS containing 5 mM EDTA, resuspended in 5 ml of 40% Percoll (manufactured by GE Healthcare) and overlaid on 2.5 ml of 80% Percoll in a 15-ml Falcon tube. Percoll gradient separation was performed by centrifugation at 780 g for 20 min at 25° C. The interface cells were collected and suspended in staining buffer containing PBS, 2% FBS, 2 mM EDTA and 0.09% $NaN_3$ and stained for surface CD4 with Phycoerythrin-labeled anti-CD4 Ab (RM4-5, manufactured by BD Biosciences) Intracellular staining of Foxp3 was performed using the Alexa647-labeled anti-Foxp3 Ab (FJK-16s, manufactured by eBioscience) and Foxp3 Staining Buffer Set (manufactured by eBioscience). The percentage of Foxp3 positive cells within the CD4 positive lymphocyte population was analyzed by flow cytometry. FIGS. 51 and 52 show the obtained results.

In figures, representative histograms (FIG. 51) and combined data (FIG. 52) for Foxp3 expression by CD4 positive lymphocytes from GF mice (GF) or GF mice gavaged with chloroform-treated human stool (GF+Chloro.) are shown. In addition, numbers in FIG. 51 indicate the percentages of cells in the gate. Each circle in FIG. 52 represents a separate animal, error bars indicate the SD, and ** indicates that "P<0.001."

As is apparent from the results shown in FIGS. 51 and 52, it was found that also when the spore-forming (for example, the chloroform resistant) fraction of human intestinal bacteria was colonized in GF mice, the accumulation of $Foxp3^+$ regulatory (Treg) cells in the colonic lamina propria of the mice was induced.

Next, it was investigated what species of bacteria grew by gavaging with chloroform-treated human stool.

Specifically, using a QIAamp DNA Stool mini kit (manufactured by QIAGEN), bacterial genomic DNA was isolated from the human stool from a healthy volunteer as described above (human stool) or fecal pellets from GF mice gavaged with chloroform-treated human stool (GF+Chloro.). Quantitative PCR analysis was carried out using a LightCycler 480 (manufactured by Roche). Relative quantity was calculated by the ΔCt method and normalized to the amount of total bacteria, dilution, and weight of the sample. The following primer sets were used:

```
total bacteria
                                        (SEQ ID NO: 62)
5'-GGTGAATACGTTCCCGG-3'
and
                                        (SEQ ID NO: 63)
5'-TACGGCTACCTTGTTACGACTT-3'

Clostridium cluster XIVa
(Clostridium coccoides subgroup)
                                        (SEQ ID NO: 64)
5'-AAATGACGGTACCTGACTAA-3'
and
                                        (SEQ ID NO: 65)
5'-CTTTGAGTTTCATTCTTGCGAA-3'

Clostridium cluster IV (Clostridium leptum)
                                        (SEQ ID NO: 66)
5'-GCACAAGCAGTGGAGT-3'
and
                                        (SEQ ID NO: 67)
5'-CTTCCTCCGTTTTGTCAA-3'

Bacteroides
                                        (SEQ ID NO: 68)
5'-GAGAGGAAGGTCCCCCAC-3'
and
                                        (SEQ ID NO: 69)
5'-CGCTACTTGGCTGGTTCAG-3'.
```

Figure 53:
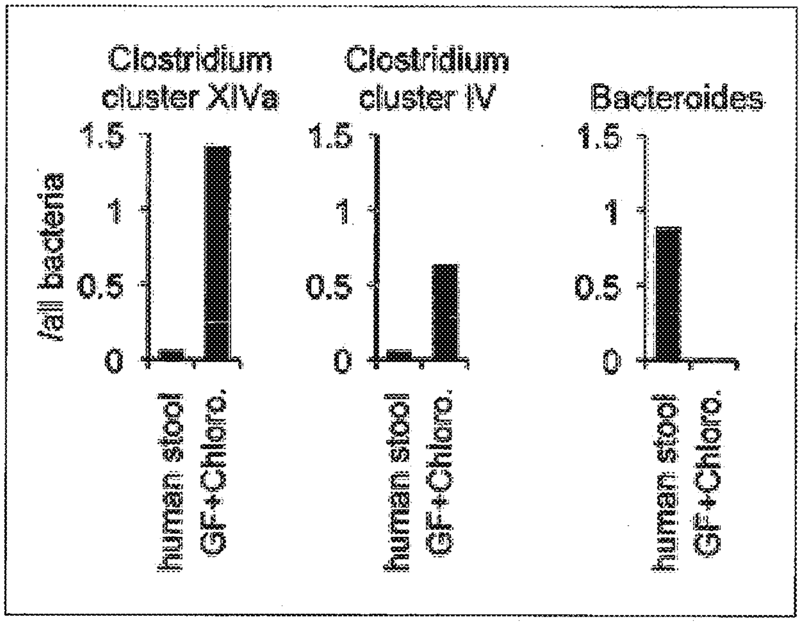
FIG. 53 is a graph showing amounts of *Clostridium* and *Bacteroides* in feces of mice gavaged with chloroform-treated human stool

FIG. 53 shows the obtained results.

As is apparent from the results shown in FIG. 53, mice gavaged with chloroform-treated human stool exhibited high amounts of spore-forming bacteria, such as *Clostridium* clusters XIVa and IV, and a severe decrease of non-spore-forming bacteria, such as *Bacteroides*, compared with the human stool before chloroform treatment.

INDUSTRIAL APPLICABILITY

As has been described above, the present invention makes it possible to provide an excellent composition for inducing proliferation or accumulation of regulatory T cells (Treg cells) by utilizing bacteria belonging to the genus *Clostridium* or a physiologically active substance or the like derived from the bacteria. Since the composition of the present invention has immunosuppressive effects, the composition can be used, for example, to prevent or treat autoimmune diseases or allergic diseases, as well as to suppress immunological rejection in organ transplantation or the like. In addition, healthy individuals can easily and routinely ingest the composition as a food or beverage, such as a health food, to improve their immune functions.

SEQUENCE LISTING

SEQ ID NO:1 to 20, 62 to 69
<223> Artificially synthesized primer sequence
SEQ ID NO:21 to 61
<223>16S rRNA coding gene sequence of each *Clostridium* strain

The invention claimed is:

1. A method of treating a human subject having an infectious disease, an autoimmune disease, or an allergic disease, the method comprising administering a pharmaceutical composition comprising a purified bacterial mixture of at least two live bacterial strains belonging to *Clostridium* clusters IV and/or XIVa to the human subject, wherein the bacterial strains are spore-forming bacteria and are isolated from a human.

2. The method of claim 1, wherein the human subject has an infectious disease.

3. The method of claim 1, wherein the human subject has an allergic disease.

4. The method of claim 1, wherein the at least two live bacterial strains belonging to *Clostridium* clusters IV and/or XIVa comprise two or more strains belonging to *Clostridium* cluster IV.

5. The method of claim 1, wherein the at least two live bacterial strains belonging to *Clostridium* clusters IV and/or XIVa comprise two or more strains belonging to *Clostridium* cluster XIVa.

6. The method of claim 1, wherein the at least two live bacterial strains belonging to *Clostridium* clusters IV and/or XIVa comprise one or more strains belonging to *Clostridium* cluster IV and one or more strains belonging to *Clostridium* cluster XIVa.

7. The method of claim 1, wherein the bacteria are isolated from a chloroform-treated human fecal sample.

8. The method of claim 1, wherein the pharmaceutical composition comprises a pharmaceutically acceptable excipient.

9. The method of claim 1, wherein the pharmaceutical composition is administered orally.

10. The method of claim 1, wherein the pharmaceutical composition is formulated for delivery to the intestine.

11. The method of claim 10, wherein the pharmaceutical composition comprises a pH sensitive composition comprising one or more enteric polymers.

12. The method of claim 10, wherein the pharmaceutical composition is in the form of a capsule.

13. The method of claim 1, wherein the bacteria are in the form of spores.

* * * * *

SEQUENCE LISTING

```
<160> NUMBER OF SEQ ID NOS: 69

<210> SEQ ID NO 1
<211> LENGTH: 23
<212> TYPE: DNA
<213> ORGANISM: Artificial
<220> FEATURE:
<223> OTHER INFORMATION: Artificially synthesized primer sequence

<400> SEQUENCE: 1

ggcaatagtt ccttcccaga gtt                                              23


<210> SEQ ID NO 2
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 2

gggtcgcata ttgtggtact tg                                               22


<210> SEQ ID NO 3
<211> LENGTH: 23
<212> TYPE: DNA
<213> ORGANISM: Artificial
<220> FEATURE:
<223> OTHER INFORMATION: Artificially synthesized primer sequence

<400> SEQUENCE: 3

ccttttgtag ccctgctcac tct                                              23


<210> SEQ ID NO 4
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 4

gggtcacctg tatggcttca g                                                21


<210> SEQ ID NO 5
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 5

tcagtgcaag atctgcaagc a                                                21


<210> SEQ ID NO 6
```

<211> LENGTH: 19
<212> TYPE: DNA
<213> ORGANISM: Artificial
<220> FEATURE:
<223> OTHER INFORMATION: Artificially synthesized primer sequence

<400> SEQUENCE: 6
acaccggaag ccaaacaca 19

<210> SEQ ID NO 7
<211> LENGTH: 27
<212> TYPE: DNA
<213> ORGANISM: Artificial
<220> FEATURE:
<223> OTHER INFORMATION: Artificially synthesized primer sequence

<400> SEQUENCE: 7
gattttaata agctccaaga ccaaggt 27

<210> SEQ ID NO 8
<211> LENGTH: 27
<212> TYPE: DNA
<213> ORGANISM: Artificial
<220> FEATURE:
<223> OTHER INFORMATION: Artificially synthesized primer sequence

<400> SEQUENCE: 8
cttctatgca gttgatgaag atgtcaa 27

<210> SEQ ID NO 9
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 9
cctcgtcccg tagacaaaat g 21

<210> SEQ ID NO 10
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 10
tctccacttt gccactgcaa 20

<210> SEQ ID NO 11
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 11
ggacattgtc tttgatggca 20

<210> SEQ ID NO 12
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 12
cttgtcacgt ggtgtcactg 20

<210> SEQ ID NO 13
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 13
tctctggacg tcaaatgtgg 20

<210> SEQ ID NO 14
<211> LENGTH: 19
<212> TYPE: DNA
<213> ORGANISM: Artificial
<220> FEATURE:
<223> OTHER INFORMATION: Artificially synthesized primer sequence

<400> SEQUENCE: 14
gctgaacagc agagccttc 19

<210> SEQ ID NO 15
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 15
aggtctggat cactccaagg 20

<210> SEQ ID NO 16
<211> LENGTH: 19
<212> TYPE: DNA
<213> ORGANISM: Artificial
<220> FEATURE:
<223> OTHER INFORMATION: Artificially synthesized primer sequence

<400> SEQUENCE: 16
tcgcctggac cataaagaa 19

<210> SEQ ID NO 17
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 17
agaggatgcg tgactttgtg 20

<210> SEQ ID NO 18
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 18
atacagcaga ccttctggca 20

<210> SEQ ID NO 19
<211> LENGTH: 20
<212> TYPE: DNA

<213> ORGANISM: Artificial
<220> FEATURE:
<223> OTHER INFORMATION: Artificially synthesized primer sequence

<400> SEQUENCE: 19
agagtttgat cmtggctcag 20

<210> SEQ ID NO 20
<211> LENGTH: 16
<212> TYPE: DNA
<213> ORGANISM: Artificial
<220> FEATURE:
<223> OTHER INFORMATION: Artificially synthesized primer sequence

<400> SEQUENCE: 20
attaccgcgg ckgctg 16

<210> SEQ ID NO 21
<211> LENGTH: 1460
<212> TYPE: DNA
<213> ORGANISM: Clostridium leptum
<220> FEATURE:
<221> NAME/KEY: rRNA
<222> LOCATION: (1)..(1460)
<223> OTHER INFORMATION: 16S rRNA coding gene sequence of Clostridium strain 1

<400> SEQUENCE: 21
agagtttgat cctggctcag gatgaacgct ggcggcgtgc ttaacacatg caagtcgaac 60
gagaaccatt ggatcgagga ttcgtccaag tgaaggtggg gaaagtggcg gacgggtgag 120
taacgcgtga gcaatctgcc ttggagtggg gaataacggc tggaaacagc cgctaatacc 180
gcatgataca gctgggaggc atctccctgg ctgtcaaaga tttatcgctc tgagatgagc 240
tcgcgtctga ttagctagtt ggcggggtaa cggcccacca aggcgacgat cagtagccgg 300
actgagaggt tggccggcca cattgggact gagacacggc ccagactcct acgggaggca 360
gcagtgggga atattgggca atgggcgcaa gcctgaccca gcaacgccgc gtgaaggaag 420
aaggctttcg ggttgtaaac ttcttttgtc agggacgaag caagtgacgg tacctgacac 480
ggctactacg gtcagcagcg cgtatacgta ggtgccagcg tatccggaat tacctgggtt 540
aaggcgtgtt agccggactg cagtcagatg tgaatcacgg gctcaacttg tgctgcattg 600
gaactgtagt tctgagtact gagagcagac ggaattctag gtagcggtga atgcgtagat 660
ataggaggac acagtgcgag gcgtctgctg acagcaactg acgctgaggc gggaagcgtg 720
ggggagccaa caggattaga tacctggtag ttcacgcctg gtaaaacgat ggatactagg 780
tgtgggggga ctgacccct cgtggccgcc agttaacacc aataaagtat cccacctggg 840
agtacgatcg caaggttgaa actcaaagga attgacgggg cccgcacaag cggtggagta 900
tgtggtttaa ttcgaagcaa cgcgaagaac cttaccaggg cttgacatcc cgaggaccgg 960
actagagata gtcttttctc ttcggagacc tcggtgacag gtggtgcatg gttgtcgtca 1020
gctcgtgtcg taagatgttg ggttaagtcc cgcaacgagc gcaaccctta ttgttagttg 1080
ctacgcaaga gcactctagc gagactgccg ttgacaaaac ggaggaaggt ggggacgacg 1140
tcaaatcatc atgcccctta tgtcctgggc cacacacgta ctacaatggt ggtcaacaga 1200
gggaagcaat accgcgaggt ggagcaaatc cctaaaagcc atcccagttc ggatcgcagg 1260
ctgcaacccg cctgcgtgaa gttggaatcg ctagtaatcg cggatcagca tgccgcggtg 1320
aatacgttcc cgggccttgt acacaccgcc cgtcacacca tgagagtcgg gaacacccga 1380

-continued agtccgtagc ctaaccgcaa ggggggcgc ggccgaaggt gggttcgata attggggtga 1440
agtcgtaaca aggtagccgt 1460

<210> SEQ ID NO 22
<211> LENGTH: 1485
<212> TYPE: DNA
<213> ORGANISM: Clostridium leptum
<220> FEATURE:
<221> NAME/KEY: rRNA
<222> LOCATION: (1)..(1485)
<223> OTHER INFORMATION: 16S rRNA coding gene sequence of Clostridium strain 2

<400> SEQUENCE: 22
agagtttgat cctggctcag gatgaacgct ggcggcgtgc ttaacacatg caagtcgaac 60
ggagcacccc tgaaggagtt ttcggacaac ggaagggact gcttagtggc ggacgggtga 120
gtaacgcgtg aggaacctgc cttggagtgg ggaataacag ctggaaacag ctgctaatac 180
cgcataatat atctgggccg catggctctg gatatcaaag atttatcgct ctgagatgga 240
ctcgcgtctg attagctagt tggcggggta acggcccacc aaggcgacga tcagtagccg 300
gactgagagg ttggccggcc acattgggac tgagacacgg cccagactcc tacgggaggc 360
agcagtgggg aatattgggc aatgggcgca agcctgaccc agcaacgccg cgtgaaggaa 420
gaaggctttc gggttgtaaa cttcttttgt cagggacgaa gcaagtgacg gtacctgacg 480
aataagccac ggctaactac gtgccagcag ccgcggtaat acgtaggtgg caagcgttat 540
ccggatttac tgggtgtaaa gggcgtgtag gcgggactgc aagtcagatg tgaaaaccac 600
gggctcaacc tgtgggcctg catttgaaac tgtagttctt gagtactgga gaggcagacg 660
gaattctagt tgtagcgtga aatgcgtaga tatagaagaa cacagttgcg gagccggtct 720
gcaactgacg ctgagcgcga aagcgtgggg agcaaacagg attagatacc ctggtagtcc 780
acgctgtaaa cgatggatta ctaggtgtgg ggggactgac cccctccgtg ccgcagttaa 840
cacaataagt atcccacctg gggagtacga tcgcaaggtt gaaactcaaa aggaattgac 900
gggggcccgc acaagcggtg gagtatgtgg tttaaattcg aagcaacgcg aagaacctta 960
ccagggcttg acatcccggt gaccgtccta gagataggat tttcccttcg gggacactgg 1020
agacaggtgg tgcatggttg tcgtcagctc gtgtcgtgag atgttgggtt aagtcccgca 1080
acgagcgcaa cccttattgt tagttgctac gcaagagcac tctagcgaga ctgccgttga 1140
caaaacggag gaaggtgggg acgacgtcaa atcatcatgc cccttatgtc ctgggccaca 1200
cacgtactac aatggtggtc aacagaggga agcaaagccg cgaggtggag caaatcccta 1260
aaagccatcc cagttcggat cgcaggctgc aacccgcctg cgtgaagttg gaatcgctag 1320
taatcgcgga tcagaatgcc gcggtgaata cgttcccggg ccttgtacac accgcccgtc 1380
acaccatgag agtcgggaac acccgaagtc cgtagcctaa ccgcaagggg ggcgcggccg 1440
aaggtgggtt cgataattgg ggtgaagtcg taacaaggta gccgt 1485

<210> SEQ ID NO 23
<211> LENGTH: 1491
<212> TYPE: DNA
<213> ORGANISM: Clostridium leptum
<220> FEATURE:
<221> NAME/KEY: rRNA
<222> LOCATION: (1)..(1491)
<223> OTHER INFORMATION: 16S rRNA coding gene sequence of Clostridium strain 3

<400> SEQUENCE: 23

```
agagtttgat cctggctcag gacgaacgct ggcggcgtgc ttaacacatg caagtcgaac     60
ggagcacctt cgaaagagac ttcggtcaat ggaaaagaat gcttagtggc ggacgggtga    120
gtaacgcgtg aggaacctgc ctttcagtgg gggacaacag ttggaaacga ctgctaatac    180
cgcataacgt acgggtatcg catggtatct gtaccaaaga tttatcgctg agagatggcc    240
tcgcgtctga ttagctagtt ggtagggtaa cggcctacca aggcgacgat cagtagccgg    300
actgagaggt tggccggcca cattgggact gagatacggc ccagactcct acgggaggca    360
gcagtgggga atattgggca atgggcgaaa gcctgaccca gcaacgccgc gtgaaggaag    420
aaggctttcg ggttgtaaac ttcttttgac ggggaagagc agaagacggt acctgtcgaa    480
taagccacgg ctaactacgt gccagcagcc gcggtaatac gtaggtggca agcgttgtcc    540
ggatttactg ggtgtaaagg gcgtgtagcc gggctgacaa gtcagatgtg aaatccgggg    600
gctcaacccc cgaactgcat ttgaaactgt tggtcttgag tatcggagag gcaggcggaa    660
ttcctagtgt agcggtgaaa tgcgtagata ttagggggaa caccagtggc gaagcggcct    720
gctggacgac aactgacggt gaggcgcgaa agcgtgggga gcaaacagga ttagataccc    780
tggtagtcca cgctgtaaac gatggatact aggtgtgcgg ggactgaccc ctgcgtgccg    840
cagctaacgc aataagtatc ccacctgggg agtacgatcg caaggttgaa actcaaagga    900
attgacgggg gcccgcacaa gcggtggatt atgtggttta attcgatgca acgcgaagaa    960
ccttaccagg gcttgacatc ctactaacga agtagagata cattaggtac ccttcggggg   1020
aagtagagac aggtggtgca tggttgtcgt cagctcgtgt cgtgagatgt tgggttaagt   1080
cccgcaacga gcgcaaccct tattgttagt tgctacgcaa gagcactcta gcgagactgc   1140
cgttgacaaa acggaggaag gtggggacga cgtcaaatca tcatgcccct tatgtcctgg   1200
gctacacacg taatacaatg gcggtcaaca gagggatgca aaaccgcgag gtggagcgaa   1260
cccctaaaag ccgtcccagt tcagatcgca gtctgcaacc cgactgcgtg aagtcggaat   1320
cgctagtaat cgcggatcag catgccgcgg tgaatacgtt cccgggcctt gtacacaccg   1380
cccgtcacac catgagagtc gggaacaccc gaagtccgta gcctaaccgc aaggagggcg   1440
cggccgaagg tgggttcgat aattggggtg aagtcgtaac aaggtagccg t            1491
```

<210> SEQ ID NO 24
<211> LENGTH: 1491
<212> TYPE: DNA
<213> ORGANISM: Clostridium coccoides
<220> FEATURE:
<221> NAME/KEY: rRNA
<222> LOCATION: (1)..(1491)
<223> OTHER INFORMATION: 16S rRNA coding gene sequence of Clostridium strain 4

<400> SEQUENCE: 24

```
agagtttgat cctggctcag gatgaacgct ggcggcgtgc ctaacacatg caagtcgaac     60
gggtgtacgg ggaggaaggc ttcggccgga aaacctgtgc atgagtggcg gacgggtgag    120
taacgcgtgg gcaacctggc ctgtacaggg ggataacact tagaaatagg tgctaatacc    180
gcataacggg ggaagccgca tggcttttcc ctgaaaactc cggtggtaca ggatgggccc    240
gcgtctgatt agccagttgg cagggtaacg gcctaccaaa gcgacgatca gtagccggcc    300
tgagagggcg gacggccaca ctgggactga gacacggccc agactcctac gggaggcagc    360
agtgggggat attgcacaat gggggaaac cctgatgcag cgacgccgcg tgagtgaaga    420
agtatttcgg tatgtaaagc tctatcagca gggaagaaaa tgacggtacc tgactaagaa    480
```

-continued gccccggcta actacgtgcc agcagccgcg gtaatacgta gggggcaagc gttatccgga 540
tttactgggt gtaaagggag cgtagacggc agcgcaagtc tgagtgaaat cccatggctt 600
aaccatggaa ctgctttgga aactgtgcag ctggagtgca ggagagtaag cggaattcct 660
agtgtagcgt gaaatgcgta gattatagga ggaacaccag tggcgaaggc ggctaactga 720
actgtaactg acgttgaggc tcgaaagcgt ggggagcaaa caggattaga taccctggta 780
gtccacgccg taaacgatga ttactaggtg ttggggggacc aaggtcttcg gtgccggcgc 840
aaacgcatta agtaatccac ctggggagta cgttcgcaag aatgaaactc aaaggaattg 900
acggggaccc gcacaagcgg tggagcatgt ggtttaattc gaagcaacgc gaagaacctt 960
acctggtctt gacatcccga tgacgagtga gcaaagtcac tttcccttcg ggcattgga 1020 gacaggtggt gcatggttgt cgtcagctcg tgtcgtgaga tgttgggtta agtcccgcaa 1080
cgagcgcaac ccctatttcc agtagccagc aggtagagct gggcactctg gagagactgc 1140
ccgggataac cgggaggaag gcggggatga cgtcaaatca tcatgcccct tatgatcagg 1200
gctacacacg tgctacaatg gcgtaaacaa agggaagcga gacggtgacg ttgagcaaat 1260
cccaaaaata acgtcccagt tcggattgta gtctgcaact cgactacatg aagctggaat 1320
cgctagtaat cgcgaatcag aatgtcgcgg tgaatacgtt cccgggtctt gtacacaccg 1380
cccgtcacac catgggagtc ggaaatgccc gaagtcagtg acctaaccga aaggaaggag 1440
ctgccgaagg tggagccggt aactggggtg aagtcgtaac aaggtagccg t 1491

<210> SEQ ID NO 25
<211> LENGTH: 1467
<212> TYPE: DNA
<213> ORGANISM: Clostridium leptum
<220> FEATURE:
<221> NAME/KEY: rRNA
<222> LOCATION: (1)..(1467)
<223> OTHER INFORMATION: 16S rRNA coding gene sequence of Clostridium
strain 5

<400> SEQUENCE: 25
agagtttgat cctggctcag gacgaacgct ggcggcacgc ctaacacatg caagtcgaac 60
ggagtgaaga tgctcgcatc tgaacttagt ggcggacggg tgagtaacac gtgagcaacc 120
tgcctttcag agggggatta cgtttggaaa cgaacgctaa taccgcataa aatatcggag 180
tcgcatggca ctgatatcaa aggagcaatc cgctgaaaga tgggctcgcg tccgattagg 240
cagttggcgg ggtatcggcc caccaaaccg acaatcggta gccggactga gaggttgaac 300
ggccacattg ggactgagac gcggcccaga ctcctacggg aggcagcagt gggggatatt 360
gcacaatggg ggaaaccctg atgcagcgat gccgcgtgaa tgaagacggc cttcgggttg 420
taaagttctg tcgcagggga cgaaaatgac ggtaccctgc aagaaagctc cggctaacta 480
cgtgccagca gccgcggtaa tacgtaggga gcaagcgttg tccggaatta ctgggtgtaa 540
agggagcgta ggcgggagga taagttgaat gtgaaatcta tgggctcaac ccatagctgc 600
gttcaaactg ttcttcttga gtgaagtaga ggcaggcgga attcctagtg tagcggtgaa 660
atgcgtagat attaggagga caccagtggc gaaggcgggc tgctgggctt tactgacgct 720
gaggctcgaa agcgtgggta gcaaacagga ttagataccc tggtagtcca cgcggtaaac 780
gatgattact aggtgtgggt ggactgaccc catccgtgcc ggagttaaca caataagtaa 840
tccacctggg gagtacggcc gcaaggttga aactcaaagg aattgacggg ggcccgcaca 900
agcagtggag tatgtggttt aattcgacgc aacgcgaaga accttaccag gtcttgacat 960

```
cgagtgacgg acatagagat atgtctttcc ttcgggacac gaagacaggt ggtgcatggt   1020

tgtcgtcagc tcgtgtcgtg agatgttggg ttaagtcccg caacgagcgc aacccttacc   1080

attagttgct acgcaagagc actctaatgg gactgccgtt gacaaaacgg aggaaggtgg   1140

ggatgacgtc aaatcatcat gccccttatg acctgggcga cacacgtact acaatggcgg   1200

tcaacagagg gaggcaaagc cgcgaggcag agcaaacccc taaaagccgt ctcagttcgg   1260

attgcaggct gcaactcgcc tgcatgaagt cggaattgct agtaatcgcg gatcagcatg   1320

ccgcggtgaa tacgttcccg ggccttgtac acaccgcccg tcacaccatg agagccggta   1380

acacccgaag tcaatagtct aaccgcaagg aggacattgc cgaaggtggg attggtaatt   1440

ggggtgaagt cgtaacaagg tagccgt                                       1467
```

<210> SEQ ID NO 26
<211> LENGTH: 1474
<212> TYPE: DNA
<213> ORGANISM: Clostridium coccoides
<220> FEATURE:
<221> NAME/KEY: rRNA
<222> LOCATION: (1)..(1474)
<223> OTHER INFORMATION: 16S rRNA coding gene sequence of Clostridium
      strain 6

<400> SEQUENCE: 26

```
agagtttgat catggctcag gatgaacgct ggcggcgtgc ctaacacatg caagtcgaac     60

gggtgtacgg gaaggaaggc ttcggccgga aaacctgtgc atgagtggcg gacgggtgag    120

taacgcgtgg gcaacctggc ctgtacaggg ggataacact tagaaatagg tgctaatacc    180

gcataacggg ggaagccgca tggcttttcc ctgaaaactc cggtggtaca ggatgggccc    240

gcgtctgatt agccagttgg cagggtaacg gcctaccaaa gcgacgatca gtagccggcc    300

tgagagggcg gacggccaca ctgggactga gacacggccc agactcctac gggaggcagc    360

agtgggggat attgcacaat gggggaaacc ctgatgcagc gacgccgcgt gggtgaagaa    420

gcgcctcggc gcgtaaagcc ctgtcagcag ggaagaaaat gacggtacct gaagaagaag    480

ccccggctaa ctacgtgcca gcagccgcgg taatacgtag ggggcaagc gttatccgga    540

tttactgggt gtaaaggggg cgcagacggc gatgcaagcc aggagtgaaa gcccggggcc    600

caaccccggg actgctcttg ggaactgcgt ggctggagtg cagagggcag cggaattcct    660

ggtgaaatgc gtagatatca gaagacacgg tgcgaggcgg cctgctgact gcactgacgt    720

tgagccgaag cgtggggagc aaacaggatt agataccgtg gtagtcacgc cgtaaacgat    780

gattactagg tgtcggggag cagagactgc ccggtgccgc agccaacgca ttaagtaatc    840

cacctgggga gtacgttcgc aagaatgaaa ctcaaaggaa ttgacgggga cccgcacaag    900

cggtggagca tgtggtttaa ttcgaagcaa cgcgaagaac cttacctggt cttgacatcc    960

cgatgacgag tgagcaaagt cactttccct tcggggcatt ggagacaggt ggtgcatggt   1020

tgtcgtcagc tcgtgtcgtg agatgttggg ttaagtcccg caacgagcgc aacccctatt   1080

tccagtagcc agcaggtaga gctgggcact ctggagagac tgcccgggat aaccgggagg   1140

aaggcgggga tgacgtcaaa tcatcatgcc ccttatgatc agggctacac acgtgctaca   1200

atggcgtaaa caaagggaag cgagacggtg acgttaagca aatcccaaaa ataacgtccc   1260

agttcggatt gtagtctgca actcgactac atgaagctgg aatcgctagt aatcgcgaat   1320

cagaatgtcg cggtgaatac gttcccgggt cttgtacaca ccgcccgtca caccatggga   1380

gtcggaaatg cccgaagtca gtgacctaac cgaaaggaag gagctgccga aggtggagcc   1440
```

ggtaactggg gtgaagtcgt aacaaggtag ccgt 1474

<210> SEQ ID NO 27
<211> LENGTH: 1484
<212> TYPE: DNA
<213> ORGANISM: Clostridium leptum
<220> FEATURE:
<221> NAME/KEY: rRNA
<222> LOCATION: (1)..(1484)
<223> OTHER INFORMATION: 16S rRNA coding gene sequence of Clostridium
strain 7

<400> SEQUENCE: 27
agagtttgat cctggctcag gatgaacgct ggcggcgtgc ttaacacatg caagtcgaac 60
gagaatccag tgaaggagtt ttcggacaac ggatctggag gaaagtggcg gacgggtgag 120
taacgcgtga gcaatctgcc ttggagtggg gaataacggt tggaaacagc cgctaatacc 180
gcatgatgcg tctgggaggc atctctctgg acgccaaaga tttatcgctc tgagatgagc 240
tcgcgtctga ttagcttgtt ggcggggtaa aggcccacca aggcgacgat cagtagccgg 300
actgagaggt tggccggcca cattgggact gagacacggc ccagactcct acgggaggca 360
gcagtgggga atattgggca atgggcgcaa gcctgaccca gcaacgccgc gtgaaggaag 420
aaggctttcg ggttgtaaac ttcttttctg agggacgaag aaagtgacgg tacctcagga 480
ataagccacg gctaactacg tgccagcagc cgcggtaata cgtaggtggc aagcgttatc 540
cggatttatt gggtgtaaag ggcgtgtagg cgggaaagca agtcagatgt gaaaactcag 600
ggctcaaccc tgagcctgca tttgaaactg tttttcttga gtgctggaga ggcaatcgga 660
attccgtgtg tagcggtgaa atgcgtagat atacggagga caccagtggc gagcggattg 720
ctggacagta ctgacgctga agcgcgaaag cgtgggagca aacagataga tacctggtag 780
tcacgcgtaa acgatggata ctaggtgtgg ggggactgac cccctccgtg ccgcagctaa 840
cgcaataagt atcccacctg gggagtacga tcgcaaggtt gaaactcaaa ggaattgacg 900
ggggcccgca caagcggtgg agtatgtggt ttaattcgaa gcaacgcgaa gaaccttacc 960
agggcttgac atcctgctaa cgaaccagag atggattagg tgcccttcgg ggaaagcaga 1020
gacaggtggt gcatggttgt cgtcagctcg tgtcgtgaga tgttgggtta agtcccgcaa 1080
cgagcgcaac ccttattgtt agttgctacg caagagcact ctagcgagac tgccgttgac 1140
aaaacggagg aaggtgggga cgacgtcaaa tcatcatgcc ccttacgtcc tgggccacac 1200
acgtactaca atggcggcca acaaagagag gcaagaccgc gaggtggagc aaatctcaaa 1260
aagccgtccc agttcggatc gcaggctgca acccgcctgc gtgaagttgg aatcgctagt 1320
aatcgcggat cagcatgccg cggtgaatac gttcccgggc cttgtacaca ccgcccgtca 1380
caccatgaga gtcgggaaca cccgaagtcc gtagcctaac cgcaaggggg gcgcggccga 1440
aggtgggttc gataattggg gtgaagtcgt aacaaggtag ccgt 1484

<210> SEQ ID NO 28
<211> LENGTH: 1483
<212> TYPE: DNA
<213> ORGANISM: Clostridium leptum
<220> FEATURE:
<221> NAME/KEY: rRNA
<222> LOCATION: (1)..(1483)
<223> OTHER INFORMATION: 16S rRNA coding gene sequence of Clostridium
strain 8

<400> SEQUENCE: 28

```
agagtttgat cctggctcag gacgaacgct ggcggcgtgc ttaacacatg caagtcgaac     60
ggagcacccc tgaaggagtt ttcggacaac ggatgggaat gcttagtggc ggactggtga    120
gtaacgcgtg aggaacctgc cttccagagg gggacaacag ttggaaacga ctgctaatac    180
cgcatgatgc gttggagccg catgactccg acgtcaaaga tttatcgctg gaagatggcc    240
tcgcgtctga ttagctagtt ggtgaggtaa cggcccacca aggcgacgat cagtagccgg    300
actgagaggt tggccggcca cattgggact gagatacggc ccagactcct acgggaggca    360
gcagtgggga atattgggca atggacgcaa gtctgaccca gcaacgccgc gtgaaggaag    420
aaggctttcg ggttgtaaac ttcttttaag gggaagagc agaagacggt accccttgaa     480
taagccacgg ctaactacgt gccagcagcc gcggtaatac gtaggtggca agcgttgtcc    540
ggatttactg ggtgtaaagg gcgtgcagcc ggagagacaa gtcagatgtg aaatccacgg    600
gctcaacccg tgaactgcat ttgaaactgt ttcctttgag tgtcggagag gtaatcggga    660
ttccttgtgt agcggtgaat gcgtagatat agagaccaca gtgccgacgc cgaatactga    720
cgatactgac ggtgagcgcg aaagcgtggg gagcaaacag gattagatac cctggtagtc    780
cacgctgtaa acgatcgata ctaggtgtgc ggggactgac ccctgcgtgc cggagttaac    840
acaataagta tcgcacctgg ggagtacgat cgcaaggttg aaactcaaag gaattgacgg    900
gggcccgcac aagcggtgga ttatgtggtt taattcgaag caacgcgaag aaccttacca    960
gggcttgaca tcctgctaac gaagtagaga tacattaggt gcccttcggg gaaagcagag   1020
acaggtggtg catggttgtc gtcagctcgt gtcgtgagat gttgggttaa gtcccgcaac   1080
gagcgcaacc cctattgtta gttgctacgc aagagcactc tagcgagact gccgttgaca   1140
aaacggagga aggcggggac gacgtcaaat catcatgccc cttatgtcct gggctacaca   1200
cgtaatacaa tggcggttaa caaagggatg caaagccgcg aggcagagcg aaccccaaaa   1260
agccgtccca gttcggatcg caggctgcaa cccgcctgcg tgaagtcgga atcgctagta   1320
atcgcggatc agcatgccgc ggtgaatacg ttcccgggcc ttgtacacac cgcccgtcac   1380
accatgagag tcgggaacac ccgaagtccg tagcctaacc gcaaggaggg cgcggccgaa   1440
ggtgggttcg ataattgggg tgaagtcgta acaaggtagc cgt                     1483
```

<210> SEQ ID NO 29
<211> LENGTH: 1480
<212> TYPE: DNA
<213> ORGANISM: Clostridium coccoides
<220> FEATURE:
<221> NAME/KEY: rRNA
<222> LOCATION: (1)..(1480)
<223> OTHER INFORMATION: 16S rRNA coding gene sequence of Clostridium strain 9

<400> SEQUENCE: 29

```
ggagtttgat cctggctcag gatgaacgct ggcggcgtgc ttaacacatg caagtcgaac     60
gggctcatat tgaaacctag tgatgtatga gttagtggcg gacgggtgag taacgcgtgg    120
agaacctgcc gtatactggg ggataacact tagaaatagg tgctaatacc gcataagcgc    180
acagcttcgc atgaagcagt gtgaaaaact ccggtggtat acgatggatc cgcgtctgat    240
tagctggttg gcggggtaac agcccaccaa ggcgacgatc agtagccggc ctgagagggt    300
gaacggccac attgggactg agacacggcc caaactccta cgggaggcag cagtggggaa    360
tattgcacaa tgggggaaac cctgatgcag cgacgccgcg tgagtgaaga agtatttcgg    420
tatgtaaagc tctatcagca gggaagaaat actgacctta cggtcagcag acggtacctg    480
```

-continued

```
actaagaagc cccgggctaa ctacgtgcca gcagccgcgg taatacgtag gggcaagcgt    540

tatccggatt tactgggtgt aaagggggcg cagacggcga tgcaagccag gagtgaaagc    600

cggggcccaa ccccgggact gctcttggac tgcgtggctg gagtgcagag ggcagcgaat    660

tcctgtgtag cgtgaatgcg tagattcaga ggacacgtgc gagcgcctgc tgactgcact    720

gacgtgagcc cgaagcgtgg ggagcaaaca ggattagata cctggtagtc cacgccgtaa    780

acgatgatta ctaggtgtcg gggagcagag actgcccggt gccgcagcca acgcattaag    840

taatccacct ggggagtacg ttcgcaagaa tgaaactcaa aggaattgac ggggacccgc    900

acaagcggtg gagcatgtgg tttaattcga agcaacgcga agaaccttac caggccttga    960

catcccctg gatggcccgt aacggggtca gcctttcggg gcaggggaga caggtggtgc   1020

atggttgtcg tcagctcgtg tcgtgagatg ttgggttaag tcccgcaacg agcgcaaccc   1080

ctgcccgcag tagccagcat tttagatggg gactctgcgg ggactgccgg ggacaacccg   1140

gaggaaggcg gggatgacgt caaatcatca tgccccttat ggcctgggct acacacgtgc   1200

tacaatggcg ccgacagagg gaggcgaagc ggcgacgcgg agcgaacccc aaaaacggcg   1260

tcccagttcg gattgtagtc tgcaacccga ctacatgaag ccggaatcgc tagtaatcgc   1320

ggatcagaat gccgcggtga atacgttccc gggtcttgta cacaccgccc gtcacaccat   1380

gggagccggg aatgcccgaa gtctgtgacc gaacccgtaa ggggaggggc agccgaaggc   1440

aggcccggtg actggggtga agtcgtaaca aggtagccgt                          1480


<210> SEQ ID NO 30
<211> LENGTH: 1489
<212> TYPE: DNA
<213> ORGANISM: Clostridium leptum
<220> FEATURE:
<221> NAME/KEY: rRNA
<222> LOCATION: (1)..(1489)
<223> OTHER INFORMATION: 16S rRNA coding gene sequence of Clostridium
      strain 10

<400> SEQUENCE: 30

agagtttgat cctggctcag gatgaacgct ggcggcgtgc ttaacacatg caagtcgagc     60

gaagcacttt tttagaactc ttcggaggga agagagggtg acttagcggc ggacgggtga    120

gtaacgcgtg ggcaacctgc cttacacagg gggataacaa ttagaaatga ttgctaatac    180

cgcataagac cacggtactg catggtacag tggtaaaaac tgaggtggtg taagatgggc    240

ccgcgtctga ttaggtagtt ggtggggtag aagcctacca agccgacgat cagtagccga    300

cctgagaggg cgaccggcca cattgggact gagacacggc ccaaactcct acgggaggca    360

gcagtgggga atattgcaca atgggggaaa ccctgatgca gcgacgccgc gtgagtgagg    420

aagtatttcg gtatgtaaag ctctatcagc agggaagaaa atgacggtac ctgactaaga    480

agccccggc taactacgtg ccagcagccg cggtaatacg taggggcaa gcgttatccg      540

gatttactgg gtgtaaaggg agcgtagacg gacttgcaag tctgatgtga aatccggggg    600

cccaacccgg gactgcattg aaactgtatt ttttggaggg gtccgaggag gcaagtggaa    660

tcctgggtag cggtgaaatg gcgtagaatt cagggaggaa caccagtggc ggaaggcgaa    720

ttactggacg ataactgacg gtgaggcgcg aagcgtggga gcaaacaaga attagatacc    780

ctggtagtca cgctgtaacg atcgatacta ggtgtgcggg gactgacccc tgcgtgccgg    840

agttaacaca ataagtatcg cactggggag tacgatcgca aggttgaaac tcaaaggaat    900

tgacgggggc ccgcacaagc ggtggattat gtggtttaat tcgaagcaac gcgaagaacc    960
```

```
ttaccagggc ttgacatcct gctaacgaag tagagataca ttaggtgccc ttcggggaaa   1020

gcagagacag gtggtgcatg gttgtcgtca gctcgtgtcg tgagatgttg ggttaagtcc   1080

cgcaacgagc gcaaccccta ttgttagttg ctacgcaaga gcactctagc gagactgccg   1140

ttgacaaaac ggaggaaggc ggggacgacg tcaaatcatc atgcccctta tgtcctgggc   1200

tacacacgta atacaatggc ggttaacaaa gggatgcaaa gccgcgaggc agagcgaacc   1260

ccaaaaagcc gtcccagttc ggatcgcagg ctgcaacccg cctgcgtgaa gtcggaatcg   1320

ctagtaatcg cggatcagca tgccgcggtg aatacgttcc cgggccttgt acacaccgcc   1380

cgtcacacca tgagagtcgg gaacacccga agtccgtagc ctaaccgcaa ggagggcgcg   1440

gccgaaggtg ggttcgataa ttggggtgaa gtcgtaacaa ggtagccgt               1489


<210> SEQ ID NO 31
<211> LENGTH: 1490
<212> TYPE: DNA
<213> ORGANISM: Clostridium leptum
<220> FEATURE:
<221> NAME/KEY: rRNA
<222> LOCATION: (1)..(1490)
<223> OTHER INFORMATION: 16S rRNA coding gene sequence of Clostridium
      strain 11

<400> SEQUENCE: 31

agagtttgat cctggctcag gatgaacgct ggcggcgtgc ttaacacatg caagtcgaac     60

gagaatccag tgaaggagtt ttcggacaac ggatctggag gaaagtggcg gacgggtgag    120

taacgcgtga gcaatctgcc ttggagtggg gaataacggt tggaaacagc cgctaatacc    180

gcatgatgcg tctgggaggc atctctctgg acgccaaaga tttatcgctc tgagatgagc    240

tcgcgtctga ttagcttgtt ggcggggtaa aggcccacca aggcgacgat cagtagccgg    300

actgagaggt tggccggcca cattgggact gagacacggc ccagactcct acgggaggca    360

gcagtgggga atattgggca atgggcgcaa gcctgaccca gcaacgccgc gtgaaggaag    420

aaggctttcg ggttgtaaac ttcttttctg agggacgaag aaagtgacgg tacctcagga    480

ataagccacg gctaactacg tgccagcagc cgcggtaata cgtaggtggc aagcgttatc    540

cggatttatt gggtgtaaag ggcgtgtagg cgggaaagca agtcagatgt gaaaactcag    600

ggctcaaccc tgagcctgca tttgaaactg tttttcttga gtgctggaga ggcaatcgga    660

attccgtgtt gtagcggtga aatgcgtaga ttataccgga ggaaccacca gtggcggaag    720

gcggattgct ggaacagtaa ctgacgctga ggcgccgaaa gcgtggggag caaacaggat    780

agataccctg gtagtccacg ccgtaaacga tggatactaa gtgtggggga ctgacccctt    840

cgtgcccagc taagcaataa gtttcccacc tggggagtac gatcgcaggt gaaactcaaa    900

ggaattgacg gggcccgcc caagcgggtg gagtaggggt taattggagc aacgggaaga    960

accttaccag ggcttgacat cctgtaacga accagaagag ggattaggtg ccttcgggga   1020

aagcagagac aggtggtgca tggttgtcgt cagctcgtgt cgtgagatgt gggtaaagtc   1080

ccgcaacgag cgcaaccctt attgttagtt gctacgcaag agcactctag cgagactgcc   1140

gttgacaaaa cggaggaagg tggggacgac gtcaaatcat catgcccctt acgtcctggg   1200

ccacacacgt actacaatgg cggccaacaa agagaggcaa gaccgcgagg tggagaaaat   1260

ctcaaaaagc cgtcccagtt cggatcgcag gctgcaaccc gcctgcgtga agttggaatc   1320

gctagtaatc gcggatcagc atgccgcggt gaatacgttc ccgggccttg tacacaccgc   1380

ccgtcacacc atgagagtcg ggaacacccg aagtccgtag cctaaccgca agggggcgc    1440
```

-continued ggccgaaggt gggttcgata attggggtga agtcgtaaca aggtagccgt 1490

<210> SEQ ID NO 32
<211> LENGTH: 1489
<212> TYPE: DNA
<213> ORGANISM: Clostridium coccoides
<220> FEATURE:
<221> NAME/KEY: rRNA
<222> LOCATION: (1)..(1489)
<223> OTHER INFORMATION: 16S rRNA coding gene sequence of Clostridium strain 12

<400> SEQUENCE: 32
agagtttgat catggctcag gatgaacgct ggcggcgtgc ttaacacatg caagtcgaac 60
gggctcatat tgaaacctag tgatgtatga gttagtggcg gacgggtgag taacgcgtgg 120
agaacctgcc gtatactggg ggataacact tagaaatagg tgctaatacc gcataagcgc 180
acagcttcgc atgaagcagt gtgaaaaact ccggtggtat acgatggatc cgcgtctgat 240
tagctggttg gcggggtaac agcccaccaa ggcgacgatc agtagccggc ctgagagggt 300
gaacggccac attgggactg agacacggcc caaactccta cgggaggcag cagtggggaa 360
tattgcacaa tgggggaaac cctgatgcag cgacgccgcg tgagtgaaga agtatttcgg 420
tatgtaaagc tctatcagca gggaagaaat actgacctta cggtcagcag acggtacctg 480
actaagaagc cccggctaac tacgtgccag cagccgcggt aatacgtagg gggcaagcgt 540
tatccggatt tactgggtgt aaagggagcg tagacggcag cgcaagtctg aagtgaaatc 600
ccatggctta accatggaac tgctttggaa actgtgcagc tggagtgcag gagaggtaag 660
cggaattcct agtgtagcgg tgaatgcgta gatattagag gacaccagtg gcgatgcggc 720
ttactggact gtactgacgt tgagctcgaa agcgtgggga gcaccagaat tagaatactg 780
tagtcacgcc gtaaccgatg atactaggtg tgggggacca aggtctcgtg ccggcggcaa 840
acgcattaag taatccacct ggggagtacg ttcgcaagaa tgaaactcaa aggaattgac 900
ggggacccgc acaagcggtg gagcatgtgg tttaattcga agcaacgcga agaaccttac 960
ctggtcttga catcccgatg acgagtgagc aaagtcactt tcccttcggg gcattggaga 1020
caggtggtgc atggttgtcg tcagctcgtg tcgtgagatg ttgggttaag tcccgcaacg 1080
agcgcaaccc ctatttccag tagccagcag gtagagctgg gcactctgga gagactgccc 1140
gggataaccg ggaggaaggc ggggatgacg tcaaatcatc atgcccctta tgatcagggc 1200
tacacacgtg ctacaatggc gtaaacaaag ggaagcgaga cggtgacgtt aagcaaatcc 1260
caaaaataac gtcccagttc ggattgtagt ctgcaactcg actacatgaa gctggaatcg 1320
ctagtaatcg cgaatcagaa tgtcgcggtg aatacgttcc cgggtcttgt acacaccgcc 1380
cgtcacacca tgggagtcgg aaatgcccga agtcagtgac ctaaccgaaa ggaaggagct 1440
gccgaaggtg gagccggtaa ctggggtgaa gtcgtaacaa ggtagccgt 1489

<210> SEQ ID NO 33
<211> LENGTH: 1456
<212> TYPE: DNA
<213> ORGANISM: Clostridium coccoides
<220> FEATURE:
<221> NAME/KEY: rRNA
<222> LOCATION: (1)..(1456)
<223> OTHER INFORMATION: 16S rRNA coding gene sequence of Clostridium strain 13

<400> SEQUENCE: 33
agagtttgat catggctcag gatgaacgct ggcggcgtgc ttaacacatg caagtcgaac 60
gaagcacttg agaacgattc ttcggatgag gacttttgtg actgagtggc ggacgggtga 120
gtaacgcgtg ggtaacctgc cctatacagg gggataacag ttagaaatga ctgctaatac 180
cgcataagcg cactaaaacc gcatggttcg gtgtgaaaaa ctgaggtggt ataggatgga 240
cccgcgtctg attagcttgt tggtggggta acggctcacc aaggcgacga tcagtagccg 300
gcctgagagg gcgaccggcc acattgggac tgagacacgg cccaaactcc tacgggaggc 360
agcagtgggg gatattgcac aatgggggga accctgatgc agcgacgccg cgtgggtgaa 420
gaagcgcctc ggcgcgtaaa gccctgtcag cagggaagaa aatgacggta cctgaagaag 480
aagccccggc taactacgtg ccagcagccg cggtaatacg taggggcaag cgttattccg 540
ggatttactg ggtgtaaagg gggcgcagac ggcgatgcaa gccaggagtg aagcccgggg 600
cccacccggg actgctcttg gactgcgtgc tggagtgcag aaggggcagc gatcctgtgt 660
accgtgaatt gcgtagatat cagagacacg ttgcgagcgc tgctgactgc actgacgtga 720
gcgaagctgg agcacagata gatactgtag tcagcgtaac gatgatacta gtgtcgggag 780
cagagactgc ccgttgcggc agcccaacgc attagtattc cacttgggga gtacgtttcg 840
cagaatgaac ttcaaggaaa tgacggggac ccgcacaagg cggtggagca tgtggtttaa 900
ttcgaagcaa cgcgaagaac cttaccaggc cttgacatcc cccctggatg gcccgtaacg 960
gggtcagcct ttcggggcag gggagacagg tggtgcatgg ttgtcgtcag ctcgtgtcgt 1020
gagatgttgg gttaagtccc gcaacgagcg caacccctgc ccgcagtagc cagcatttta 1080
gatggggact ctgcggggac tgccggggac aacccggagg aaggcgggga tgacgtcaaa 1140
tcatcatgcc ccttatggcc tgggctacac acgtgctaca atggcgccga cagagggagg 1200
cgaagcggcg acgcggagcg aaccccaaaa acggcgtccc agttcggatt gtagtctgca 1260
acccgactac atgaagccgg aatcgctagt aatcgcggat cagaatgccg cggtgaatac 1320
gttcccgggt cttgtacaca ccgcccgtca caccatggga gccgggaatg cccgaagtct 1380
gtgaccgaac ccgtaagggg aggggcagcc gaaggcaggc tcggtgactg ggtgaagtc 1440 gtaacaaggt agccgt 1456

<210> SEQ ID NO 34
<211> LENGTH: 1475
<212> TYPE: DNA
<213> ORGANISM: Clostridium leptum
<220> FEATURE:
<221> NAME/KEY: rRNA
<222> LOCATION: (1)..(1475)
<223> OTHER INFORMATION: 16S rRNA coding gene sequence of Clostridium
strain 14

<400> SEQUENCE: 34
agagtttgat cctggctcag gacgaacgct ggcggcgtgc ttaacacatg caagtcgaac 60
ggagcacccc tgaaggagtt ttcggacaac ggatgggaat gcttagtggc ggactggtga 120
gtaacgcgtg aggaacctgc cttccagagg gggacaacag ttggaaacga ctgctaatac 180
cgcatgatgc gttggagccg catgactccg acgtcaaaga tttatcgctg gaagatggcc 240
tcgcgtctga ttagctagtt ggtgaggtaa cggcccacca aggcgacgat cagtagccgg 300
actgagaggt tggccggcca cattgggact gagatacggc ccagactcct acgggaggca 360
gcagtgggga atattgggca atggacgcaa gtctgaccca gcaacgccgc gtgaaggaag 420
aaggctttcg ggttgtaaac ttcttttaag gggaagagc agaagacggt accccttgaa 480
taagccacgg ctaactacgt gccagcagcc gcggtaatac gtaggtggca agcgttgtcc 540

-continued

```
ggatttactg ggtgtaaagg gcgtgcagcc ggagagacaa gtcagatgtg aaatccacgg    600

gctcaacccg tgaactgcat ttgaaactgt ttcccttgag tgtcggagag gtaatcggaa    660

tttccttgtg tagcggtgaa tgcgtagata taaggaagga cacagtggcg agcggattac    720

tggacgatac tgacgtgagc gcgaaagcgt gggggagcaa cagaaattag atactgtagt    780

gcagctgtaa cgatcgatac tagttgcggg actgacccct tgcgtgcgag ttacacaata    840

agtatcgcac ctgggagtac gatcgcaagg ttggaactca aaggaattga cggggcccgc    900

acaagcgttg gattatgtgg tttaattcga agcaacgcga agaaccttac cagggcttga    960

catcctgcta acgaagtaga gatacattag gtgcccttcg ggaaagtag agacaggtgg    1020

tgcatggttg tcgtcagctc gtgtcgtgag atgttgggtt aagtcccgca acgagcgcaa   1080

cccctattgt tagttgctac gcaagagcac tctagcgaga ctgccgttga caaaacggag   1140

gaaggcgggg acgacgtcaa atcatcatgc cccttatgtc ctgggctaca cacgtaatac   1200

aatggcggtt aacaaaggga tgcaaagccg cgaggcagag cgaaccccaa aaagccgtcc   1260

cagttcggat cgcaggctgc aacccgcctg cgtgaagtcg gaatcgctag taatcgcgga   1320

tcagcatgcc gcggtgaata cgttcccggg ccttgtacac accgcccgtc acaccatgag   1380

agtcgggaac acccgaagtc cgtagcctaa ccgcaaggag ggcgcggccg aaggtgggtt   1440

cgataattgg ggtgaagtcg taacaaggta gccgt                              1475
```

<210> SEQ ID NO 35
<211> LENGTH: 1480
<212> TYPE: DNA
<213> ORGANISM: Clostridium coccoides
<220> FEATURE:
<221> NAME/KEY: rRNA
<222> LOCATION: (1)..(1480)
<223> OTHER INFORMATION: 16S rRNA coding gene sequence of Clostridium strain 15

<400> SEQUENCE: 35

```
agagtttgat cctggctcag gatgaacgct ggcggcgtgc ttaacacatg caagtcgaac      60

gggctcatat tgaaacctag tgatgtatga gttagtggcg gacgggtgag taacgcgtgg    120

agaacctgcc gtatactggg ggataacact tagaaatagg tgctaatacc gcataagcgc    180

acagcttcgc atgaagcagt gtgaaaaact ccggtggtat acgatggatc cgcgtctgat    240

tagctggttg gcggggtaac agcccaccaa ggcgacgatc agtagccggc ctgagagggt    300

gaacggccac attgggactg agacacggcc caaactccta cgggaggcag cagtggggaa    360

tattgcacaa tgggggaaac cctgatgcag cgacgccgcg tgagtgaaga agtatttcgg    420

tatgtaaagc tctatcagca gggaagaaat actgacctta cggtcagcag acggtacctg    480

actaagaagc cccggctaac tacgtgccag cagccgcggt aatacgtagg ggcaagcgtt    540

atccggattt actgggtgta aagggagcgt agacggcagc gcaagtctga agtgaaatcc    600

catggcttaa cccatggaac tgctttggaa actgtgcagc tggagtgcag gagaggtaag    660

cggaattcct agtgtagcgt gaaatgcgta gattattagg aggacaacag tgcgagcgct    720

actgacgtga ggctcgaagc gtgggagcaa acaggattag atacctggta gtcacgcgta    780

aacgatgatt actagggtgt tgggggacca aggtcttcgg tgccggcgca aacgcattaa    840

gtaatccacc tggggagtac gttcgcaaga atgaaactca aaggaattga cggggacccg    900

cacaagcggt ggagcatgtg gtttaattcg aagcaacgcg aagaacctta cctggtcttg    960

acatcccgat gacgagtgag caaagtcact ttcccttcgg ggcattggag acaggtggtg   1020
```

-continued

```
catggttgtc gtcagctcgt gtcgtgagat gttgggttaa gtcccgcaac gagcgcaacc   1080

cctatttcca gtagccagca ggtagagctg ggcactctgg agagactgcc cgggataacc   1140

gggaggaagg cggggatgac gtcaaatcat catgcccctt atgatcaggg ctacacacgt   1200

gctacaatgg cgtaaacaaa gggaagcgag acggtgacgt taagcaaatc ccaaaaataa   1260

cgtcccagtt cggattgtag tctgcaactc gactacatga agctggaatc gctagtaatc   1320

gcgaatcaga atgtcgcggt gaatacgttc ccgggtcttg tacacaccgc ccgtcacacc   1380

atgggagtcg gaaatgcccg aagtcagtga cctaaccgaa aggaaggagc tgccgaaggt   1440

ggagccggta actggggtga agtcgtaaca aggtagccgt                         1480


<210> SEQ ID NO 36
<211> LENGTH: 1486
<212> TYPE: DNA
<213> ORGANISM: Clostridium papyrosolvens
<220> FEATURE:
<221> NAME/KEY: rRNA
<222> LOCATION: (1)..(1486)
<223> OTHER INFORMATION: 16S rRNA coding gene sequence of Clostridium
      strain 16

<400> SEQUENCE: 36

agagtttgat cctggctcag gataaacgct ggcggcgcac ataagacatg caagtcgaac     60

ggacttaact cattctttta gattgagagc ggttagtggc ggactggtga gtaacacgta    120

agcaacctgc ctatcagagg ggaataacag tgagaaatca ttgctaatac cgcatatgct    180

cacagtatca catgatacag tgaggaaagg agcaatccgc tgatagatgg gcttgcgcct    240

gattagttag ttggtggggt aacggcctac caagacgacg atcagtagcc ggactgagag    300

gttgaacggc cacattggga ctgagatacg gcccagactc ctacgggagg cagcagtcgg    360

gaatattgcg caatggagga aactctgacg cagtgacgcc gcgtatagga agaaggtttt    420

cggattgtaa actattgtcg ttagggaaga taaaagactg tacctaagga ggaagccccg    480

gctaactatg tgccagcagc cgcggtaata catagggggc aagcgttatc cggaattatt    540

gggtgtaaag ggtgcgtaga cggaagaaca agttggttgt gaaatccctc ggctcaactg    600

aggaactgca accaaaacta ttctccttga gtgtcggaga ggaaagtgga attcctagtg    660

tagcggtgaa atgcgtagat attaggagga acaccagtgg cgaaggcgac tttctggacg    720

ataactgacg ttgaggcacg aaagtgtggg gagcaaacag gattagatac cctggtagtc    780

cacactgtaa acgatggata ctaggtgtag ggtgtattaa gcactctgtg ccgccgctaa    840

cgcattaagt atcccacctg gggagtacga ccgcaaggtt gaaactcaaa ggaattgacg    900

ggggcccgca caagcagtgg agtatgtggt ttaattcgaa gcaacgcgaa gaaccttacc    960

agggcttgac atataccgga atatactaga gatagtatag tccttcggga ctggtataca   1020

ggtggtgcat ggttgtcgtc agctcgtgtc gtgagatgtt gggttaagtc ccgcaacgag   1080

cgcaacccct atcgttagtt gctagcaggt aatgctgaga actctagcga gactgccggt   1140

gataaatcgg aggaaggtgg ggatgacgtc aaatcatcat gccctttatg tcctgggcta   1200

cacacgtact acaatggccg taacagaggg aagcaatata gtgatatgga gcaaaaccct   1260

aaaagcggtc tcagttcgga ttgaaggctg aaattcgcct tcatgaagcc ggaattgcta   1320

gtaatggcag gtcagcatac tgccgtgaat acgttcccgg gccttgtaca caccgcccgt   1380

cacaccatga gagttggaaa tacccgaagc ctgtgagcta actgtaaaga ggcagcagtc   1440

gaaggtagag ccaatgattg ggtgaagtc gtaacaaggt agccgt                   1486
```

<210> SEQ ID NO 37
<211> LENGTH: 1493
<212> TYPE: DNA
<213> ORGANISM: Clostridium leptum
<220> FEATURE:
<221> NAME/KEY: rRNA
<222> LOCATION: (1)..(1493)
<223> OTHER INFORMATION: 16S rRNA coding gene sequence of Clostridium
strain 17

<400> SEQUENCE: 37

```
agagtttgat catggctcag gatgaacgct ggcggcgtgc ttaacacatg caagtcgaac     60

gagaaccaac ggattgagga ttcgtccaaa tgaagttggg gaaagtggcg gacgggtgag    120

taacgcgtga gcaatctgcc ttggagtggg gaataacggt tggaaacagc cgctaatacc    180

gcatgatgcg tctgggaggc atctctctgg acgccaaaga tttatcgctc tgagatgagc    240

tcgcgtctga ttagctagtt ggcggggcaa cggcccacca aggcgacgat cagtagccgg    300

actgagaggt tggccggcca cattgggact gagacacggc ccagactcct acgggaggca    360

gcagtgggga atattgggca atgggcgcaa gcctgaccca gcaacgccgc gtgaaggaag    420

aaggctttcg ggttgtaaac ttcttttaag ggggacgaac aaatgacggt acccccttgaa   480

taagccacgg ctaactacgt gccagcagcc gcggtaatac gtaggtggca agcgttatcc    540

ggatttattg ggtgtaaagg gcgtgtaggc gggaatgcaa gtcagatgtg aaaactatgg    600

gctcaaccca tagcctgcat ttgaaactgt atttcttgag tgctggagag gcaatcggaa    660

ttccgtgtgt agcggtgaaa tgcgtagata tacggaggaa caccagtggc gaagcggatt    720

gctggacagt aactgacgct gaggcgcgaa agcgtgggga gcaaacaggg attagatacc    780

ctggtagtca cgccgtaaac gatggatact aggtgtgggg ggactgaccc cctccgtgcc    840

gcagctaacg caataagtat cccacctggg gagtacgatc gcaagggttg aaactcaaag    900

gaattgacgg gggcccgcac aagcggtgga gtatgtggtt taattcgaag caacgcgaag    960

aaccttacca gggcttgaca tcctgctaac gaaccagaga tggatcaggt gcccttcggg   1020

gaaagcagag acaggtggtg catggttgtc gtcagctcgt gtcgtgagat gttgggttaa   1080

gtcccgcaac gagcgcaacc cctattgtta gttgctacgc aagagcactc tagcgagact   1140

gccgttgaca aaacggagga aggtggggac gacgtcaaat catcatgccc cttacgtcct   1200

gggccacaca cgtactacaa tggcggccaa caaagagagg caagaccgcg aggtggagca   1260

aatctcaaaa agccgtccca gttcggatcg caggctgcaa cccgcctgcg tgaagttgga   1320

atcgctagta atcgcggatc agcatgccgc ggtgaatacg ttcccgggcc ttgtacacac   1380

cgcccgtcac accatgagag tcgggaacac ccgaagtccg tagcctgacc gcaagggggg   1440

cgcggccgaa ggtgggttcg ataattgggg tgaagtagta acaaggtagc cgt           1493
```

<210> SEQ ID NO 38
<211> LENGTH: 1493
<212> TYPE: DNA
<213> ORGANISM: Clostridium leptum
<220> FEATURE:
<221> NAME/KEY: rRNA
<222> LOCATION: (1)..(1493)
<223> OTHER INFORMATION: 16S rRNA coding gene sequence of Clostridium
strain 18

<400> SEQUENCE: 38

```
agagtttgat cctggctcag gacgaacgct ggcggcgcgc ctaacacatg caagtcgaac     60
```

```
ggagcttata tttcagaagt tttcggatgg acgagagata agcttagtgg cggacgggtg    120
agtaacacgt gagcaacctg cctttcagag ggggataaca gttggaaacg actgctaata    180
ccgcataacg ctgcgatggg gcatcccgat gcagccaaag gagcaatccg ctgaaagatg    240
ggctcgcggc cgattagcta gttggtgggg caacggccca ccaaggcgac gatcggtagc    300
cggactgaga ggttgatcgg ccacattggg actgagacac ggcccagact cctacgggag    360
gcagcagtgg gggatattgc acaatggagg aaactctgat gcagcgacgc cgcgtgaggg    420
aagacggtct tcggattgta aacctctgtc tttggggaag aaaatgacgg tacccaaaga    480
ggaagctccg gctaactacg tgccagcagc cgcggtaata cgtacggagc gagcgttgtc    540
cggaattact gggtgtaaag ggagcgtacg cgggcgagaa agttgaatgt taaatctacc    600
ggcttaactg gtagctgcgt tcaaaacttc ttgtcttgag tgaagtagag gcaggcggaa    660
ttcctagtgt agcggtgaaa tgcgtagata taggaggaca ccagtgggcg aagccgcctg    720
ctgggcttta actgacgctg aggctcgaaa gcgtggggag caaaccagga ttagataccc    780
tggtagtcaa cgctgtaaac gatgattact aggtgtgggg gggactgacc ccctccgtgc    840
cgcagttaac acaataagta tccacctggg gagtacggcc gcaaagtttg aaaactcaaa    900
aggaatgacg gggcccgca caaagcagtg gagtatgtgg tttaatttcg aagcaacgcg    960
aagaacctta ccaggtcttg acatcgtgcg catagcctag agataggtga agcccttcgg   1020
ggcgcacaga caggtggtgc atggttgtcg tcagctcgtg tcgtgagatg ttgggttaag   1080
tcccgcaacg agcgcaaccc ttattattag ttgctacgca agagcactct aatgagactg   1140
ccgttgacaa aacggaggaa ggtggggatg acgtcaaatc atcatgcccc ttatgacctg   1200
ggctacacac gtactacaat ggcactgaaa cagagggaag cgacatcgcg aggtgaagcg   1260
aatcccaaaa aagtgtccca gttcggattg caggctgcaa ctcgcctgca tgaagtcgga   1320
attgctagta atcgcggatc agcatgccgc ggtgaatacg ttcccgggcc ttgtacacac   1380
cgcccgtcac accatgggag tcggtaacac ccgaagccag tagcctaacc gcaaggaggg   1440
cgctgtcgaa ggtgggattg atgactgggg tgaagtcgta acaaggtagc cgt          1493
```

<210> SEQ ID NO 39
<211> LENGTH: 1483
<212> TYPE: DNA
<213> ORGANISM: Clostridium leptum
<220> FEATURE:
<221> NAME/KEY: misc_feature
<222> LOCATION: (1)..(1483)
<223> OTHER INFORMATION: 16S rRNA coding gene sequence of Clostridium strain 19

<400> SEQUENCE: 39

```
agagtttgat cctggctcag gacgaacgct ggcggcacgc ctaacacatg caagtcgaac     60
ggagtgaaga tgcttgcatc tgaacttagt ggcggacggg tgagtaacac gtgagcaacc    120
tgcctttcag agggggataa cgtttggaaa cgaacgctaa taccgcataa aatatcggag    180
tcgcatggca ctgatatcaa aggagcaatc cgctgaaaga tgggctcgcg tccgattagg    240
cagttggcgg ggtaacggcc caccaaaccg acaatcggta gccggactga gaggttgaac    300
ggccacattg ggactgagac acggcccaga ctcctacggg aggcagcagt gggggatatt    360
gcacaatggg ggaaaccctg atgcagcgat gccgcgtgaa tgaagacggc cttcgggttg    420
taaagttctg tcgcagggga cgaaaatgac ggtaccctgc aagaaagctc cggctaacta    480
cgtgccagca gccgcggtaa tacgtaggga gcaagcgttg tccggaatta ctgggtgtaa    540
```

```
agggagcgta ggcgggagga taaagttgaa tgtgaaatct atgggctcaa cccatagctg    600

cgttcaaaac tgttcttctt gagtgaagta gaggcaggcg gaattcctag tgtagcggtg    660

aaatgcgtag atattaggag gaacaccagt ggcgaaagcg gcctgctggg cttttactga    720

cgctgaggct cgaaagcgtg ggtagcaaac agaattagat accctgtta ttcacggcgg    780

taaacgatga ttactaggtt tgggttgacc tgacccccat tcgtgccgga agtaacacca    840

taaagtaatc cacctggggg agtacggccg ccaggttgaa acttcaaaag gaattgacgg    900

gggcccgcac aagcagtgga ggtatgtggt ttaatttcga cgcaaacgcg aagaacctta    960

ccagggtctt gacatcgagt gacggacata gagatatgtc tttcctttcg ggacacgaag   1020

acaggtggtg catggttgtc gtcagctcgt gtcgtgagat gttgggttaa gtcccgcaac   1080

gagcgcaacc cttaccatta gttgctacgc aagagcactc tgatgggact gccgttgaca   1140

aaacggagga aggtggggat gacgtcaaat catcatgccc cttatgacct gggcgacaca   1200

cgtactacaa tggcggtcaa cagagggagg caaagccgcg aggcagagca aacccctaaa   1260

agccgtctca gttcggattg caggctgcaa ctcgcctgca tgaagtcgga attgctagta   1320

atcgcggatc agcatgccgc ggtgaatacg ttcccgggcc ttgtacacac cgcccgtcac   1380

accatgagag ccggtaacac ccgaagtcaa tagtctaacc gcaaggagga cattgccgaa   1440

ggtgggattg gtaattgggg tgaagtcgta acaaggtagc cgt                     1483


<210> SEQ ID NO 40
<211> LENGTH: 1511
<212> TYPE: DNA
<213> ORGANISM: Clostridium coccoides
<220> FEATURE:
<221> NAME/KEY: rRNA
<222> LOCATION: (1)..(1511)
<223> OTHER INFORMATION: 16S rRNA coding gene sequence of Clostridium
      strain 20

<400> SEQUENCE: 40

agagtttgat cctggctcag gatgaacgct ggcggcgtgc ttaacacatg caagtcgaac     60

gggctcatat tgaaacctag tgatgtatga gttagtggcg gacgggtgag taacgcgtgg    120

agaacctgcc gtatactggg ggataacact tagaaatagg tgctaatacc gcataagcgc    180

acagcttcgc atgaaacagt gtgaaaaact ccggtggtat acgatggatc cgcgtctgat    240

tagctggttg gcggggtaac agcccaccaa ggcgacgatc agtagccggc ctgagagggt    300

gaacggccac attgggactg agacacggcc caaactccta cgggaggcag cagtggggaa    360

tattgcacaa tgggggaaac cctgatgcag cgacgccgcg tgagtgaaga agtatttcgg    420

tatgtaaagc tctatcagca gggaagaaat actgacctta cggtcagcag acggtacctg    480

actaagaagc cccggctaac tacgtgccag cagccgcggt aatacgtagg ggcaagcgtt    540

atccggattt actgggtgta aagggagcgt agacggcagc gcaagtctga gtgaaatccc    600

atggcttaac catggaactg ctttggaaac tgtgcagctg gagtgcagga gaggtaaagc    660

ggaattccta gtgtagcggg tgaaatgcgt agatatagga ggaacaacag tggcggaagg    720

cggctactgg gactgtaact gacgttgagg ctcgaaagcg tggggagcaa acaggattag    780

ataccctggt agtcacgccg taaacgatga ttactaggtg ttgggggacc ataggtcttc    840

ggtgccggcg caaacgcaat taagtaatcc acctggggga gtacgttcgc aagaatgaaa    900

ctcaaaggaa ttgacgggga cccgcacaaa gcggtggagc atgtggttta attcgaaagc    960

aaacgcgaag aaaccttacc tggtcttgac atcccgatga cgagtgagca aagtcacttt   1020
```

-continued

```
cccttcgggg caattggaga caggtggtgc atgggttgtc gtcagctcgt gtcgtgagat   1080

gttgggttaa gtcccgcaac gagcgcaacc cctatttcca gtagccagca ggtagagctg   1140

ggcactctgg agagactgcc cgggataacc gggaggaagg cggggatgac gtcaaatcat   1200

catgcccctt atgatcaggg ctacacacgt gctacaatgg cgtaaacaaa gggaagcgag   1260

acggtgacgt taagcaaatc ccaaaaataa cgtcccagtt cggattgtag tctgcaactc   1320

gattacatga agctggaatc gctagtaatc gcgaatcaga atgtcgcggt gaatacgttc   1380

ccgggtcttg tacacaccgc ccgtcacacc atgggagtcg gaaatgcccg aagtcagtga   1440

cctaaccgaa aggaaggagc tgccgaaggt ggagccggta actggggtga agtagataac   1500

aaggtagccg t                                                        1511
```

```
<210> SEQ ID NO 41
<211> LENGTH: 1495
<212> TYPE: DNA
<213> ORGANISM: Clostridium leptum
<220> FEATURE:
<221> NAME/KEY: rRNA
<222> LOCATION: (1)..(1495)
<223> OTHER INFORMATION: 16S rRNA coding gene sequence of Clostridium
      strain 21

<400> SEQUENCE: 41

agagtttgat cctgcgctca ggacgaacgc tggcggcgcg cctaacacat gcaagtcgaa     60

cgggactatt ttgggagaag ttttcggatg gatctcggga tagtttagtg gcggacgggt    120

gagtaacgcg tgggcaacct gccttacaca gggggataac aattagaaat gattgctaat    180

accgcataag accacggtac tgcatggtac agtggtaaaa actgaggtgg tgtaagatgg    240

gcccgcgtct gattaggtag ttggtggggt agaagcctac caagccgacg atcagtagcc    300

gacctgagag ggcgaccggc cacattggga ctgagacacg gcccaaactc ctacgggagg    360

cagcagtggg gaatattgca caatggggga aaccctgatg cagcgacgcc gcgtgagtga    420

ggaagtattt cggtatgtaa agctctatca gcagggaaga aaatgacggt acctgactaa    480

gaagccccgg ctaactacgt gccagcagcc gcggtaatac gtagggggca agcgttatcc    540

ggatttactg ggtgtaaagg gagcgtagac ggacttgcaa gtctgatgtg aaaatccggg    600

ggcccaaccc cggaactgca ttggaaactg tatatctaga gtgtcggaga ggcaagtgga    660

atttcctggt gtagcggtga aatgcgtaga tatcagagga acaccagtgg cgaaggcgct    720

tgcctgacga tgactgacgt tgaagctcga aaagcgtggg tagcaaacag aattagatac    780

cctggtaagt caacccggta aacgatgatt actaggtttt ggttggactg accccatccg    840

tgccggagta acaccaataa gttatccaac ctgggaagta cggccggcag gttgaaactc    900

aaaaggaaat gacgggggcc cgcacaagca gttgaagtat gtgggttaat tcgacgcaaa    960

cgcgaagaac cttaccaggt cttgacatcg agtgacggac atagagatat gtctttcctt   1020

cgggacacga agacaggtgg tgcatggttg tcgtcagctc gtgtcgtgag atgttgggtt   1080

aagtcccgca acgagcgcaa cccttaccat tagttgctac gcaagagcac tctgatggga   1140

ctgccgttga caaaacggag gaaggtgggg atgacgtcaa atcatcatgc cccttatgac   1200

ctgggcgaca cacgtactac aatggcggtc aacagaggga ggcaaagccg cgaggcagag   1260

caaaccccta aaagccgtct cagttcggat tgcaggctgc aactcgcctg catgaagtcg   1320

gaattgctag taatcgcgga tcagcatgcc gcggtgaata cgttcccggg ccttgtacac   1380

accgcccgtc acaccatgag agccggtaac acccgaagtc aatagtctaa ccgcaaggag   1440
```

```
gacattgccg aaggtgggat tggtaattgg ggtgaagtcg taacaaggta gccgt        1495


<210> SEQ ID NO 42
<211> LENGTH: 1491
<212> TYPE: DNA
<213> ORGANISM: Clostridium leptum
<220> FEATURE:
<221> NAME/KEY: rRNA
<222> LOCATION: (1)..(1491)
<223> OTHER INFORMATION: 16S rRNA coding gene sequence of Clostridium
      strain 22

<400> SEQUENCE: 42

agagtttgat cctggctcag gatgaacgct ggcggcgtgc ttaacacatg caagtcgaac     60

gagaatccag tgaaggagtt ttcggacaac ggatctggag gaaagtggcg gacgggtgag    120

taacgcgtga gcaatctgcc ttggagtggg gaataacggt tggaaacagc cgctaatacc    180

gcatgatgcg tctgggaggc atctctctgg acgccaaaga tttatcgctc tgagatgagc    240

tcgcgtctga ttagcttgtt ggcggggtaa aggcccacca aggcgacgat cagtagccgg    300

actgagaggt tggccggcca cattgggact gagacacggc ccagactcct acgggaggca    360

gcagtgggga atattgggca atgggcgcaa gcctgaccca gcaacgccgc gtgaaggaag    420

aaggctttcg ggttgtaaac ttcttttctg agggacgaag aaagtgacgg tacctcagga    480

ataagccacg gctaactacg tgccagcagc cgcggtaata cgtaggtggc aagcgttatc    540

cggatttatt gggtgtaaag ggcgtgtagg cgggaaagca agtcagatgt gaaaactcag    600

ggctcaaccc tgagcctgca tttgaaactg tttttcttga gtgctggaga ggcaatcgga    660

attccgtgtg tagcggtgaa atgcgtagat atacggagga caccagtggc gaagcggatt    720

gctggacagt aactgacgct gaggcgcgaa gcgtggggag caaacaggat tagataccct    780

ggtagtccac gccgtaaacg atggatacta ggtgtggggg gactgacccc ctccgtgccg    840

cagctaacgc aataagtatc ccacctgggg agtacgatcg caaggttgaa actcaaagga    900

attgacgggg gcccgcacaa gcggtggagt atgtggttta attcgaagca acgcgaagaa    960

ccttaccagg gcttgacatc ctgctaacga accagagatg gattaggtgc ccttcgggga   1020

aagcagagac aggtggtgca tggttgtcgt cagctcgtgt cgtgagatgt tgggttaagt   1080

cccgcaacga gcgcaaccct tattgttagt tgctacgcaa gagcactcta gcgagactgc   1140

cgttgacaaa acggaggaag gtggggacga cgtcaaatca tcatgcccct tacgtcctgg   1200

gccacacacg tactacaatg gcggccaaca aagagaggca agaccgcgag gtggagcaaa   1260

tctcaaaaag ccgtcccagt tcggatcgca ggctgcaacc cgcctgcgtg aagttggaat   1320

cgctagtaat cgcggatcag catgccgcgg tgaatacgtt cccgggcctt gtacacaccg   1380

cccgtcacac catgagagtc gggaacaccc gaagtccgta gcctaaccgc aaggggggcg   1440

cggccgaagg tgggttcgat aattggggtg aagtcgtaac aaggtagccg t            1491


<210> SEQ ID NO 43
<211> LENGTH: 1495
<212> TYPE: DNA
<213> ORGANISM: Clostridium leptum
<220> FEATURE:
<221> NAME/KEY: rRNA
<222> LOCATION: (1)..(1495)
<223> OTHER INFORMATION: 16S rRNA coding gene sequence of Clostridium
      strain 23

<400> SEQUENCE: 43

agagtttgat cctgtgcctc aggatgaacg ctggcggcgt gcttaacaca tgcaagtcga     60
```

-continued

```
acgagaacca acggattgag gattcgtcca aatgaagttg gggaaagtgg cggacgggtg    120

agtaacgcgt gagcaatctg ccttggagtg gggaataacg gttggaaaca gccgctaata    180

ccgcatgatg cgtctgggag gcatctctct ggacgccaaa gatttatcgc tctgagatga    240

gctcgcgtct gattagctag ttggcggggc aacggcccac caaggcgacg atcagtagcc    300

ggactgagag gttggccggc cacattggga ctgagacacg gcccagactc ctacgggagg    360

cagcagtggg gaatattggg caatgggcgc aagcctgacc cagcaacgcc gcgtgaagga    420

agaaggcttt cgggttgtaa acttctttta agggggacga acaaatgacg gtaccccttg    480

aataagccac ggctaactac gtgccagcag ccgcggtaat acgtaggtgg caagcgttat    540

ccggatttat tgggtgtaaa gggcgtgtag gcgggaatgc aagtcagatg tgaaaactat    600

gggctcaacc catagcctgc atttgaaact gtatttcttg agtgctggag aggcaatcgg    660

aattccgtgt gtagcggtga aatgcgtaga tatacggagg aacaccagtg gcgaaggcgg    720

attgctggac agtaactgac gctgaggcgc gaaagcgtgg ggagcaaaca ggattagata    780

ccctggtagt ccacgccgta aacgatggat actaagtgtg gggggactga cccccctccgt    840

gccgcagcta acgcaataag tatcccacct ggggagtacg atcgcaaggt tgaaactcaa    900

aggaattgac gggggcccgc acaagcggtg gagtatgtgg tttaattcga agcaacgcga    960

agaaccttac cagggcttga catcctgcta acgaaccaga gatggatcag gtgcccttcg   1020

gggaaagcag agacaggtgg tgcatggttg tcgtcagctc gtgtcgtgag atgttgggtt   1080

aagtcccgca acgagcgcaa cccctattgt tagttgctac gcaagagcac tctagcgaga   1140

ctgccgttga caaaacggag gaaggtgggg acgacgtcaa atcatcatgc cccttacgtc   1200

ctgggccaca cacgtactac aatggcggcc aacaaagaga ggcaagaccg cgaggtggag   1260

caaatctcaa aaagccgtcc cagttcggat cgcaggctgc aacccgcctg cgtgaagttg   1320

gaatcgctag taatcgcgga tcagcatgcc gcggtgaata cgttcccggg ccttgtacac   1380

accgcccgtc acaccatgag agtcgggaac acccgaagtc cgtagcctga ccgcaagggg   1440

ggcgcggccg aaggtgggtt cgataattgg ggtgaagtcg taacaaggta gccgt        1495


<210> SEQ ID NO 44
<211> LENGTH: 1440
<212> TYPE: DNA
<213> ORGANISM: Clostridium leptum
<220> FEATURE:
<221> NAME/KEY: rRNA
<222> LOCATION: (1)..(1440)
<223> OTHER INFORMATION: 16S rRNA coding gene sequence of Clostridium
      strain 24

<400> SEQUENCE: 44

agagtttgat cctggctcag gacgaacgct ggcggcacgc ctaacacatg caagtcgaac     60

ggagtgaaga tgctcgcatc tgaacttagt ggcggacggg tgagtaacac gtgagcaacc    120

tgcctttcag agggggataa cgtttggaaa cgaacgctaa taccgcataa aatatcggag    180

tcgcatggca ctgatatcaa aggagtaatc cgctgaaaga tgggctcgcg tccgattagg    240

cagttggcgg ggtaacggcc caccaaaccg acaatcggta gccggactga gaggttgaac    300

ggccacattg ggactgagac acggcccaga ctcctacggg aggcagcagt gggggatatt    360

gcacaatggg ggaaaccctg atgcagcgat gccgcgtgaa tgaagacggc cttcgggttg    420

taaagttctg tcgcagggga cgaaaatgac ggtaccctgc aagaaagctc cggctaacta    480

cgtgccagca gccgcggtaa tacgtaggga gcaagcgttg tccggaatta ctgggtgtaa    540
```

agggagcgta ggcgggagga taagttgaat gtgaaatcta tgggctcaac ccatagttgc 600
gttcaaaact gttcttcttg agtgaagtag aggcaggcgg aattcctagt gtagcggtga 660
aatgcgtaga tattagagga acaccagtgg cgaagcggcc tgctgggctt ttactgacgc 720
tgagctcgaa agcgtgggta gcaacaggat tagataccct ggtagtccac gcggtaaacg 780
atgattacta gtgtgggtgg actgacccat ccatgccgga gttaacacaa tagtaatcca 840
cctggggagt acgcgcagtg aactcaaagg attgacgggg cccgcacaag cagtgagtat 900
gtggtttatt cgacgcacgc gagactacag tcttgacatc gatgacggac tagagatatg 960
tctttctcgg acacgaagac aggtggtgca tggttgtcgt cagctcgtgt cgtgagatgt 1020
tgggttaagt cccgcaacga gcgcaaccct taccattagt tgttacgcaa gagcactcta 1080
atgggactgc cgttgacaaa acggaggaag gtggggatga cgtcaaatca tcatgcccct 1140
tatgacctgg gcgacacacg tactacaatg gcggtcaaca gagggaggca aagccgcgag 1200
gcagagcaaa cccctaaaag ccgtctcagt tcggattgca ggctgcaact cgcctgcatg 1260
aagtcggaat tgctagtaat cgcggatcag catgccgcgg tgaatacgtt cccgggcctt 1320
gtacacaccg cccgtcacac catgagagcc ggtaacaccc gaagtcaata gtctaaccgc 1380
aaggaggaca ttgccgaagg tgggatggta attggggtga agtagtaaca aggtagccgt 1440

<210> SEQ ID NO 45
<211> LENGTH: 1495
<212> TYPE: DNA
<213> ORGANISM: Clostridium leptum
<220> FEATURE:
<221> NAME/KEY: rRNA
<222> LOCATION: (1)..(1495)
<223> OTHER INFORMATION: 16S rRNA coding gene sequence of Clostridium
strain 25

<400> SEQUENCE: 45
agagtttgat cctggctcag gatgaacgct ggcggcgtgc ttaacacatg caagtcgaac 60
gagaaccatt ggatcgagga ttcgtccaag tgaaggtggg gaaagtggcg gacgggtgag 120
taacgcgtga gcaatctgcc ttggagtggg gaataacggc tggaaacagc cgctaatacc 180
gcatgataca gctgggaggc atctccctgg ctgtcaaaga tttatcgctc tgagatgagc 240
tcgcgtctga ttagctagtt ggcggggtaa cggcccacca aggcgacgat cagtagccgg 300
actgagaggt tggccggcca cattgggact gagacacggc ccagactcct acgggaggca 360
gcagtgggga atattgggca atgggcgcaa gcctgaccca gcaacgccgc gtgaaggaag 420
aaggctttcg ggttgtaaac ttcttttgtc agggacgaag caagtgacgg tacctgacga 480
ataagccacg gctaactacg tgccagcagc cgcggtaata cgtagtggca agcgttatcc 540
ggatttattg ggtgtaaag ggcgtgtagg cgggaatgca agtcagatgt gaaaactatg 600
gggctcaacc catagcctgc atttgaaact gtatttcttg agtgctggag aggcaatcga 660
attccgtgtg tagcgggtga aatgcgtaga tatacggagg aacaccagtg gcgaagcgga 720
ttgctggaca agtaactgac gctgaggcgc gaaagcgtgg ggagcaaaca ggattagata 780
ccctggtagt ccacgccgta aacgatggat actaggtgtg gggggactga ccccctccgt 840
gccgcagcta acgcaataag tatcccacct ggggagtacg atcgcaaggt tgaaactcaa 900
aggaattgac gggggcccgc acaagcggtg gagtatgtgg tttaattcga cgcaacgcga 960
agaaccttac cagggcttga catcctacta acgaaccaga gatggattag gtgcccttcg 1020
gggaaagtag agacaggtgg tgcatggttg tcgtcagctc gtgtcgtgag atgttgggtt 1080

```
aagtcccgca acgagcgcaa cccctattgt tagttgctac gcaagagcac tctagcgaga   1140

ctgccgttga caaaacggag gaaggtgggg acgacgtcaa atcatcatgc cccttacgtc   1200

ctgggccaca cacgtactac aatggcggcc aacaaagaga ggcaaagccg cgaggtggag   1260

caaatctcaa aaagccgtcc cagttcggat cgcaggctgc aacccgcctg cgtgaagttg   1320

gaatcgctag taatcgcgga tcagcatgcc gcggtgaata cgttcccggg ccttgtacac   1380

accgcccgtc acaccatgag agtcgggaac acccgaagtc cgtagcctaa ccgcaagggg   1440

ggcgcggccg aaggtgggtt cgataattgg ggtgaagtcg taacaaggta gccgt        1495


<210> SEQ ID NO 46
<211> LENGTH: 1495
<212> TYPE: DNA
<213> ORGANISM: Clostridium leptum
<220> FEATURE:
<221> NAME/KEY: rRNA
<222> LOCATION: (1)..(1495)
<223> OTHER INFORMATION: 16S rRNA coding gene sequence of Clostridium
      strain 26

<400> SEQUENCE: 46

agagtttgat catggctcag gacgaacgct ggcggcgtgc ttaacacatg caagtcgaac     60

ggagcacccc tgaaggagtt ttcggacaac ggatgggaat gcttagtggc ggactggtga    120

gtaacgcgtg aggaacctgc cttccagagg gggacaacag ttggaaacga ctgctaatac    180

cgcatgatgc gttggagccg catgactccg acgtcaaaga tttatcgctg gaagatggcc    240

tcgcgtctga ttagctagtt ggtgaggtaa cggcccacca aggcgacgat cagtagccgg    300

actgagaggt tggccggcca cattgggact gagatacggc ccagactcct acgggaggca    360

gcagtgggga atattgggca atggacgcaa gtctgaccca gcaacgccgc gtgaaggaag    420

aaggctttcg ggttgtaaac ttcttttaag gggaagagc agaagacggt accccttgaa    480

taagccacgg ctaactacgt gccagcagcc gcggtaatac gtaggtggca agcgttgtcc    540

ggatttactg ggtgtaaagg gcgtgcagcc ggagagacaa gtcagatgtg aaatccacgg    600

gctcaacccg tgaactgcat ttgaaactgt ttcccttgag tgtcggagag ggtaatcgga    660

attcctttgt gtagcggtga aatgcgtaga tataagaaga acaccagtgg cgaaggcgga    720

ttactggacg ataactgacg gtgaggcgcg aaagcgtggg ggagcaacag attaaatacc    780

ctggtagtcc acgctgttaa cgatcgatac taggtgtgcc gggactgacc ccctgcgtgc    840

ccggagttaa ccacaataag tatcgcacct ggggagtacg atcgcaaggt gaacttcaaa    900

ggaattgacg gggcccgcc ccaagccgtg gattatgtgg ttaattcgaa gcaacgcgaa    960

gaacctaccc agggcttgac atcctgctaa cgaagtagag atacattagg tgccctttcg   1020

gggaaagcag agacaggtgg tgcatggttg tcgtcagctc gtgtcgtgag atgttgggtt   1080

aagtcccgca acgagcgcaa cccctattgt tagttgctac gcaagagcac tctagcgaga   1140

ctgccgttga caaaacggag gaaggcgggg acgacgtcaa atcatcatgc cccttatgtc   1200

ctgggctaca cacgtaatac aatggcggtt aacaaaggga tgcaaagccg cgaggcagag   1260

cgaaccccaa aaagccgtcc cagttcggat cgcaggctgc aacccgcctg cgtgaagtcg   1320

gaatcgctag taatcgcgga tcagcatgcc gcggtgaata cgttcccggg ccttgtacac   1380

accgcccgtc acaccatgag agtcgggaac acccgaagtc cgtagcctaa ccgcaaggag   1440

ggcgcggccg aaggtgggtt cgataattgg ggtgaagtcg taacaaggta gccgt        1495
```

<210> SEQ ID NO 47
<211> LENGTH: 1509
<212> TYPE: DNA
<213> ORGANISM: Clostridium leptum
<220> FEATURE:
<221> NAME/KEY: rRNA
<222> LOCATION: (1)..(1509)
<223> OTHER INFORMATION: 16S rRNA coding gene sequence of Clostridium strain 27

<400> SEQUENCE: 47

```
agagtttgat cctggctcag gatgaacgct ggcggcgtgc ttaacacatg caagtcgaac     60

ggagtacccc tgaaggagtt ttcggacaac tgatgggact acttagtggc ggacgggtga    120

gtaacgcgtg agtaacctgc cttggagtgg ggaataacag ctggaaacag ctgctaatac    180

cgcataatat gtctgtgtcg catggcactg gacatcaaag atttatcgct ctgagatgga    240

ctcgcgtctg attagctagt tggcggggta acggcccacc aaggcgacga tcagtagccg    300

gactgagagg ttggccggcc acattgggac tgagacacgg cccagactcc tacgggaggc    360

agcagtgggg aatattgggc aatgggcgca agcctgaccc agcaacgccg cgtgaaggaa    420

gaaggctttc gggttgtaaa cttcttttaa gggggaagag cagaagacgg taccccttga    480

ataagccacg gctaactacg tgccagcagc cgcggtaata cgtaggtggc aagcgttgtc    540

cggatttact gggtgtaaag ggcgtgcagc cggagagaca agtcagatgt gaaatccacg    600

ggctcaaccc gtgaactgca tttgaaactg tttcctggag ttcggagggt atggaattct    660

tgttagcggt gaaatgctgt agatatggga gaaccaccag tgcgaggggg cttccgggac    720

tgtacttgac tgtagaggtc tcaaagctgg gggagcaccg aggaatgaga taccgtgata    780

gtcccacgcg gtaacggatg attactaggt gttgggggga cccaggctct ttcggtgccg    840

ggcgcaaacc ctttaggaat tccacctggg gaattacgtt tggcaagaaa ggaacttcaa    900

agaaattgaa cgggggaccc ccccaaccgg tggaggcatg gtgttttatt tcggaggaac    960

gggaagaacc tttaccttgt tctgaccttc cggatgacga agtgagcaaa gtcaacttcc   1020

cttcggggcc atggaggaca ggtggtggca tggttggtcg tcagctcgtg tcgtgagatg   1080

ttgggttaag tcccgcaacg agcgcaaccc ctatttccag tagccagcag gtagagctgg   1140

gcactctgga gagactgccc gggataaccg ggaggaaggc ggggatgacg tcaaatcatc   1200

atgcccctta tgatcagggc tacacacgtg ctacaatggc gtaaacaaag ggaagcgaga   1260

cggtgacgtt aagcaaatcc caaaaataac gtcccagttc ggattgtagt ctgcaactcg   1320

actacatgaa gctggaatcg ctagtaatcg cgaatcagaa tgtcgcggtg aatacgttcc   1380

cgggtcttgt acacaccgcc cgtcacacca tgggagtcgg aaatgcccga agtcagtgac   1440

ctaaccgaaa ggaaggagct gccgaaggtg gagccggtaa ctggggtgaa gtcgtaacaa   1500

ggtagccgt                                                           1509
```

<210> SEQ ID NO 48
<211> LENGTH: 1583
<212> TYPE: DNA
<213> ORGANISM: Clostridium leptum
<220> FEATURE:
<221> NAME/KEY: rRNA
<222> LOCATION: (1)..(1583)
<223> OTHER INFORMATION: 16S rRNA coding gene sequence of Clostridium strain 28

<400> SEQUENCE: 48

```
agagtttgat cctggctcag gacgaacgct ggcggcgcgc ctaacacatg caagtcgaac     60
```

```
ggagcttata tttcagaagt tttcggatgg acgagagata agcttagtgg cggacgggtg    120

agtaacacgt gagcaacctg cctttcagag gggataaca gttggaaacg actgctaata     180

ccgcataacg ctgcgatggg gcatcccgat gcagccaaag gagcaatccg ctgaaagatg    240

ggctcgcggc cgattagcta gttggtgggg caacggccca ccaaggcgac gatcggtagc    300

cggactgaga ggttgatcgg ccacattggg actgagacac ggcccagact cctacgggag    360

gcagcagtgg gggatattgc acaatggagg aaactctgat gcagcgacgc cgcgtgaggg    420

aagacggtct tcggattgta aacctctgtc tttggggaag aaaatgacgg tacccaaaga    480

ggaagctccg gctaactacg tgccagcagc cgcggtaata cgtaggggag cgagcgttgt    540

ccggaattac tgggtgtaaa gggagcgtag cgggcgagaa agttgaatgt taaatctacc    600

ggcttaactg gtagctgcgt ccaaaacttc ttggtcttga gtgaaagtaa gaggccaggg    660

cggaaattct tagtgtaagc gggtgaaaat gcgttagata ttagggagga accaccaggt    720

gggcgaaggg cggcttgctg ggctttaact ggacggctgg aggcttggaa aaggcgtggg    780

gagagcaaac acagggaatt aagtataccc tggtatatgt cacacgcttg taaagagtat    840

gattaactta gggtggtggg gggaacttga ccctttcgtg tgcgcgcagg ttaacacaca    900

tttagagtat atccaacttg ggagagtac ggccggcaaa gtttgaaact tcaaaaggga     960

aattgagacc ggggggcccg gccaccaagc acagtggaga gtatggtggg tttaatttcg   1020

agaagcaacc ggcggaagag aaactttacc agtccttgac atcggtggcg gcataagccc   1080

tagagattag gtgaagccct tcgggggccc caccagacag gtggtgcatg gttgtcgtca   1140

gctcgtgtcg tgagatgttg ggttaagtcc ccgcaaacga gcgcaaccct tattattagt   1200

ttgctacgca agagcactct aatgagactg ccgttgacaa aacggaggaa ggtggggatg   1260

acgtcaaatc atcatgcccc ttatgacctg ggctacacac gtactacaat ggcactgaaa   1320

cagagggaag cgacatcgcg aggtgaagcg aatcccaaaa aagtgtccca gttcggattg   1380

caggctgcaa ctcgcctgca tgaagtcgga attgctagta atcgcggatc agcatgccgc   1440

ggtgaatacg ttcccgggcc ttgtacacac cgcccgtcac accatgggag tcggtaacac   1500

ccgaagccag tagcctaacc gcaaggaggg cgctgtcgaa ggtgggattg atgactgggg   1560

tgaagtcgta acaaggtagc cgt                                           1583


<210> SEQ ID NO 49
<211> LENGTH: 1519
<212> TYPE: DNA
<213> ORGANISM: Clostridium coccoides
<220> FEATURE:
<221> NAME/KEY: rRNA
<222> LOCATION: (1)..(1519)
<223> OTHER INFORMATION: 16S rRNA coding gene sequence of Clostridium
      strain 29

<400> SEQUENCE: 49

agagtttgat catggctcag gatgaacgct ggcggcgtgc ctaacacatg caagtcgaac     60

gggtgtacgg gaaggaaggc ttcggccgga aaacctgtgc atgagtggcg gacgggtgag    120

taacgcgtgg gcaacctggc ctgtacaggg ggataacact tagaaatagg tgctaatacc    180

gcataacggg ggaagccgca tggcttttcc ctgaaaactc cggtggtaca ggatgggccc    240

gcgtctgatt agccagttgg cagggtaacg gcctaccaaa gcgacgatca gtagccggcc    300

tgagagggcg gacggccaca ctgggactga gacacggccc agactcctac gggaggcagc    360

agtgggggat attgcacaat gggggaacc ctgatgcagc gacgccgcgt gggtgaagaa     420
```

-continued gcgcctcggc gcgtaaagcc ctgtcagcag ggaaagaaaa tgacggtacc tgaagaagaa 480
gccccgggct aactacgtgc cagcagccgg cggtaattac gtagggggc aggcgttatc 540 cggatttact gggtggtaaa ggggggcgca aacggcgatg gcaggccagg aatggaaagc 600
ccgggggccc aaccccggga cttgctcttg ggaaactggc ttggctggga gtggcaggag 660
gggcaggcgg aaattcctgg tggtagcggt ggaaaatggc taaaaatcaa gaagaaaaac 720
cggtggggaa aggcggcctg gtgggactgc gaactgacgt tgaaggcccg aaagcgtggg 780
gaacaaacag gatagattcc ctggtagttc cacgccgtaa acgatgatta ctaggtgtcg 840
gggagcagag actgcccggt gccgcagcca acgcattaag taatccacct ggggagtacg 900
ttcgcaagaa tgaaactcaa aggaattgac ggggacccgc acaagcggtg gagcatgtgg 960
tttaattcga agcaacgcga agaaccttac ctggtcttga catcccgatg acgagtgagc 1020
aaagtcactt tcccttcggg gcattggaga caggtggtgc atggttgtcg tcagctcgtg 1080
tcgtgagatg ttgggttaag tcccgcaacg agcgcaaccc ctatttccag tagccagcag 1140
gtagagctgg gcactctgga gagactgccc gggataaccg ggaggaaggc ggggatgacg 1200
tcaaatcatc atgcccctta tgatcagggc tacacacgtg ctacaatggc gtaaacaaag 1260
ggaagcgaga cggtgacgtt aagcaaatcc caaaaataac gtcccagttc ggattgtagt 1320
ctgcaactcg actacatgaa gctggaatcg ctagtaatcg cgaatcagaa tgtcgcggtg 1380
aatacgttcc cgggtcttgt acacaccgcc cgtcacacca tgggagtcgg aaatgcccga 1440
agtcagtgac ctaaccgaaa ggaaggagct gccgaaggtg gagccggtaa ctggggtgaa 1500
gtcgtaacaa ggtagccgt 1519

<210> SEQ ID NO 50
<211> LENGTH: 1497
<212> TYPE: DNA
<213> ORGANISM: Clostridium coccoides
<220> FEATURE:
<221> NAME/KEY: rRNA
<222> LOCATION: (1)..(1497)
<223> OTHER INFORMATION: 16S rRNA coding gene sequence of Clostridium strain 30

<400> SEQUENCE: 50
agagtttgat cctggctcag gatgaacgct ggcggcgtgc ctaacacatg caagtcgaac 60
ggggtatata agcggaagtt tacggatgga aggttatata cttagtggcg gacgggtgag 120
taacgcgtgg gcaacctgcc ccgtgccggg ggataccgcc tggaaacagg cgctaatacc 180
gcataagcgc atacagccgc atgggtgtat gcggaaagct ccggcggcac gggatgggcc 240
cgcgcccgat tagccagttg gcggggtaac ggcccaccaa agcgacgatc ggtagccggc 300
ctgagagggc ggacggccac attgggactg agacacggcc caaactccta cgggaggcag 360
cagtggggaa tattgcacaa tgggggaaac cctgatgcag caacgccgcg tgggtgaagg 420
agcgtttcgg cgcgtaaagc cctgtcagcg ggaagaaga aagacggtac ccgaccaaga 480
agccccggct aactacgtgc cagcagccgc ggtaatacgt agggggcgag cgttatccgg 540
aattactggg tgtaaaggga gcgtagacgg cgaggtaagc ctgaagtgga agcccgcggc 600
ccaaccgcgg aactgctttg ggaactgttt tgctggagta tgggaggggt aagcggaatt 660
cctggtgtag cggtgaaatg cgtagatatc aggaggaaca ccggtggcga aggcggctta 720
ctggaccata actgacgttg aggctcgaaa gcgtggggag cgaacaggat tagataccct 780
ggtagtccac gcgtaaacga tgattaccag gtgtcgggtg tcgaaggacg gcccggtgcc 840

```
gcagcgaacg cagtaagtaa tccacctggg gagtacgttc gcaagaatga aactcaaagg    900

aattgacggg gacccgcaca agcggtggag catgtggttt aattcgaagc aacgcgaaga    960

accttacccg gccttgacat cccctggaca gcatatgtaa tgtatgtttc cttcgggacc   1020

agggagacag gtggtgcatg gttgtcgtca gctcgtgtcg tgagatgttg ggtcaagtcc   1080

cgcaacgagc gcaacccctg cccccagtag ccagcattta agatgggcac tctgggggga   1140

ctgccgggga taacccggag gaaggcgggg atgacgtcaa atcatcatgc cccttatggc   1200

cggggctaca cacgtgctac aatggcgtaa acagagggag gcgagacagc gatgttaagc   1260

gaaccccaaa aataacgtcc cagttcggat tgcagcctgc aactcggctg catgaagctg   1320

gaatcgctag taatcgcgga tcagaatgcc gcggtgaata cgttcccggg tcttgtacac   1380

accgcccgtc acaccatggg agtcgggaac gcccgaagcc ggtgaccgaa cccgaaaggg   1440

gaggagccgt cgaaggcggg cctggtgact ggggtgaagt cgtaacaagg tagccgt      1497


<210> SEQ ID NO 51
<211> LENGTH: 1475
<212> TYPE: DNA
<213> ORGANISM: Clostridium leptum
<220> FEATURE:
<221> NAME/KEY: rRNA
<222> LOCATION: (1)..(1475)
<223> OTHER INFORMATION: 16S rRNA coding gene sequence of Clostridium
      strain 31

<400> SEQUENCE: 51

gagtttgatc ctggctcagg ataaacgctg gcggcgcaca taagacatgc aagtcgaacg     60

aacttaatac cttgcttgca aggtaagcgg ttagtggcgg actggtgagt aacacgtaag    120

aaatctgcct atcagagggg aataacagtg agaaatcact gctaataccg catatgccat    180

agttatcgca tgataatagt gggaaagaag caattcgctg atagatgagc ttgcggctga    240

ttagctagtt ggtggggtaa cggcctacca aggcgacgat cagtagccgg cctgagaggg    300

tgaacggcca cattgggact gagacacggc ccaaactcct acgggaggca gcagtgggga    360

atattgcaca atggggggaaa ccctgatgca gcgacgccgc gtgagtgaag aagtatttcg    420

gtatgtaaag ctctatcagc agggaagaaa atgacggtac ctgactaaga aagccccggc    480

taactacgtg ccagcagccg cggtaatacg tagggggcaa gcgttatccg gatttactgg    540

tgtaaaggga gcgtagacgg cagcgcaagt ctgagtgaaa tcccatggct tacccatgaa    600

actgctttgg aaactgtgca gctggagtgc aggagaggta agcggaatcc tagtgtagcg    660

gttgaaatgc gtagattatc agaaggaaca ccggtggccg aggcggcctg ctgggctttt    720

actgacgctg aggctcgaag cgtgggtagc aaacaggatt agataccctg gtagtccacg    780

cggtaaacga tgattactag gtgtgggtgg actgacccca tccgtgccgg agttaacaca    840

ataagtaatc cacctgggga gtacggccgc aaggttgaaa ctcaaaggaa ttgacggggg    900

cccgcacaag cagtggagta tgtggtttaa ttcgacgcaa cgcgaagaac cttaccaggt    960

cttgacatcg agtgacggac atagagatat gtctttcctt cgggacacga agacaggtgg   1020

tgcatggttg tcgtcagctc gtgtcgtgag atgttgggtt aagtcccgca acgagcgcaa   1080

cccttaccat tagttgctac gcaagagcac tctaatggga ctgccgttga caaaacggag   1140

gaaggtgggg atgacgtcaa atcatcatgc cccttatgac ctgggcgaca cacgtactac   1200

aatggcggtc aacagaggga ggcaaagccg cgaggcagag caaacccccta aaagccgtct   1260

cagttcggat tgcaggctgc aactcgcctg catgaagtcg gaattgctag taatcgcgga   1320
```

tcagcatgcc gcggtgaata cgttcccggg ccttgtacac accgcccgtc acaccatgag 1380
agccggtaac acccgaagtc aatagtctaa ccgcaaggag gacattgccg aaggtgggat 1440
tggtaattgg ggtgaagtcg taacaaggta gccgt 1475

<210> SEQ ID NO 52
<211> LENGTH: 1491
<212> TYPE: DNA
<213> ORGANISM: Clostridium leptum
<220> FEATURE:
<221> NAME/KEY: rRNA
<222> LOCATION: (1)..(1491)
<223> OTHER INFORMATION: 16S rRNA coding gene sequence of Clostridium
strain 32

<400> SEQUENCE: 52
agagtttgat cctggctcag gatgaacgct ggcggcgtgc ttaacacatg caagtcgaac 60
gagaatcagt ggattgagga ttcgtccaaa tgaaactgag gaaagtggcg gacgggtgag 120
taacgcgtga gcaatctgcc ttggagtggg gaataacggc tggaaacagc cgctaatacc 180
gcatgataca gttgggaggc atctctctga ctgtcaaaga tttatcgctc tgagatgagc 240
tcgcgtctga ttagctagtt ggcggggtaa cggcccacca aggcgacgat cagtagccgg 300
actgagaggt tggccggcca cattgggact gagacacggc ccagactcct acgggaggca 360
gcagtgggga atattgggca atgggcgcaa gcctgaccca gcaacgccgc gtgaaggaag 420
aaggctttcg ggttgtaaac ttcttttctg ggggacgaac aaatgacggt accccaggaa 480
taagccacgg ctaactacgt gccagcagcc gcggtaatac gtaggtggca agcgttatcc 540
ggatttattg ggtgtaaagg gcgtgtaggc gggaatgcaa gtcagatgtg aaaactatgg 600
gctcaaccca tagcctgcat ttgaaactgt atttcttgag tgctggagag gcaatcggaa 660
ttccgtgtgt agcggtgaaa tgcgtagata tacggaggaa caccagtggc gaagcggatt 720
gctggacagt aactgacgct gaggcgcgaa agcgtgggga gcaaacagga ttagataccc 780
tggtagtcca cgccgtaacg atggatacta gtgtgggggg actgaccccc tccgtgccgc 840
agctaacgca ataagtatcc ccacctgggg agtacgatcg caaggttgaa actcaaagga 900
attgacgggg gcccgcacaa gcggtggagt atgtggttta attcgaagca acgcgaagaa 960
ccttaccagg gcttgacatc ctgctaacga accagagatg gattaggtgc ccttcgggga 1020
aagcagagac aggtggtgca tggttgtcgt cagctcgtgt cgtgagatgt tgggttaagt 1080
cccgcaacga gcgcaacccc tattgttagt tgctacgcaa gagcactcta gcgagactgc 1140
cgttgacaaa acggaggaag gtggggacga cgtcaaatca tcatgcccct tacgtcctgg 1200
gccacacacg tactacaatg gcggttaaca aagagaggca agaccgcgag gtggagcaaa 1260
tctcaaaaag ccgtcccagt tcggatcgca ggctgcaacc cgcctgcgtg aagttggaat 1320
cgctagtaat cgcggatcag catgccgcgg tgaatacgtt cccgggcctt gtacacaccg 1380
cccgtcacac catgagagtc gggaacaccc gaagtccgta gcctaaccgc aaggggggcg 1440
cggccgaagg tgggttcgat aattggggtg aagtcgtaac aaggtagccg t 1491

<210> SEQ ID NO 53
<211> LENGTH: 1495
<212> TYPE: DNA
<213> ORGANISM: Clostridium coccoides
<220> FEATURE:
<221> NAME/KEY: rRNA
<222> LOCATION: (1)..(1495)
<223> OTHER INFORMATION: 16S rRNA coding gene sequence of Clostridium
strain 33

<400> SEQUENCE: 53
agagtttgat cctggctcag gatgaacgct ggcggcgtgc ctaacacatg caagtcgaac 60
gggtgtacgg ggaggaaggc ttcggccgga aaacctgtgc atgagtggcg gacgggtgag 120
taacgcgtgg gcaacctggc ctgtacaggg ggataacact tagaaatagg tgctaatacc 180
gcataacggg ggaagccgca tggcttttcc ctgaaaactc cggtggtaca ggatgggccc 240
gcgtctgatt agccagttgg cagggtaacg gcctaccaaa gcgacgatca gtagccggcc 300
tgagagggcg gacggccaca ctgggactga gacacggccc agactcctac gggaggcagc 360
agtgggggat attgcacaat gggggaaacc ctgatgcagc gacgccgcgt gggtgaagaa 420
gcgcctcggc gcgtaaagcc ctgtcagcag ggaagaaaat gacggtacct gaagaagaag 480
ccccggctaa ctacgtgcca gcagccgcgg taatacgtag ggggcaagcg ttatccggat 540
ttactgggtg taaagggggc gcagacggcg atgcaagcca ggagtgaaag cccggggccc 600
aaccccggga ctgctcttgg aactgcgtgg ctggagtgca ggaggggcag gcggaattcc 660
tggtgtagcg gtgaaatgcg tagatatcag aggaacaccg gtggcgaaag cggcctgctg 720
gactgcaact gacgttgagg cccgaaagcg gtgggagcaa acaggattag ataccctggt 780
agtccacgcc gtaaacgatg attactaggt gtcggggagc agagactgcc cggtgccgca 840
gcccaacgca ttaagtatcc acctggggag tacgttcgca agaatgaaac tcaaaggaat 900
tgacggggac ccgcacaagc ggtggagcat gtggtttaat tcgaagcaac gcgaagaacc 960
ttaccaggcc ttgacatccc cctggatggc ccgtaacggg gccagccctt tttgggcagg 1020
ggagacaggt ggtgcatggt tgtcgtcagc tcgtgtcgtg agatgttggg ttaagtcccg 1080
caacgagcgc aacccctgcc cgcagtagcc agcattttag atggggactc tgcggggact 1140
gccggggaca acccggagga aggcggggat gacgtcaaat catcatgccc cttatggcct 1200
gggctacaca cgtgctacaa tggcgccgac agagggagga gaagcggcga cgcggagcga 1260
accccaaaaa cggcgtccca gttcggattg tagtctgcaa cccgactaca tgaagccgga 1320
atcgctagta atcgcggatc agaatgccgc ggtgaatacg ttcccgggtc ttgtacacac 1380
cgcccgtcac accatgggag ccgggaatgc ccgaagtctg tgaccgaacc cgtaagggga 1440
ggggcagccg aaggcaggcc cggtgactgg ggtgaagtcg taacaaggta gccgt 1495

<210> SEQ ID NO 54
<211> LENGTH: 1493
<212> TYPE: DNA
<213> ORGANISM: Clostridium leptum
<220> FEATURE:
<221> NAME/KEY: rRNA
<222> LOCATION: (1)..(1493)
<223> OTHER INFORMATION: 16S rRNA coding gene sequence of Clostridium strain 34

<400> SEQUENCE: 54
agagtttgat cctggctcag gacgaacgct ggcggcgtgc ttaacacatg caagtcgaac 60
ggagcacccc tgaaggagtt ttcggacaac ggatgggaat gcttagtgtc ggactggtga 120
gtaacgcgtg aggaacctgc cttccagagg gggacaacag ttggaaacga ctgctaatac 180
cgcatgatgc gttggagccg catgactccg acgtcaaaga tttatcgctg gaagatggcc 240
tcgcgtctga tttgttagtt ggtgaggtaa cggcccacca aggcgacgat cagtagccgg 300
actgagaggt tggccggcca cattgggact gagatacggc ccagactcct acgggaggca 360
gcagtgggga atattgggca atggacgcaa gtctgaccca gcaacgccgc gtgaaggaag 420

```
aaggctttcg ggttgtaaac ttcttttaag gggaagagc agaagacggt accccttgaa    480

taagccacgg ctaactacgt gccagcagcc gcggtaatac gtaggtggca agcgttgtcc    540

ggatttactg ggtgtaaagg gcgtgcagcc ggagagacaa gtcagatgtg aaatccacgg    600

gctcaacccg tgaactgcat ttgaaactgt ttcccttgag tgtcggagag gtaatcggaa    660

ttccttgtgt agcggtgaaa tgcgtagata taaggaagaa caccagtggc gaaggcggat    720

tactggacga taactgacgg tgaggcgcga aagcgtgggg agcaaacagg attagatacc    780

ctggtagtcc acgctgtaaa cgatcgatac taggtgtgcg gggactgacc ccctgcgtgc    840

cggagttaac acaataagta tcgcacctgg ggagtacgat cgcaaggttg aaactcaaag    900

gaattgacgg gggcccgcac aagcggtgga ttatgtggtt taattcgaag caacgcgaag    960

aaccttacca gggcttgaca tcctgctaac gaagtagaga tacattaggt gcccttcggg   1020

gaaagcagag acaggtggtg catggttgtc gtcagctcgt gtcgtgagat gttgggttaa   1080

gtcccgcaac gagcgcaacc cctattgtta gttgctacgc aagagcactc tagcgagact   1140

gccgttgaca aaacggagga aggcggggac gacgtcaaat catcatgccc cttatgtcct   1200

gggctacaca cgtaatacaa tggcggttaa caaagggatg caaagccgcg aggcagagcg   1260

aaccccaaaa agccgtccca gttcggatcg caggctgcaa cccgcctgcg tgaagtcgga   1320

atcgctagta atcgcggatc agcatgccgc ggtgaatacg ttcccgggcc ttgtacacac   1380

cgcccgtcac accatgagag tcgggaacac ccgaagtccg tagcctaacc gcaaggaggg   1440

cgcggccgaa ggtgggttcg ataattgggg tgaagtcgta acaaggtagc cgt          1493
```

<210> SEQ ID NO 55
<211> LENGTH: 1498
<212> TYPE: DNA
<213> ORGANISM: Clostridium coccoides
<220> FEATURE:
<221> NAME/KEY: rRNA
<222> LOCATION: (1)..(1498)
<223> OTHER INFORMATION: 16S rRNA coding gene sequence of Clostridium strain 35

<400> SEQUENCE: 55

```
agagtttgat cctggctcag gatgaacgct ggcggcgtgc ctaacacatg caagtcgaac     60

gggtgtacag aagggaagat tacggtcgga aggtctgtgc atgagtggcg gacgggtgag    120

taacgcgtgg gcaacctggc ctgtacaggg ggataacact tagaaatagg tgctaatacc    180

gcataacggg ggaagccgca tggcttttcc ctgaaaactc cggtggtaca ggatgggccc    240

gcgtctgatt attttttttg tcagggtaac ggcctaccaa agcgacgatc agtagccggc    300

ctgagagggc ggacggccac actgggactg agacacggcc cagactccta cgggaggcag    360

cagtggggga tattgcacaa tgggggggaac cctgatgcag cgacgccgcg tgggtgaaga    420

agcgcctcgg cgcgtaaagc cctgtcagca gggaagaaaa tgacggtacc tgaagaagaa    480

gccccggcta actacgtgcc agcagccgcg gtaatacgta ggggcaagc gttatccgga     540

tttactgggt gtaaaggggg cgcagacggc gatgcaagcc aggagtgaaa gcccggggcc    600

caaccccggg actgctcttg ggaactgcgg tggctggagt gcaggagggg caggccggaa    660

ttcctggtgt agcggtgaaa tgcgtagata tcaggaggaa caccggtggc gaaggcggcc    720

tgctggactg caactgacgt tgaggcccga aagcgtgggg agcaaacagg attagatacc    780

ctggtagtca cgccgtaaac gatgattact aggtgtcggg gagcagagac tgcccggtgc    840

cgcagccaac gcattaagta atccacctgg ggagtacgtt cgcaagaatg aaactcaaag    900
```

```
gaattgacgg ggacccgcac aagcggtgga gcatgtggtt taattcgaag caacgcgaag    960
aaccttacca ggccttgaca tcccccctgga tggcccgtaa cggggtcagc ctttcggggc   1020
aggggagaca ggtggtgcat ggttgtcgtc agctcgtgtc gtgagatgtt gggttaagtc   1080
ccgcaacgag cgcaacccct gcccgcagta gccagcattt tagatgggga ctctgcgggg   1140
actgccgggg acaacccgga ggaaggcggg gatgacgtca aatcatcatg ccccttatgg   1200
cctgggctac acacgtgcta caatggcgcc gacagaggga ggcgaagcgg cgacgcggag   1260
cgaaccccaa aaacggcgtc ccagttcgga ttgtagtctg caacccgact acatgaagcc   1320
ggaatcgcta gtaatcgcgg atcagaatgc cgcggtgaat acgttcccgg gtcttgtaca   1380
caccgcccgt cacaccatgg gagccgggaa tgcccgaagt ctgtgaccga acccgtaagg   1440
ggaggggcag ccgaaggcag gcccggtgac tggggtgaag tcgtaacaag gtagccgt      1498
```

<210> SEQ ID NO 56
<211> LENGTH: 1491
<212> TYPE: DNA
<213> ORGANISM: Clostridium leptum
<220> FEATURE:
<221> NAME/KEY: rRNA
<222> LOCATION: (1)..(1491)
<223> OTHER INFORMATION: 16S rRNA coding gene sequence of Clostridium
strain 36

<400> SEQUENCE: 56

```
agagtttgat catggctcag gacgaacgct ggcggcaagc ttaacacatg caagtcgaac     60
ggagcgccta tgaaggagat ttcggtcaac ggaataggct gcttagtggc tgacgggtga    120
gtaacgcgtg aggaacctgc ctttcagagg gggacaacag ttggaaacga ctgctaatac    180
cgcataacac ataggtgtcg catggcattt atgtcaaaga tttatcgctg aaagatggcc    240
tcgcgtctga ttagctagtt ggtgaggtaa cggctcacca aggcgacgat cagtagccgg    300
actgagaggt tagccggcca cattgggact gagatacggc ccagactcct acgggaggca    360
gcagtgggga atattgggca atggacgcaa gtctgaccca gcaacgccgc gtgaaggaag    420
aaggctttcg ggttgtaaac ttcttttaag agggaagagc agaagacggt acctcttgaa    480
taagccacgg ctaactacgt gccagcagcc gcggtaatac gtagtggcaa gcgttgtccg    540
gatttactgg gtgtaaaggg cgtgtagccg ggctgacagt cagatgtgaa attccggggc    600
tcaaccccgg acctgcattt gaaactgttg gtcttgagta tcggagaggc aggcggaatt    660
cctagtgtag cggtgaaatg cgtagatatt aggaggaaca ccagtggcga aggcggcctg    720
ctggacgaca actgacggtg aggcgcgaaa gcgtggggag caaacaggat tagataccct    780
ggtagtccac gctgtaaacg atggatacta ggtgtgcggg gactgacccc ctgcgtgccg    840
cagttaacac aataagtatc ccacctgggg agtacgatcg caaggttgaa actcaaagga    900
attgacgggg gcccgcacaa gcggtggatt atgtggttta attcgatgca acgcgaagaa    960
ccttaccagg gcttgacatc ctgctaacga ggtagagata cgtcaggtgc ccttcgggga   1020
aagcagagac aggtggtgca tggttgtcgt cagctcgtgt cgtgagatgt tgggttaagt   1080
cccgcaacga gcgcaaccct tattgttagt tgctacgcaa gagcactcta gcgagactgc   1140
cgttgacaaa acggaggaag gtggggacga cgtcaaatca tcatgcccct tatgtcctgg   1200
gctacacacg taatacaatg gcggtaaaca gagggatgca atactgcgaa gtggagcgaa   1260
cccctaaaag ccgtcccagt tcagattgca gtctgcaact cgactgcatg aagtcggaat   1320
cgctagtaat cgcggatcag catgccgcgg tgaatacgtt cccgggcctt gtacacaccg   1380
```

cccgtcacac catgagagtc gggaacaccc gaagtccgta gcctaaccgc aaggagggcg 1440
cggccgaagg tgggttcgat aattggggtg aagtcgtaac aaggtagccg t 1491

<210> SEQ ID NO 57
<211> LENGTH: 1493
<212> TYPE: DNA
<213> ORGANISM: Clostridium coccoides
<220> FEATURE:
<221> NAME/KEY: rRNA
<222> LOCATION: (1)..(1493)
<223> OTHER INFORMATION: 16S rRNA coding gene sequence of Clostridium
strain 37

<400> SEQUENCE: 57
agagtttgat cctggctcag gatgaacgct ggcggcgtgc ctaacacatg caagtcgaac 60
gggtgtacgg ggaggaaggc ttcggccgga aaacctgtgc atgagtggcg gacgggtgag 120
taacgcgtgg gcaacctggc ctgtacaggg ggataacact tagaaatagg tgctaatacc 180
gcataacggg ggaagccgca tggcttttcc ctgaaaactc cggtggtaca ggatgggccc 240
gcgtctgatt agccagttgg cagggtaacg gcctaccaaa gcgacgatca gtagccggcc 300
tgagagggcg gacggccaca ctgggactga gacacggccc agactcctac gggaggcagc 360
agtgggggat attgcacaat gggggaaac cctgatgcag cgacgccgcg tgagtgaaga 420
agtatttcgg tatgtaaagc tctatcagca gggaagaaaa tgacggtacc tgactaagaa 480
gccccggcta actacgtgcc agcagccgcg gtaatacgta gggggcaagc gttatccgga 540
tttactgggt gtaaagggag cgtagacggc agcgcaagtc tgaagtgaaa tcccatggct 600
taaccatgga actgctttgg aaactgtgca gctggagtgc aggagaggta agcggaattc 660
ctagtgtagc ggtgaaatgc gtagatatta ggaggaacac cagtggcgaa ggcggcttac 720
tggactgtac tgacgttgag gctcgaaagc gtggggagca aacaggatta gataccctgg 780
tagtccacgc cgtaaacgat gattactagg tgttggggga ccaaggtctt cggtgccggc 840
gcaaacgcat taagtaatcc acctggggag tacgttcgca agaatgaaac tcaaaggaat 900
tgacggggac ccgcacaagc ggtggagcat gtggtttaat tcgaagcaac gcgaagaacc 960
ttacctggtc ttgacatccc gatgacgagt gagcaaagtc actttccctt cggggcattg 1020
gagacaggtg gtgcatggtt gtcgtcagct cgtgtcgtga gatgttgggt taagtcccgc 1080
aacgagcgca acccctattt ccagtagcca gcaggtagag ctgggcactc tggagagact 1140
gcccgggata accgggagga aggcggggat gacgtcaaat catcatgccc cttatgatca 1200
gggctacaca cgtgctacaa tggcgtaaac aaagggaagc gagacggtga cgttgagcaa 1260
atcccaaaaa taacgtccca gttcggattg tagtctgcaa ctcgactaca tgaagctgga 1320
atcgctagta atcgcgaatc agaatgtcgc ggtgaatacg ttcccgggtc ttgtacacac 1380
cgcccgtcac accatgggag tcggaaatgc ccgaagtcag tgacctaacc gaaaggaagg 1440
agctgccgaa ggtggagccg gtaactgggg tgaagtcgta acaaggtagc cgt 1493

<210> SEQ ID NO 58
<211> LENGTH: 1493
<212> TYPE: DNA
<213> ORGANISM: Clostridium leptum
<220> FEATURE:
<221> NAME/KEY: rRNA
<222> LOCATION: (1)..(1493)
<223> OTHER INFORMATION: 16S rRNA coding gene sequence of Clostridium
strain 38

<400> SEQUENCE: 58
aaagtttgat cctggctcag gacgaacgct ggcggcgtgc ttaacacatg caagtcgaac 60
ggagcacccc tgaaggagtt ttcggacaac ggatgggaat gcttagtggc ggactggtga 120
gtaacgcgtg aggaacctgc cttccagagg gggacaacag ttggaaacga ctgctaatac 180
cgcatgatgc gttggagccg catgactccg acgtcaaaga tttatcgctg gaagatggcc 240
tcgcgtctga ttagctagtt ggtgaggtaa cggcccacca aggcgacgat cagtagccgg 300
actgagaggt tggccggcca cattgggact gagatacggc ccagactcct acgggaggca 360
gcagtgggga atattgggca atggacgcaa gtctgaccca gcaacgccgc gtgaaggaag 420
aaggctttcg ggttgtaaac ttcttttaag gggaagagc agaagacggt accccttgaa 480
taagccacgg ctaactacgt gccagcagcc gcggtaatac gtagtggcaa gcgttgtccg 540
gatttactgg gtgtaaaggg cgtgcagccg gagagacaag tcagatgtga aatccacggg 600
ctcaacccgt gaactgcatt tgaaactgtt tcccttgagt gtcggagagg taatcggaat 660
tccttgtgta gcggtgaaat gcgtagatat aaggaagaac accagtggcg aaggcggatt 720
actggacgat aaactgacgg tgaggcgcga aagcgtgggg agcaaacagg attagatacc 780
ctggtagtcc acgctgtaaa cgatcgatac taggtgtgcg gggactgacc ccctgcgtgc 840
cggagttaac acaataagta tcgcacctgg ggagtacgat cgcaaggttg aaactcaaag 900
gaattgacgg gggcccgcac aagcggtgga ttatgtggtt taattcgaag caacgcgaag 960
aaccttacca gggcttgaca tcctgctaac gaagtagaga tacattaggt gcccttcggg 1020
gaaagtagag acaggtggtg catggttgtc gtcagctcgt gtcgtgagat gttgggttaa 1080
gtcccgcaac gagcgcaacc cctattgtta gttgctacgc aagagcactc tagcgagact 1140
gccgttgaca aaacggagga aggcggggac gacgtcaaat catcatgccc cttatgtcct 1200
gggctacaca cgtaatacaa tggcggttaa caaagggatg caaagccgcg aggcagagcg 1260
aaccccaaaa agccgtccca gttcggatcg caggctgcaa cccgcctgcg tgaagtcgga 1320
atcgctagta atcgcggatc agcatgccgc ggtgaatacg ttcccgggcc ttgtacacac 1380
cgcccgtcac accatgagag tcgggaacac ccgaagtccg tagcctaacc gcaaggaggg 1440
cgcggccgaa ggtgggttcg ataattgggg tgaagtcgta acaaggtagc cgt 1493

<210> SEQ ID NO 59
<211> LENGTH: 1511
<212> TYPE: DNA
<213> ORGANISM: Clostridium leptum
<220> FEATURE:
<221> NAME/KEY: rRNA
<222> LOCATION: (1)..(1511)
<223> OTHER INFORMATION: 16S rRNA coding gene sequence of Clostridium
strain 39

<400> SEQUENCE: 59
agagtttgat cctggctcag gacgaacgct ggcggcgtgc ttaacacatg caagtcgaac 60
ggagcacccc tgaaggagtt ttcggacaac ggatgggaat gcttagtggc ggactggtga 120
gtaacgcgtg aggaacctgc cttccagagg gggacaacag ttggaaacga ctgctaatac 180
cgcatgatgc gttggagccg catgactccg acgtcaaaga tttatcgctg gaagatggcc 240
tcgcgtctga ttagctagtt ggtgaggtaa cggcccacca aggcgacgat cagtagccgg 300
actgagaggt tggccggcca cattgggact gagatacggc ccagactcct acgggaggca 360
gcagtgggga atattgggca atggacgcaa gtctgaccca gcaacgccgc gtgaaggaag 420

-continued

```
aaggctttcg ggttgtaaac ttcttttaag gggaagagc agaagacggt acccccttgaa    480

taagccacgg ctaactacgt gccagcagcc gcggtaatac gtaggtggca agcgttgtcc    540

ggatttactg ggtgtaaagg gcgtgcagcc ggagagacaa gtcagatgtg aaatccacgg    600

gctcaacccg tgaactgcat ttgaaactgt ttcccttgag tgtcggagag gtaatcggaa    660

ttccttgtgt agcggtgaaa tgcgtagata taaggaagac accagtggcg aagcggatta    720

ctggacgata actgacggtg aggcgcgaaa gcgtggggag caaacaggat tagatacctg    780

ggtagtcaac gctgtaaacg atcgatacta ggtggtgcgg gggacttgac cccctgccgt    840

tgccggagtt aacaccaata aagtattcgg caccctgggg agtacgatcg caaaggttga    900

aaactcaaaa gaaatggacg gggggccccg ccccaagcgg gtgggattat gttggtttat    960

ttcgaaagca acgcgaagaa ccctaacagg gcttgacatc ctgctaacga agtagagata   1020

cattaggtgc ccttcgggga aagtagagac aggtggtgca tggttgtcgt cagctcgtgt   1080

cgtgagatgt tgggttaagt cccgcaacga gcgcaacccc tattgttagt tgctacgcaa   1140

gagcactcta gcgagactgc cgttgacaaa acggaggaag gcggggacga cgtcaaatca   1200

tcatgcccct tatgtcctgg gctacacacg taatacaatg gcggttaaca aagggatgca   1260

aagccgcgag gcagagcgaa ccccaaaaag ccgtcccagt tcggatcgca ggctgcaacc   1320

cgcctgcgtg aagtcggaat cgctagtaat cgcggatcag catgccgcgg tgaatacgtt   1380

cccgggcctt gtacacaccg cccgtcacac catgagagtc gggaacaccc gaagtccgta   1440

gcctaaccgc aaggagggcg cggccgaagg tgggttcgat aattggggtg aagtcgtaac   1500

aaggtagccg t                                                        1511


<210> SEQ ID NO 60
<211> LENGTH: 1499
<212> TYPE: DNA
<213> ORGANISM: Clostridium leptum
<220> FEATURE:
<221> NAME/KEY: rRNA
<222> LOCATION: (1)..(1499)
<223> OTHER INFORMATION: 16S rRNA coding gene sequence of Clostridium
      strain 40

<400> SEQUENCE: 60

agagtttgat cctggctcag gataaacgct ggcggcatgc ctaacacatg caagtcgaac     60

ggagcgcctt ggaaggagac ttcggtcaac ggaagaggag gcttagtggc ggacgggtga    120

gtaacgcgtg aggaacctgc ctcagagagg gggataacac accgaaaggt gtgctaatac    180

cgcataacat atgagagggg catccctttc atatcaaaga tttattgctt tgagatggcc    240

tcgcgtccaa ttagctagtt ggtgaggtaa cggcccacca aggcgacgat tggtagccgg    300

actgagaggt tgaacggcca cattgggact gagacacggc ccagactcct acgggaggca    360

gcagtgggga atattgcaca atgggggaa ccctgatgca gcaatgccgc gtgaaggatg    420

aaggttttcg gattgtaaac ttcttttgta cgggacgaag aaagtgacgg taccgtaaga    480

ataagccacg gctaactacg tgccagcagc cgcggtaata cgtaggtggc aagcgttatc    540

cggatttact gggtgtaaag ggcgagtagg cgggattgca agtcagatgt gaaaactatg    600

ggctcaaccg atagagtgca tttgaaactg cagttcttga gtgatggaga ggcaggcgga    660

attcccggtg tagcggtgga atgcgtagat atcgggaggg aacaccagtg gcgaaggcgg    720

cctgctggac attaactgac gctgatgcgc gaaagcgtgg ggagcaaaca ggattagata    780

ccctggtagt cacgctgtaa acgatgatta ctaggtgtgg ggggtactga ccccccttccc    840
```

```
gtgccggagt taacacaata agtaatccac ctggggagta cggccgcaag gttgaaactc    900

aaaggaattg acgggggccc gcacaagcag tggagtatgt ggttttaatt cgaagcaacg    960

cgaagaacct taccagggct tgacatgggg atgaccgctt tagagataga gctttctctt   1020

cggagacatc ccacacaggt ggtgcatggt tgtcgtcagc tcgtgtcgtg agatgttggg   1080

ttaagtcccg caacgagcgc aacccttatt gttagttgct acgcaagagc actctagcga   1140

gactgccgtt gacaaaacgg aggaaggtgg ggacgacgtc aaatcatcat gccctttatg   1200

tcctgggcta cacacgtact acaatggcgg acatacagag ggaagcaaga cagcgatgtg   1260

gagcaaatcc ctaaaagccg tctcagttca gattgcaggc tgcaacccgc ctgcatgaag   1320

tcggaattgc tagtaatcgc ggatcagcat gccgcggtga atacgttccc gggccttgta   1380

cacaccgccc gtcacaccat gagagtcgga aacacccgaa gcctgtagcc caaccgcaag   1440

gggggcgcag tcgaaggtgg gtctgataat tggggtgaag tcgtaacaaa ggtagccgt    1499


<210> SEQ ID NO 61
<211> LENGTH: 1512
<212> TYPE: DNA
<213> ORGANISM: Clostridium coccoides
<220> FEATURE:
<221> NAME/KEY: rRNA
<222> LOCATION: (1)..(1512)
<223> OTHER INFORMATION: 16S rRNA coding gene sequence of Clostridium
      strain 41

<400> SEQUENCE: 61

agagtttgat cctggctcag gatgaacgct ggcggcgtgc ttaacacatg caagtcgaac     60

ggagatatca ttttcgaagc gattagttta ctaagagcgg agatgttgct atcttagtgg    120

cggacgggtg agtaacgcgt gggtaacctg ccttgcactg ggggataaca cttagaaata    180

ggtgctaata ccgcataaca gtaggagacg catgtctttt acttgaaaac tccggtggtg    240

taagatggac ccgcgtctga ttagcttgtt ggcggggtaa cggcccacca aggcaacgat    300

cagtagccgg cctgagaggg tgaacggcca cattgggact gagacacggc ccaaactcct    360

acgggaggca gcagtgggga atattggaca atgggggaa ccctgatcca gcgacgccgc     420

gtgagtgaag aagtatttcg gtatgtaaag ctctatcagc agggaagaaa gaaatgacgg    480

tacctgacta agaagccccg gctaactacg tgccagcagc cgcggtaata cgtagggggc    540

aagcgttatc cggatttact gggtgtaaag ggagcgtaga cggcgatgca agtctgaagt    600

gaaaggcggg ggcccaaccc ccggactgct ttggaaactg tatggctgga gtgcaggaga    660

ggtaagtgga attcctagtg tagcggtgaa atgcgtagat attaggagga acaccagtgg    720

cgaaagcggc ttactggact gtaactgacg ttgaggctcg aaagcgtggg gagcaaacaa    780

gattagatac cctggtagtca cgccgtaaac gatgatcacc ggtttcggtg ggttatggac    840

ccatcggttg cgcagcaaac gcagtagtga tccacctggg gagtaacgtt cgcaagaatg    900

aaacttcaaa ggaaatgacg ggggacccgg cacaagcggt ggaggcatgt gtttaattcg    960

aagcaacgcg aagaacctta cccaagtctt gacatcccgt gacgagtgag taacgtcact   1020

ttcccttcgg ggcagcggag acaggtggtg catggttgtc gtcagctcgt gtcgtgagat   1080

gttgggttaa gtcccgcaac gagcgcaacc cctatcctta gtagccagcg agttaggtcg   1140

ggcactctag ggagactgcc ggggacaacc cggaggaagg tggggatgac gtcaaatcat   1200

catgcccctt atgatttggg ctacacacgt gctacaatgg cgtaaacaaa gggaagcgag   1260

cctgtgaagg taagcgaatc ccagaaataa cgtctcagtt cggattgtag tctgcaactc   1320
```

-continued

```
gactacatga agctggaatc gctagtaatc gcggatcaga atgccgcggt gaatacgttc   1380

ccgggtcttg tacacaccgc ccgtcacacc atgggagtcg gaaatgcccg aagtctgtga   1440

cccaacctga gaaggaggga gcagccgaag gcaggtcgga tgactggggt gaagtcgtaa   1500

caaggtagcc gt                                                       1512


<210> SEQ ID NO 62
<211> LENGTH: 17
<212> TYPE: DNA
<213> ORGANISM: Artificial
<220> FEATURE:
<223> OTHER INFORMATION: Artificially synthesized primer sequence

<400> SEQUENCE: 62

ggtgaatacg ttcccgg                                                    17


<210> SEQ ID NO 63
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 63

tacggctacc ttgttacgac tt                                              22


<210> SEQ ID NO 64
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 64

aaatgacggt acctgactaa                                                 20


<210> SEQ ID NO 65
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 65

ctttgagttt cattcttgcg aa                                              22


<210> SEQ ID NO 66
<211> LENGTH: 16
<212> TYPE: DNA
<213> ORGANISM: Artificial
<220> FEATURE:
<223> OTHER INFORMATION: Artificially synthesized primer sequence

<400> SEQUENCE: 66

gcacaagcag tggagt                                                     16


<210> SEQ ID NO 67
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 67

cttcctccgt tttgtcaa                                                   18
```

-continued

```
<210> SEQ ID NO 68
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 68

gagaggaagg tcccccac                                                    18


<210> SEQ ID NO 69
<211> LENGTH: 19
<212> TYPE: DNA
<213> ORGANISM: Artificial
<220> FEATURE:
<223> OTHER INFORMATION: Artificially synthesized primer sequence

<400> SEQUENCE: 69

cgctacttgg ctggttcag                                                   19
```